(12) United States Patent
Zhou et al.

(10) Patent No.: US 11,499,196 B2
(45) Date of Patent: Nov. 15, 2022

(54) CELL-FREE DNA METHYLATION PATTERNS FOR DISEASE AND CONDITION ANALYSIS

(71) Applicants: THE REGENTS OF THE UNIVERSITY OF CALIFORNIA, Oakland, CA (US); UNIVERSITY OF SOUTHERN CALIFORNIA, Los Angeles, CA (US)

(72) Inventors: Xianghong Jasmine Zhou, Los Angeles, CA (US); Shuli Kang, Los Angeles, CA (US); Steven Dubinett, Los Angeles, CA (US); Wenyuan Li, Los Angeles, CA (US); Qingjiao Li, Los Angeles, CA (US)

(73) Assignees: The Regents of the University of California, Oakland, CA (US); University of Southern California, Los Angeles, CA (US)

( * ) Notice: Subject to any disclaimer, the term of this patent is extended or adjusted under 35 U.S.C. 154(b) by 428 days.

(21) Appl. No.: 16/307,821

(22) PCT Filed: Jun. 7, 2017

(86) PCT No.: PCT/IB2017/053378
§ 371 (c)(1),
(2) Date: Dec. 6, 2018

(87) PCT Pub. No.: WO2017/212428
PCT Pub. Date: Dec. 14, 2017

(65) Prior Publication Data
US 2020/0131582 A1    Apr. 30, 2020

Related U.S. Application Data

(60) Provisional application No. 62/491,560, filed on Apr. 28, 2017, provisional application No. 62/473,829, filed on Mar. 20, 2017, provisional application No. 62/347,010, filed on Jun. 7, 2016.

(51) Int. Cl.
| | | |
|---|---|---|
| *C12Q 1/6886* | (2018.01) | |
| *G16B 20/00* | (2019.01) | |
| *G16B 25/00* | (2019.01) | |
| *G16B 30/00* | (2019.01) | |
| *G16B 50/00* | (2019.01) | |
| *G16B 40/20* | (2019.01) | |
| *G16B 30/10* | (2019.01) | |
| *G16B 25/10* | (2019.01) | |
| *G16B 20/30* | (2019.01) | |
| *G16B 20/20* | (2019.01) | |
| *G16B 30/20* | (2019.01) | |

(52) U.S. Cl.
CPC ........... *C12Q 1/6886* (2013.01); *G16B 20/00* (2019.02); *G16B 20/20* (2019.02); *G16B 20/30* (2019.02); *G16B 25/00* (2019.02); *G16B 25/10* (2019.02); *G16B 30/00* (2019.02); *G16B 30/10* (2019.02); *G16B 30/20* (2019.02); *G16B 40/20* (2019.02); *G16B 50/00* (2019.02); *C12Q 2600/154* (2013.01)

(58) Field of Classification Search
CPC ....................... C12Q 1/6886; C12Q 2600/154; G16B 20/30; G16B 30/10; G16B 20/20; G16B 25/10; G16B 20/00; G16B 30/20; G16B 25/00; G16B 40/20; G16B 30/00; G16B 50/00
See application file for complete search history.

(56) References Cited

U.S. PATENT DOCUMENTS

| | | |
|---|---|---|
| 2010/0143929 A1 | 6/2010 | Levenson et al. |
| 2010/0240549 A1* | 9/2010 | Brown ................. C12Q 1/6858 506/9 |
| 2013/0085681 A1 | 4/2013 | Deciu et al. |
| 2016/0017419 A1 | 1/2016 | Chiu et al. |

FOREIGN PATENT DOCUMENTS

| | | |
|---|---|---|
| WO | WO 99/18124 | 4/1999 |
| WO | WO 2014/039556 | 3/2014 |
| WO | WO 2015/159292 | 10/2015 |
| WO | WO 2016/115530 | 7/2016 |
| WO | WO 2020/041611 | 2/2020 |

OTHER PUBLICATIONS

Extended European Search Report Issued in Corresponding European Patent Application No. 17809820.8, dated Jun. 16, 2020.
Husseiny, et al., "Development of a Quantitative Methylation-Specific Polymerase Chain Reaction Method for Monitoring Beta Cell Death in Type 1 Diabetes," *PLOS One*, 7(10): e47942, 2012.
Husseiny, et al., "Table S1. Oligonucleotides Used In This Study," PLOS One, 9(4): 1-2, 2014.
Husseiny, et al., "Tissue-Specific Methylation of Human Insulin Gene and PCR Assay for Monitoring Beta Cell Death," *PLOS One*, 9(4): e94591, 2014.
Madi, et al., "The Determination of Tissue-Specific DNA Methylation Patterns in Forensic Biofluids Using Bisulfite Modification and Pyrosequencing," *Electrophoresis*, 33(12): 1736-1745, 2012.
Baylin et al., "Aberrant patterns of DNA methylation, chromatin formation and gene expression in cancer," *Hum. Mol. Genet.*, 2001, 10:687-692.
Bettegowda et al., "Detection of circulating tumor DNA in early- and late-stage human malignancies" *Sci. Transl. Med.*, 2014, 6:224ra24.
Bowman et al., "The beta distribution, moment method," *Far East J. Theor. Stat.*, 2007, 23:133-164.

(Continued)

Primary Examiner — Jerry Lin
(74) *Attorney, Agent, or Firm* — Norton Rose Fulbright US LLP

(57) ABSTRACT

Disclosed herein are methods and systems of utilizing sequencing reads for detecting and quantifying the presence of a tissue type or a disease type in cell-free DNA prepared from blood samples.

31 Claims, 25 Drawing Sheets

(56) References Cited

OTHER PUBLICATIONS

Burrell et al., "The causes and consequences of genetic heterogeneity in cancer evolution" *Nature*, 2013, 501:338-345.
Chan et al., "Noninvasive detection of cancer-associated genome-wide hypothylation and copy number aberrations by plasma DNA bisulfite sequencing" *Proc. Natl. Acad. Sci. U.S.A.*, 2013, 110:18761-18768.
Cheishvili et al., "DNA demethylation and invasive cancer: implications for therapeutics" *Br. J. Pharmacol.*, 2015, 172:2705-2715.
Greenman et al., "Patterns of somatic mutation in human cancer genomes" *Nature*, 2007, 446:153-158.
Guo et al., "Identification of methylation haplotype blocks aids in deconvolution of heterogeneous tissue samples and tumor tissue-of-origin mapping from plasma DNA" *Nat. Genet.*, 2017, 49:635-642.
Houseman et al., "DNA methylation arrays as surrogate measures of cell mixture distribution" *BMC Bioinformatics*, 2012, 13:86.
International Search Report and Written Opinion issued in International Patent Application No. PCT/IB2017/053378, dated Nov. 8, 2017.
Kang et al., "CancerLocator: non-invasive cancer diagnosis and tissue-of-origin prediction using methylation profiles of cell-free DNA" *Genome Biol.*, 2017, 18:53.
Koestler et al., "Blood-based profiles of DNA methylation predict the underlying distribution of cell types: a validation analysis" *Epigenetics*, 2013, 8:816-826.
Koestler et al., "Peripheral blood immune cell methylation profiles are associated with nonhematopoietic cancers" *Cancer Epidemiol. Biomarkers Prev.*, 2012, 21:1293-1302.
Krueger et al., "Bismark: a flexible aligner and methylation caller for Bisulfite-Seq applications" *Bioinformatics*, 2011, 27:1571-1572.
Landan et al., "Epigenetic polymorphism and the stochastic formation of differentially methylated regions in normal and cancerous tissues" *Nat. Genet.*, 2012, 44:1207-1214.
Landau et al., "Locally Disordered Methylation Forms the Basis of Intratumor Methylome Variation in Chronic Lymphocytic Leukemia" *Cancer Cell*, 2014, 26:813-825.
Li et al., "Distinct evolution and dynamics of epigenetic and genetic heterogeneity in acute myeloid leukemia" *Nat. Med.*, 2016, 22:792-799.
Li et al., "Dynamic evolution of clonal epialleles revealed by methclone" *Genome Biol.*, 2014, 15:472.
Newman et al., "An ultrasensitive method for quantitating circulating tumor DNA with broad patient coverage" *Nat. Med.*, 2014, 20:548-554.
Newman et al., "Integrated digital error suppression for improved detection of circulating tumor DNA" *Nat. Biotechnol.*, 2016, 34:547-555.
Plass et al., "Mutations in regulators of the epigenome and their connections to global chromatin patterns in cancer" *Nat. Rev. Genet.*, 2013, 14:765-780.
Roy et al., "Driver mutations of cancer epigenomes" *Protein Cell*, 2014, 5:265-296.
Schmitt et al., "Implications of genetic heterogeneity in cancer" *Ann. N.Y. Acad. Sci*, 2012, 1267:110-116.
Shah et al., "An empirical study of stochastic variational algorithms for the Beta Bernoulli process" International Conference on Machine Learning (ICML), 2015, 10 Pages.
Sharma, S., "Tumor markers in clinical practice: general principles and guidelines" *Indian J. Med. Paediatr. Oncol.*, 2009, 30:1.
Sigalotti et al., "Epigenetic drugs as pleiotropic agents in cancer treatment: biomolecular aspects and clinical applications" *J. Cell. Physiol.*, 2007, 212:330-344.
Smith et al., "Unraveling the epigenetic code of cancer for therapy" *Trends Genet*, 2007, 23:449-456.
Sturgeon et al., "Use of tumor markers in clinical practice: quality requirements" American Association for Clinical Chemistry, 2009.
Sun et al., "Plasma DNA tissue mapping by genome-wide methylation sequencing for noninvasive prenatal, cancer and transplantation assessments" *Proc. Natl. Acad. Sci. U.S.A.*, 2015, 112:E5503-12.
Swanton et al., "Epigenetic noise fuels cancer evolution" *Cancer Cell*, 2014, 26:775-776.
Turner et al., "Genetic heterogeneity and cancer drug resistance" *Lancet Oncol.*, 2012, 13:e178-e185.
Weinstein et al., "The Cancer Genome Atlas Pan-Cancer analysis project" *Nat. Genet.*, 2013, 45:1113-1120.
Yuan et al., "BitPhylogeny: a probabilistic framework for reconstructing intra-tumor phylogenies" *Genome Biol*, 2015, 16:36.
Zheng et al., "MethylPurify: tumor purity deconvolution and differential methylation detection from single tumor DNA methylomes" *Genome Biol.*, 2014, 15:419.

\* cited by examiner

C. Tumor Size and Prediction Score

| Patient | Tumor Size | Prediction Score | Survival |
|---|---|---|---|
| Patient 1 | 16 | 34.2 | Survived |
| Patient 2 | 13 | 55.4 | Passed Away |

CELL-FREE DNA METHYLATION PATTERNS FOR DISEASE AND CONDITION ANALYSIS

PRIORITY

This application is a national phase application under 35 U.S.C. § 371 of International Application No. PCT/IB2017/053378 filed Jun. 7, 2017, claims priority to and the benefit of U.S. Provisional Patent Application 62/347,010 filed on Jun. 7, 2016, U.S. Provisional Patent Application 62/473,829 filed on Mar. 20, 2017, and U.S. Provisional Patent Application 62/491,560 filed on Apr. 28, 2017, all of which are hereby incorporated by reference in their entireties.

STATEMENT REGARDING FEDERALLY-SPONSORED RESEARCH

This invention was made with government support under Grant No. HL108634 awarded by the National Institutes of Health (NIH). The government has certain rights in the invention.

FIELD OF THE INVENTION

The invention disclosed herein generally relates to method for analyzing sequencing data of nucleic acid samples (e.g., cell-free DNA samples). It also relates to methods of cancer diagnosis and prognosis, including the identification, origin, and location of a cancer.

BACKGROUND

Unlike traditional biopsies involving invasive surgery, the liquid biopsies utilize only blood samples obtained with minimal invasiveness. Blood is the only biological material that has contact with almost all human organs (including tumors and inflammatory tissues) through the human circulation system. Therefore, the blood carries a large amount of valuable information and disease signs with regard to the status of many organs. For example, in the blood plasma, cell-free circulating DNAs (abbreviated as cfDNAs), the degraded DNA fragments released from apoptotic or necrotic cells in many organs, are regarded as the mixture of DNAs from many normal tissue cells and diseased cells (e.g., cancerous tumor cells). Therefore, they are one of the best sources for blood-based cancer diagnosis and have recently become of major interest for blood-based cancer diagnosis.

However, DNA fragments from diseased cells often constitute only a small portion of the cfDNA samples, especially at an early stage of the disease. As such, sequencing information representing diseased DNA is often drowned out by sequencing information representing normal DNA. What is needed are methods and/or systems for selectively and sensitively deciphering sequencing information relating to diseased DNA.

Early detection and identification of cancer are highly desired. Traditionally, identification of cancer involves invasive tissue biopsy procedures. There exist no method or apparatus to provide accurate screening and identification of tissue-of-origin of cancer with non-invasive method when the cancer is in an early stage.

Early detection of cancer-before it has had a chance to metastasize-presents the best strategy for increasing cancer survival. Recently, cancer detection using cell-free DNA (cfDNA) from blood has attracted significant interest due to its non-invasive nature. However, tumor cfDNA levels are very low in most early-stage and many advanced stage cancer patients (Bettegowda et al., 2014; Newman et al., 2014). Therefore, the major challenge in cfDNA-based early cancer diagnostics is how to identify the tiny amount of tumor cfDNAs out of total cfDNAs in blood. The mainstream approach to address this challenge is mutation-based, i.e., using targeted deep sequencing (>5,000× coverage), combined with error-suppression techniques, to call cfDNA mutations in a small gene panel (Bettegowda et al., 2014; Newman et al., 2014; Newman et al., 2016). While this approach provides a sensitive way to monitor cancer recurrence when the mutations are known, a small gene panel could not serve diagnostic purposes because mutations can be wide-spread and very heterogeneous, even in the same type of cancer (Burrell et al., 2013; Tumer et al., 2012; Greenman et al., 2007; Schmitt et al., 2012). However, enlarging the gene panel, while maintaining the sequencing depth, is cost-prohibitive. Therefore, there remains the challenge of detecting the trace amount of tumor cfDNA using a different approach, namely, using the cfDNA methylation patterns.

This disclosure discloses different embodiments of machines, apparatuses, computer products, and methods for screening cancers and identifying the tissue-of-origin of cancer cells using blood samples drawn from patients when the cancer is in an early stage.

SUMMARY OF THE INVENTION

In one aspect, provided herein is a method of characterizing a cell-free DNA (cfDNA) sample from a subject. In some embodiments, the method comprises the steps of receiving a plurality of sequencing reads for a cfDNA sample from the subject, wherein each sequencing read comprises methylation sequencing data obtained from a consecutive nucleic acid sequence of 50 or more nucleic acids; calculating a methylation pattern based on a sequencing read in the plurality, wherein the methylation pattern comprises a genomic region corresponding to the consecutive nucleic acid sequence and methylation status of one or more motifs in the genomic region; comparing the methylation pattern with each of one or more pre-established methylation signatures to compute one or more likelihood scores, wherein each of the one or more pre-established methylation signatures correlates with a biological composition, and wherein each pre-established methylation signature comprises at least one pre-determined signature region and pre-determined methylation rate associated therewith; and characterizing the sequencing read as containing the biological composition if at least one of the one or more likelihood scores exceeds a threshold value.

In some embodiments, the method further comprises a step of repeating the comparing and characterizing steps for each sequencing read in the plurality.

In some embodiments, the method further comprises a step of establishing the one or more pre-established methylation signatures based on existing methylation sequencing data (e.g., both array-based and sequencing data).

In some embodiments, the method further comprises a step of determining a level of the biological composition in the cfDNA sample based on the number of sequencing reads containing the biological composition in the plurality of sequencing reads.

In some embodiments, the existing methylation sequencing data is selected from the group consisting of tissue specific sequencing data, disease specific sequencing data, individual sequencing data, population sequencing data, and combinations thereof.

In some embodiments, the cfDNA sample is prepared from a plasma or blood sample from the subject. The biological sample may be any biological liquid such as saliva, amniotic fluid, cystic fluid, spinal or brain fluid, urine, sweat, or tears. It may contain contaminating amounts of cells, such as cells in an amount that is at most or less than about 1, 10, 100, 1000, or 10000 intact cells (on average) per microliter of liquid (or any range derivable therein).

In some embodiments, the biological composition is selected from the group consisting of diseased tissue, cancer tissue, tissue from a specific organ, liver tissue, lung tissue, kidney tissue, colon tissue, T-cells, B-cells, neutrophils, small intestines tissue, pancreas tissue, adrenal glands tissue, esophagus tissue, adipose tissue, heart tissue, brain tissue, placenta tissue, and combinations thereof. Methods, computer programs, and apparatuses described herein can be applied to any disease or condition in which a difference exists in the methylation pattern of cell-free DNA from affected versus unaffected individuals or individuals at a different stage of the disease or condition or having a different prognosis. For example, one can identify the abnormal methylation patterns of cell-free DNAs from oligodendrocyte to diagnose multiple sclerosis, from Pancreatic β-cells to diagnose diabetes Type I, and from pancreatic cells to diagnose pancreatitis based on data to derive the methylation signatures of these diseases. Therefore, in some embodiments, obtaining or generating a methylation profile of cell free DNA from biological samples with the disease are included. In other embodiments, obtaining or generating a methylation profile of cell free DNA from biological samples without the disease or considered disease-free are included.

In some embodiments, the cancer tissue is selected from a group consisting of liver cancer tissue, lung cancer tissue, kidney cancer tissue, colon cancer tissue, brain cancer tissue, pancreas cancer tissue, brain cancer tissue, gastrointestinal cancer tissue, head and neck cancer tissue, bone cancer tissue, tongue cancer tissue, gum cancer tissue, and combinations thereof. In other embodiments, the tissue is selected from a group consisting of liver tissue, brain tissue, lung tissue, kidney tissue, colon tissue, pancreas tissue, brain tissue, gastrointestinal tissue, head and neck tissue, bone, tongue tissue, gum tissue, and combinations thereof.

In some embodiments, the methylation status and pre-determined methylation status is determined at bin level.

In some embodiments, the methylation status and pre-determined methylation status is determined at CpG site level.

In some embodiments, the one or more motifs is a CpG site.

In some embodiments, wherein the method further comprises comparing the level of the biological composition in the cfDNA of the subject to that of the biological composition in a normal subject or a known cancer patient, or a patient known to be affected or afflicted with a particular disease or condition.

In some embodiments, the level of the biological composition in the normal subject or known cancer or other disease patient has been previously determined using the same method or a different method.

In one aspect, provided herein are method for comparing the level of a biological composition from a normal subject to that of the same biological composition from a potential patient. Here, the method as disclosed herein can be used to determine the level of the biological composition using cfDNA samples from both the normal subject and a potential patient.

In one aspect, provided herein are method for comparing the level of a biological composition from a known cancer patient to that of the same biological composition from a potential patient. In another aspect, provided herein are method for comparing the level of a biological composition from a patient with a known disease or condition to that of the same biological composition from a potential patient Here, the method as disclosed herein can be used to determine the level of the biological composition using cfDNA samples from both the normal subject and a potential patient.

It would be understood that cfDNAs from a known patient of any disease can be used as standard for disease diagnosis. It is contemplated that any embodiment discussed herein with respect to cancer can be implemented with respect to any other disease or condition in why methylation profiles in cfDNA differ between normal or non-diseased individuals and diseased individuals.

In one aspect, provided herein is a method of comparing the level of a biological composition in a cell-free (cfDNA) sample from an unknown subject to that of the same biological composition in a normal subject or a known cancer patient. The method comprises the steps of: receiving a first plurality of sequencing reads for a cfDNA sample from the unknown subject, wherein each sequencing read comprises methylation sequencing data obtained from a consecutive nucleic acid sequence of 50 or more nucleic acids; i) calculating a methylation pattern based on a sequencing read in the first plurality, wherein the methylation pattern comprises a genomic region corresponding to the consecutive nucleic acid sequence and methylation status of one or more motifs in the genomic region; ii) comparing the methylation pattern with each of one or more pre-established methylation signatures to compute one or more likelihood scores, wherein each of the one or more pre-established methylation signatures correlates with a biological composition, and wherein each pre-established methylation signature comprises at least one pre-determined signature region and pre-determined methylation rate associated therewith; iii) characterizing the sequencing read as containing the biological composition if at least one of the one or more likelihood scores exceeds a threshold value; iv) repeating the calculating, comparing and characterizing steps for each sequencing read in the first plurality; v) determining a first level of the biological composition in the cfDNA sample from the unknown subject based on the number of sequencing reads containing the biological composition in the first plurality of sequencing reads; receiving a second plurality of sequencing reads for a cfDNA sample from the normal subject or known cancer patient, wherein each sequencing read comprises methylation sequencing data obtained from a consecutive nucleic acid sequence of 50 or more nucleic acids; determining a second level of the biological composition in the cfDNA sample from the patient by carrying out steps i) through v) on the cfDNA sample from the normal subject or known cancer patient; and comparing the first level and second level of the biological composition.

In one aspect, provided herein is a method of detecting changes in composition of a cell-free DNA (cfDNA) sample from a patient. The method comprises the steps of receiving, at a first time point, a first plurality of sequencing reads for a first cfDNA sample from the patient, wherein each sequencing read in the first plurality comprises methylation sequencing data obtained from a first consecutive nucleic acid sequence of 50 or more nucleic acids; i) calculating a first methylation pattern based on a sequencing read in the first plurality, wherein the first methylation pattern comprises a first genomic region corresponding to the first consecutive nucleic acid sequence and methylation status of one or more motifs in the first genomic region; ii) comparing the first methylation pattern with each of one or more pre-established methylation signatures to compute one or more first likelihood scores, wherein each of the one or more pre-established methylation signatures correlates with a biological composition, and wherein each pre-established methylation signature comprises at least one pre-determined signature region and pre-determined methylation rate associated therewith; iii) characterizing the cfDNA as containing the biological composition if at least one of the one or more first likelihood scores exceeds a threshold value; iv) repeating steps i) to iii) for each sequencing read in the first plurality of sequencing reads to quantitate the presence of the biological composition in the cfDNA sample at the first time point; receiving, at a second time point, a second plurality of sequencing reads for a second cfDNA sample from the same patient, wherein each sequencing read in the second plurality comprises methylation sequencing data obtained from a second consecutive nucleic acid sequence of 50 or more nucleic acids; repeating steps i) to iv) for each sequencing read in the second plurality of sequencing reads to quantitate the presence of the biological composition in the cfDNA sample at the second time point; and detecting a change in the biological composition between the first and second time points.

In some embodiments, the biological composition is selected from the group consisting of diseased tissue, cancer tissue, tissue from a specific organ, liver tissue, lung tissue, kidney tissue, colon tissue, T-cells, B-cells, neutrophils, small intestines tissue, pancreas tissue, adrenal glands tissue, esophagus tissue, adipose tissue, heart tissue, brain tissue, placenta tissue, and combinations thereof. In some embodiments, the patient may be determined to have a disease or condition or be determined specifically not to have the disease or condition.

In particular, cancer cells can often display aberrant DNA methylation patterns, such as hypermethylation of the promoter regions of tumor suppressor genes and pervasive hypomethylation of intergenic regions. Therefore, a patient's DNA methylation profile can be a target for cancer evaluation in clinical practice. Hyper/hypo-methylated tumor DNA fragments can be released into the bloodstream via cell apoptosis or necrosis, where these circulation tumor DNA (ctDNA) become part of the circulating cell-free DNA (cfDNA) in plasma. The non-invasive nature of cfDNA methylation profiling may be an effective strategy for general cancer screening.

In developing embodiments for non-invasive cancer screening and identifying the tumor tissue-of-origin, detection and characterization of cell-free DNA in plasma can be an effective method. Liquid biopsy, e.g., blood draw, unlike traditional tissue biopsy, has the potential to diagnose a variety of different malignancies.

The disclosure herein provides, in some embodiments, a probabilistic method that evaluates a patient for cancer using cell-free DNA (cfDNA), including identifying the location of the cancer and/or tumors. The embodiment simultaneously identifies the proportions and the tissue-of-origin of tumor-derived cell-free DNA in a blood sample using genome-wide DNA methylation data. The disclosure comprehensively discloses the embodiments with simulations and real data, and compares performances of the embodiments. This disclosure shows that the predicted tumor burdens are highly consistent with the true values. Notably, the embodiments disclosed herein achieve accurate results on patient plasma samples, despite the fact that the DNA methylation data from these samples has very low sequencing coverage. Such ability to accurately identify the existence as well as the location of tumors is highly desirable in cancer therapy.

According to one embodiment, a computer program product includes a non-transitory computer-readable medium having instructions configured for cancer detection and tissue-of-origin identification, which, when executed by a processor of a computing system, cause the processor to perform the steps of: receiving an instruction to access data of a cell free DNA (cfDNA) methylation profile of a patient stored in the non-transitory computer-readable medium; identifying a plurality of CpG cluster features in the cfDNA methylation profile wherein a total number of the plurality of CpG cluster features is K, K is a positive integer; determining a circulating tumor DNA (ctDNA) burden coefficient $\theta$, where $0 \leq \theta \leq 1$; determining a potential cancer type t; estimating a methylation level $x_k$ for each of the CpG cluster features, where k=1, 2, . . . K; calculating a prediction score $\lambda$ using $\theta$, t, and $x_k$; determining the patient is cancerous having the potential cancer type t, if $\lambda$ is greater than a predetermined threshold; and determining the patient is noncancerous, if $\lambda$ is smaller than the predetermined threshold.

According to another embodiment, an apparatus configured for cancer detection and tissue-of-origin identification, includes a non-transitory memory and a processor coupled to the non-transitory memory, the processor configured to execute steps of: accessing data of a cell free DNA (cfDNA) methylation profile of a patient stored in the non-transitory memory; identifying a plurality of CpG cluster features in the cfDNA methylation profile wherein a total number of the plurality of CpG cluster features is K, K is a positive integer; determining a circulating tumor DNA (ctDNA) burden coefficient $\theta$, where $0 \leq \theta \leq 1$; determining a potential cancer type t; estimating a methylation level $x_k$ for each of the CpG cluster features, where k=1, 2, . . . K; calculating a prediction score $\lambda$ using $\theta$, t, and $x_k$; determining the patient is cancerous having the potential cancer type t, if $\lambda$ is greater than a predetermined threshold; and determining the patient is noncancerous, if $\lambda$ is smaller than the predetermined threshold. As discussed above, this and other embodiments discussed herein may be applied to a disease other than cancer.

According to yet another embodiment, a method for cancer detection and tissue-of-origin identification executed by a computer system includes receiving, by a processor of the computer system, an instruction to access data of a cell free DNA (cfDNA) methylation profile of a patient stored in a non-transitory computer-readable medium, the non-transitory computer-readable medium is in communication with the processor; identifying, by the processor, a plurality of CpG cluster features in the cfDNA methylation profile wherein a total number of the plurality of CpG cluster features is K, K is a positive integer; determining, by the processor, a circulating tumor DNA (ctDNA) burden coefficient $\theta$, where $0 \leq \theta \leq 1$; determining, by the processor, a potential cancer type t; estimating, by the processor, a methylation level $x_k$ for each of the CpG cluster features, where k=1, 2, . . . K; calculating, by the processor, a prediction score $\lambda$ using $\theta$, t, and $x_k$; determining, by the processor, the patient is cancerous having the potential cancer type t, if $\lambda$ is greater than a predetermined threshold;

and determining, by the processor, the patient is noncancerous, if λ is smaller than the predetermined threshold.

In some embodiments, a best solution of the burden θ for P(R|θ, $\mathcal{M}$) is found through a grid search. In some embodiments, the grid search can also be performed using the higher resolution step (0.01%), such as 0.010%, 0.020%, 0.025%, 0.030%, 0.040%, 0.050%, 0.060%, 0.070%, 0.080%, 0.090%, 0.100%, 0.125%, 0.150%, 0.175%, 0.200%, 0.225%, 0.250%, 0.275%, 0.300%, 0.325%, 0.350%, 0.375%, 0.400%, 0.425%, 0.450%, 0.475%, 0.500%, 0.525%, 0.055%, 0.575%, 0.600%, 0.625%, 0.650%, 0.675%, 0.700%, 0.725%, 0.750%, 0.775%, 0.800%, 0.825%, 0.850%, 0.875%, 0.900%, 0.925%, 0.950%, 0.975%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, 999%, and/or 100%, or any range derivable therein. In some embodiments, the grid search can be performed using the higher resolution step (0.001%), such as 0.001%, 0.002%, 0.003%, 0.004%, 0.005%, 0.006%, 0.007%, 0.008%, 0.009%, 0.010%, 0.020%, 0.025%, 0.030%, 0.040%, 0.050%, 0.060%, 0.070%, 0.080%, 0.090%, 0.100%, 0.125%, 0.150%, 0.175%, 0.200%, 0.225%, 0.250%, 0.275%, 0.300%, 0.325%, 0.350%, 0.375%, 0.400%, 0.425%, 0.450%, 0.475%, 0.500%, 0.525%, 0.055%, 0.575%, 0.600%, 0.625%, 0.650%, 0.675%, 0.700%, 0.725%, 0.750%, 0.775%, 0.800%, 0.825%, 0.850%, 0.875%, 0.900%, 0.925%, 0.950%, 0.975%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, 999%, and/or 100%, or any range derivable therein.

Embodiments concern a patient who has symptoms of cancer, is asymptomatic of cancer, has a family or patient history of cancer, is at risk for cancer, or who has been diagnosed with cancer. A patient may be a mammalian patient though in most embodiments the patient is a human. The cancer may be malignant, benign, metastatic, or a precancer. It may be Stage I, II<III, or IV. It may be recurrent and/or chemo- or radiation-resistant. In still further embodiments, the cancer is melanoma, non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, cervical, gastrointestinal, lymphoma, brain, colon, sarcoma or bladder. The cancer may include a tumor comprised of tumor cells. Embodiments concern a patient who has symptoms of a particular disease or condition, is asymptomatic of a particular disease or condition, has a family or patient history of a disease or condition, is at risk for a disease or condition, or who has been diagnosed with the disease or condition.

In some embodiments, there are methods for treating cancer in a cancer patient comprising administering to the patient an effective amount of chemotherapy, radiation therapy, or immunotherapy (or a combination thereof) after the patient has been determined to have cancer based on methods disclosed herein. The point of origin of the cancer may be determined, in which case, the treatment is tailored to cancer of that origin. In some embodiments, tumor resection is performed as the treatment or may be part of the treatment with one of the other treatments. Examples of chemotherapeutics include, but are not limited to, the following: alkylating agents such as bifunctional alkylators (for example, cyclophosphamide, mechlorethamine, chlorambucil, melphalan) or monofunctional alkylators (for example, dacarbazine (DTIC), nitrosoureas, temozolomide (oral dacarbazine)); anthracyclines (for example, daunorubicin, doxorubicin, epirubicin, idarubicin, mitoxantrone, valrubicin; taxanes, which disrupt the cytoskeleton (for example, paclitaxel, docetaxel, abraxane, taxotere); epothilones; histone deacetylase inhibitors (for example, vorinostat, romidepsin); Topoisomerase I inhibitors (for example, irinotecan, topotecan); Topoisomerase II inhibitors (for example, etoposide, teniposide, tafluposide); kinase inhibitors (for example, bortezomib, erlotinib, gefitinib, imatinib, vemurafenib, vismodegib); nucleotide analogs and nucleotide precursor analogs (for example, azacitidine. azathioprine, capecitabine, cytarabine, doxifluridine. fluorouracil, gemcitabine, hydroxyurea, mercaptopurine, methotrexate, tioguanine (formerly thioguanine); peptide antibiotics (for examples, bleomycin, actinomycin); platinum-based antineoplastics (for example, carboplatin, cisplatin, oxaliplatin); retinoids (for example, retinoin, alitretinoin, bexarotene); and, vinca alkaloids (for example, vinblastine, vincristine, vindesine, vinorelbine). Immunotherapies include, but are not limited to, cellular therapy such as dendritic cell therapy (for example, involving chimeric antigen receptor); antibody therapy (for example, Alemtuzumab, Atezolizumab, Ipilimumab, Nivolumab, Ofatumumab, Pembrolizumab, Rituximab or other antibodies with the same target as one of these antibodies, such as CTLA-4, PD-1, PD-L1, or other checkpoint inhibitors); and, cytokine therapy (for example, interferon or interleukin).

In certain embodiments, there are methods of diagnosing a patient based on determining whether the patient has a methylation profile indicative of cancer or another disease or condition. In some embodiments, methods involve generating a methylation profile that indicates whether the patient has cancer or another disease or condition, and if so, from what organ. In certain embodiments, this is done using a biological sample from the patient that comprises cell free DNA.

Methods may further involve performing a biopsy, doing a CAT scan, doing a mammogram, performing ultrasound, or otherwise evaluating tissue suspected of being cancerous after determining the patient's methylation profile. In some embodiments, cancer that is found is classified in a cancer classification.

Cell free DNA (cfDNA) in plasma is a good target for detecting cancer, though it is not limited to detecting cancer. Plasma cfDNA includes DNA from both healthy cell and tumor cell. In general, in plasma cfDNA, the portion of cfDNA derived from tumor cells is much less than healthy cell. Thus, the challenge of using plasma cfDNA to detect cancer is how to accurately detect the very low amount of cfDNA derived from tumor cells.

Traditional DNA methylation analysis focuses on the methylation rate of an individual CpG site in a cell population. This rate, often called β-value, is the proportion of cells in which the CpG site is methylated. However, such population-average measures are not sensitive enough to capture an abnormal methylation signal with a small amount of cfDNAs from tumor cells. FIG. 1 is an example 100 of plasma cfDNA illustrating this point.

Example 100 includes a normal plasma cfDNAs with $\beta_{normal}=1$. The example 100 includes liver tumor-derived cfDNAs with $\beta_{tumor}=0$. The example 100 includes a plasma cfDNAs, which is a mixture of 99% normal plasma cfDNAs and 1% liver tumor-derived cfDNAs. Thus, the plasma cfDNAs has a $\beta_{mixed}=0.99$. Current technologies cannot reliably differentiate $\beta_{mixed}=0.99$ from $\beta_{normal}=1$.

The following embodiments of apparatuses and methods aim to provide solutions to the reliably detect small amount of tumor-derived cfDNAs, such as the example 100 in FIG. 1.

In one embodiment, a computer program product including a non-transitory computer-readable medium having instructions configured for detecting a cancer in a patient at a resolution of single reads, which, when executed by a processor of a computing system, cause the processor to perform the steps comprising: retrieving an N number of reads of the patient cell free DNA (cfDNA) methylation profile, N being a positive integer; identifying a J number of CpG clusters in the cfDNA methylation profile, J being a positive integer; retrieving a K number of DNA methylation markers of a cancer, K being a positive integer; determining the K number of marker regions in the cfDNA methylation profile, wherein the marker regions are the CpG clusters that correspond to the DNA methylation markers of the cancer; retrieving a T-class methylation pattern of each marker region, expressed as $m_k^T$, wherein m denotes marker region, T denotes T-class, k=1, 2, . . . K, the T-class methylation pattern is a methylation pattern derived from cfDNAs of tumor cells of the cancer; retrieving an N-class methylation pattern of each marker region, expressed as $m_k^N$, wherein m denotes marker region, N denotes N-class, k=1, 2, . . . K, wherein the N-class methylation pattern is a methylation pattern derived from cfDNAs of normal cells; and calculating a burden θ based on the N number of reads of the cfDNA methylation profile, the K number of $m_k^T$, and K number of $m_k^N$.

In another embodiment, there is an apparatus configured for detecting a cancer in a patient, comprising: a non-transitory memory; and a processor coupled to the non-transitory memory, the processor configured to execute steps of: retrieving an N number of reads of the patient cell free DNA (cfDNA) methylation profile, N being a positive integer; identifying a J number of CpG clusters in the cfDNA methylation profile, J being a positive integer; retrieving a K number of DNA methylation markers of a cancer, K being a positive integer; determining the K number of marker regions in the cfDNA methylation profile, wherein the marker regions are the CpG clusters that correspond to the DNA methylation markers of the cancer; retrieving a T-class methylation pattern of each marker region, expressed as $m_k^T$, wherein m denotes marker region, T denotes T-class, k=1,2, . . . K, the T-class methylation pattern is a methylation pattern derived from cfDNAs of tumor cells of the cancer; retrieving an N-class methylation pattern of each marker region, expressed as $m_k^N$, wherein m denotes marker region, N denotes N-class, k=1,2, . . . K, wherein the N-class methylation pattern is a methylation pattern derived from cfDNAs of normal cells; and calculating a burden θ based on the N number of reads of the cfDNA methylation profile, the K number of $m_k^T$, and K number of $m_k^N$. In some embodiments, the apparatus is portable.

In another embodiment, administering to the patient an effective amount of chemotherapy, radiation, or immunotherapy after the patient has been determined to have cancer based on a method comprising retrieving an N number of reads of the patient cell free DNA (cfDNA) methylation profile, N being a positive integer; identifying a J number of CpG clusters in the cfDNA methylation profile, J being a positive integer; retrieving a K number of DNA methylation markers of a cancer, K being a positive integer; determining the K number of marker regions in the cfDNA methylation profile, wherein the marker regions are the CpG clusters that correspond to the DNA methylation markers of the cancer; retrieving a T-class methylation pattern of each marker region, expressed as $m_k^T$, wherein m denotes marker region, T denotes T-class, k=1, 2, . . . K, the T-class methylation pattern is a methylation pattern derived from cfDNAs of tumor cells of the cancer; retrieving an N-class methylation pattern of each marker region, expressed as $m_k^N$, wherein m denotes marker region, N denotes N-class, k=1, 2, . . . K, wherein the N-class methylation pattern is a methylation pattern derived from cfDNAs of normal cells; and calculating a burden θ based on the N number of reads of the cfDNA methylation profile, the K number of $m_k^T$, and K number of $m_k^N$.

In another embodiment, a method for detecting a cancer in a patient based on a biological sample from the patient. In some embodiments, methods comprise using a computer program product that implements 1, 2, 3, 4, 5, 6 or more of the following steps: retrieving an N number of reads of the patient cell free DNA (cfDNA) methylation profile, N being a positive integer; identifying a J number of CpG clusters in the cfDNA methylation profile, J being a positive integer; retrieving a K number of DNA methylation markers of a cancer, K being a positive integer; determining the K number of marker regions in the cfDNA methylation profile, wherein the marker regions are the CpG clusters that correspond to the DNA methylation markers of the cancer; retrieving a T-class methylation pattern of each marker region, expressed as $m_k^T$, wherein m denotes marker region, T denotes T-class, k=1, 2, . . . K, the T-class methylation pattern is a methylation pattern derived from cfDNAs of tumor cells of the cancer; retrieving an N-class methylation pattern of each marker region, expressed as $m_k^N$, wherein m denotes marker region, N denotes N-class, k=1, 2, . . . K, wherein the N-class methylation pattern is a methylation pattern derived from cfDNAs of normal cells; and calculating a burden θ based on the N number of reads of the cfDNA methylation profile, the K number of $m_k^T$, and K number of $m_k^N$.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the concepts and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

In still further embodiments, the cancer is melanoma, or a cancerous cells that are or are from non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, cervical, gastrointestinal, lymphoma, brain, colon, sarcoma or bladder. The cancer may include a tumor comprised of tumor cells.

In some embodiments, there are methods for treating cancer in a cancer patient comprising administering to the patient an effective amount of chemotherapy, radiation therapy, or immunotherapy (or a combination thereof) after the patient has been determined to have cancer based on methods disclosed herein. The point of origin of the cancer may be determined, in which case, the treatment is tailored to cancer of that origin. In some embodiments, tumor resection is performed as the treatment or may be part of the treatment with one of the other treatments.

In certain embodiments, there are methods of diagnosing a patient based on determining whether the patient has a methylation profile indicative of cancer. In some embodiments, methods involve generating a methylation profile that indicates whether the patient has cancer, and if so, from what organ. In certain embodiments, this is done using a biological sample from the patient that comprises cell free DNA.

Methods may further involve performing a biopsy, doing a CAT scan, doing a mammogram, performing ultrasound, or otherwise evaluating tissue suspected of being cancerous after determining the patient's methylation profile. In some embodiments, cancer that is found is classified in a cancer classification. Cancer classifications may be qualified as any of Stages I, II, III, or IV.

In some embodiments, methods may also involve comparing a measured value to a control that is indicative of a relevant noncancerous tissue or of relevant cancerous tissue. In certain embodiments, a measured value is compared to predetermined threshold value. In some embodiments, that certain level or a predetermined threshold value is at, below, or above 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percentile, or any range derivable therein. Moreover, the value or control may be based on at least or at most 10, 20, 30, 40, 50, 60, 70, 80, 90, 100, 150, 200, 300, 400, 500 or more patients (or any range derivable therein).

In one aspect, provided herein is a computer program product comprising a computer-readable medium having computer program logic recorded thereon arranged to put into effect the method of an embodiment disclosed herein.

It is contemplated that any embodiment discussed in this specification can be implemented with respect to any method, system, kit, computer-readable medium, or apparatus of the invention, and vice versa. Furthermore, apparatuses of the invention can be used to achieve methods of the invention. Moreover, it is specifically contemplated that any embodiment discussed herein may be specifically excluded.

It will be understood by one of skill in the art that the embodiments disclosed herein can be combined in any combination.

BRIEF DESCRIPTION OF THE DRAWINGS

Those of skill in the art will understand that the drawings, described below, are for illustrative purposes only. The drawings are not intended to limit the scope of the present teachings in any way.

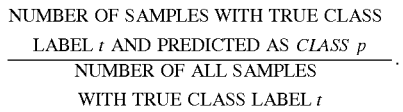

Figure 10:
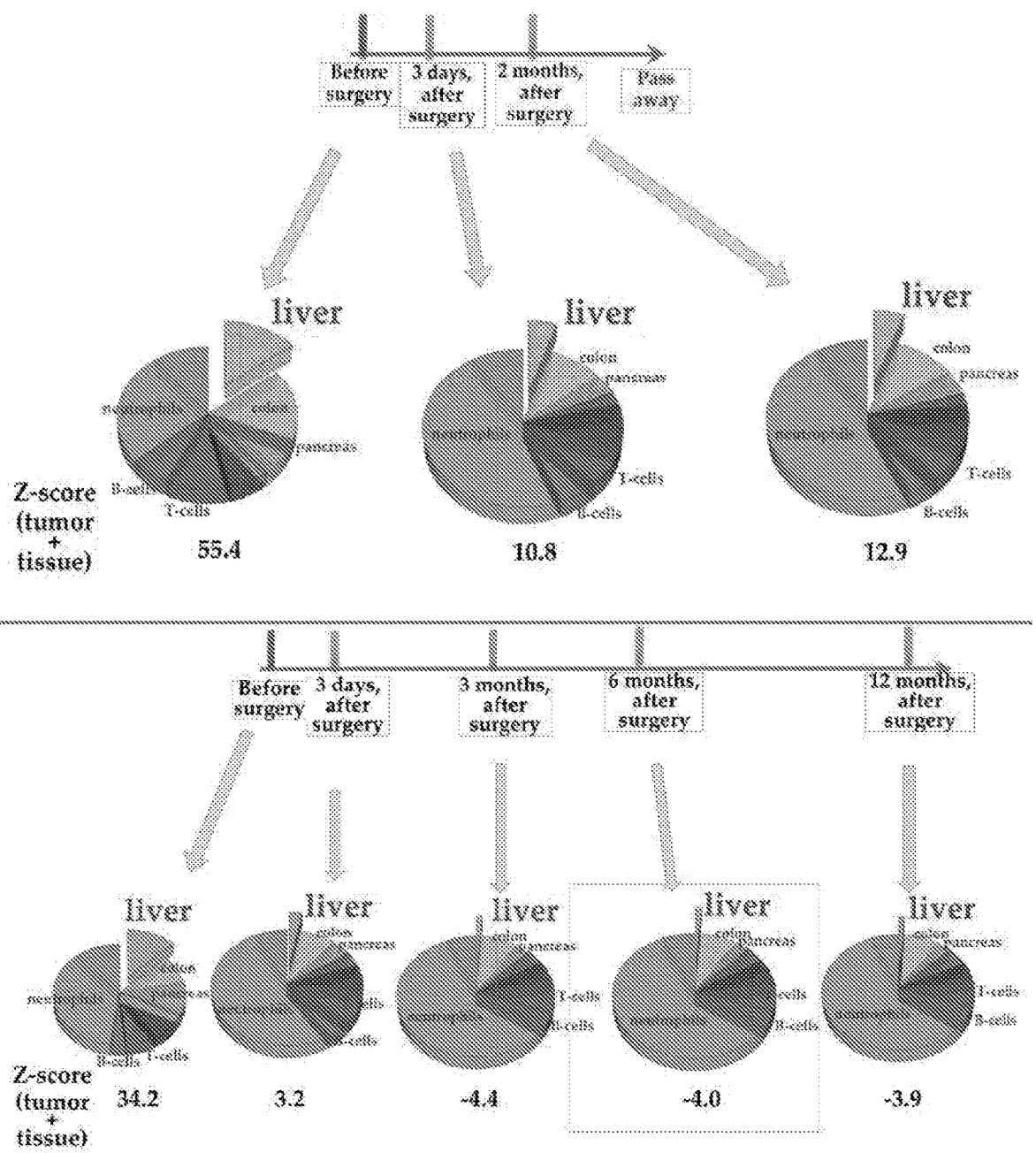

FIG. 10 depicts an exemplary embodiment, illustrating analysis of two liver cancer patients before and at multiple time points after surgical resection. The pie chart at each time point for two cancer patients is the composition of 14 tissues: A for Patient 1 and B for Patient 2. C lists the Z-score values of Patient 1 and Patient 2.

Figures 10, 11:
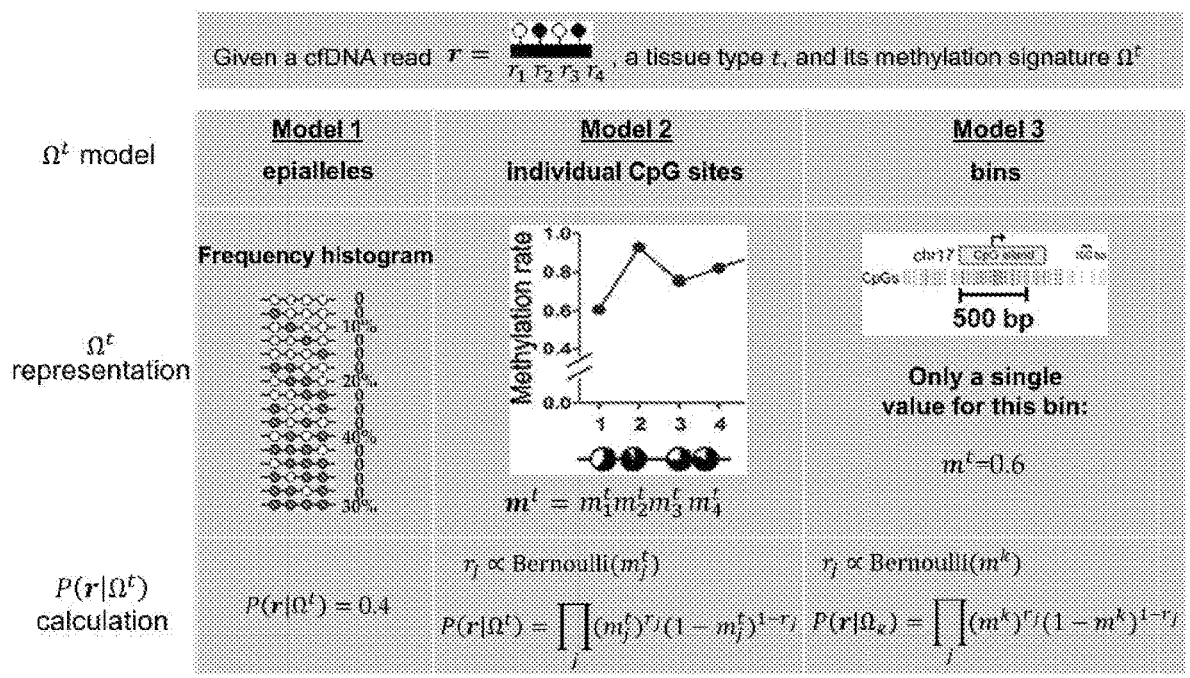

FIG. 11 depicts an exemplary embodiment, illustrating three models for characterizing DNA methylation pattern based on individual value of a tissue sample. Three models can be used for characterizing methylation signature at different resolutions (from high to low): (model 1) epialleles, (model 2) CpG sites, and (model 3) bins.

Figure 12:
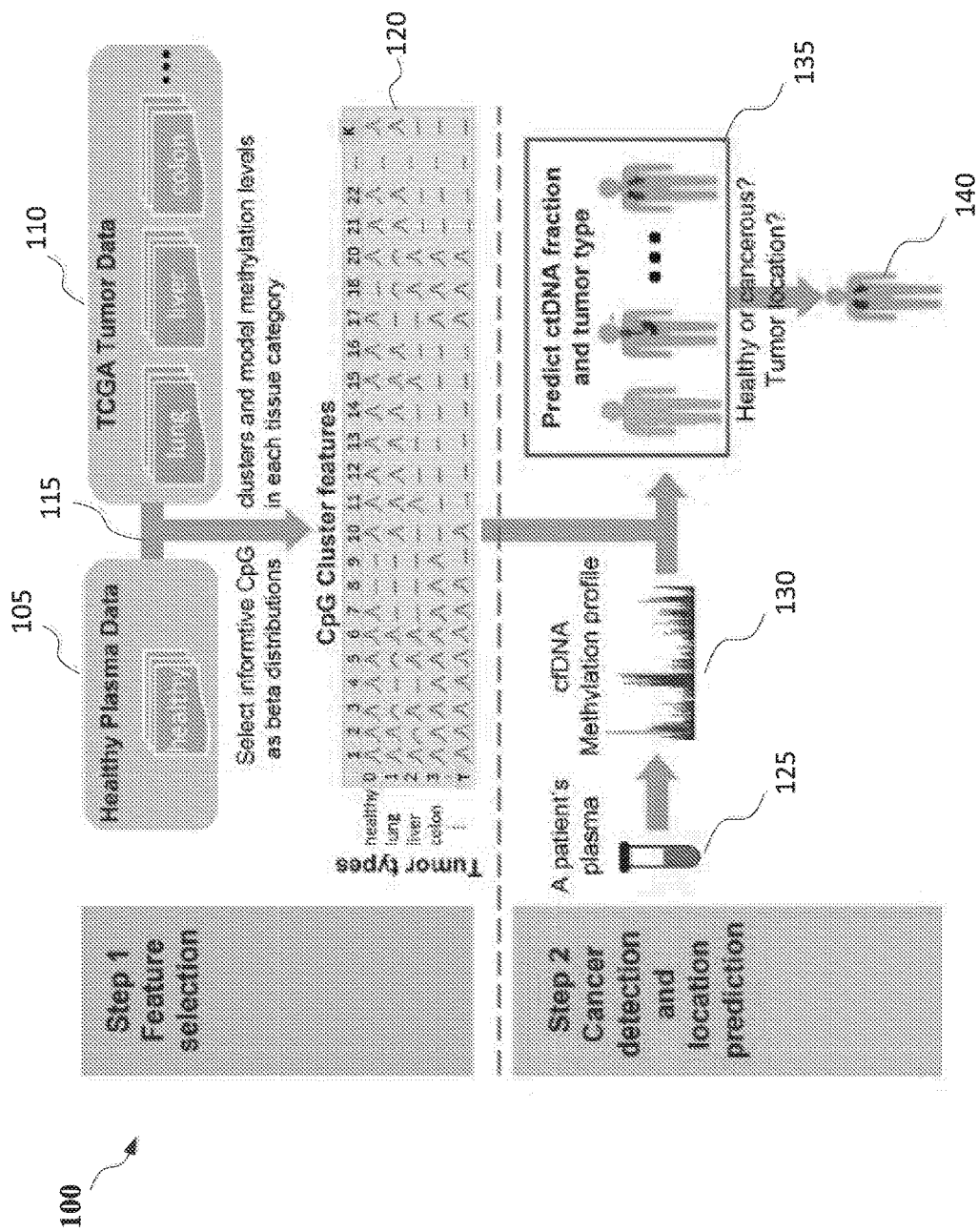

FIG. 12 is a flow chart of a method for screening cancer and identifying tissue-of-origin of a tumor, according to one embodiment.

Figure 13:
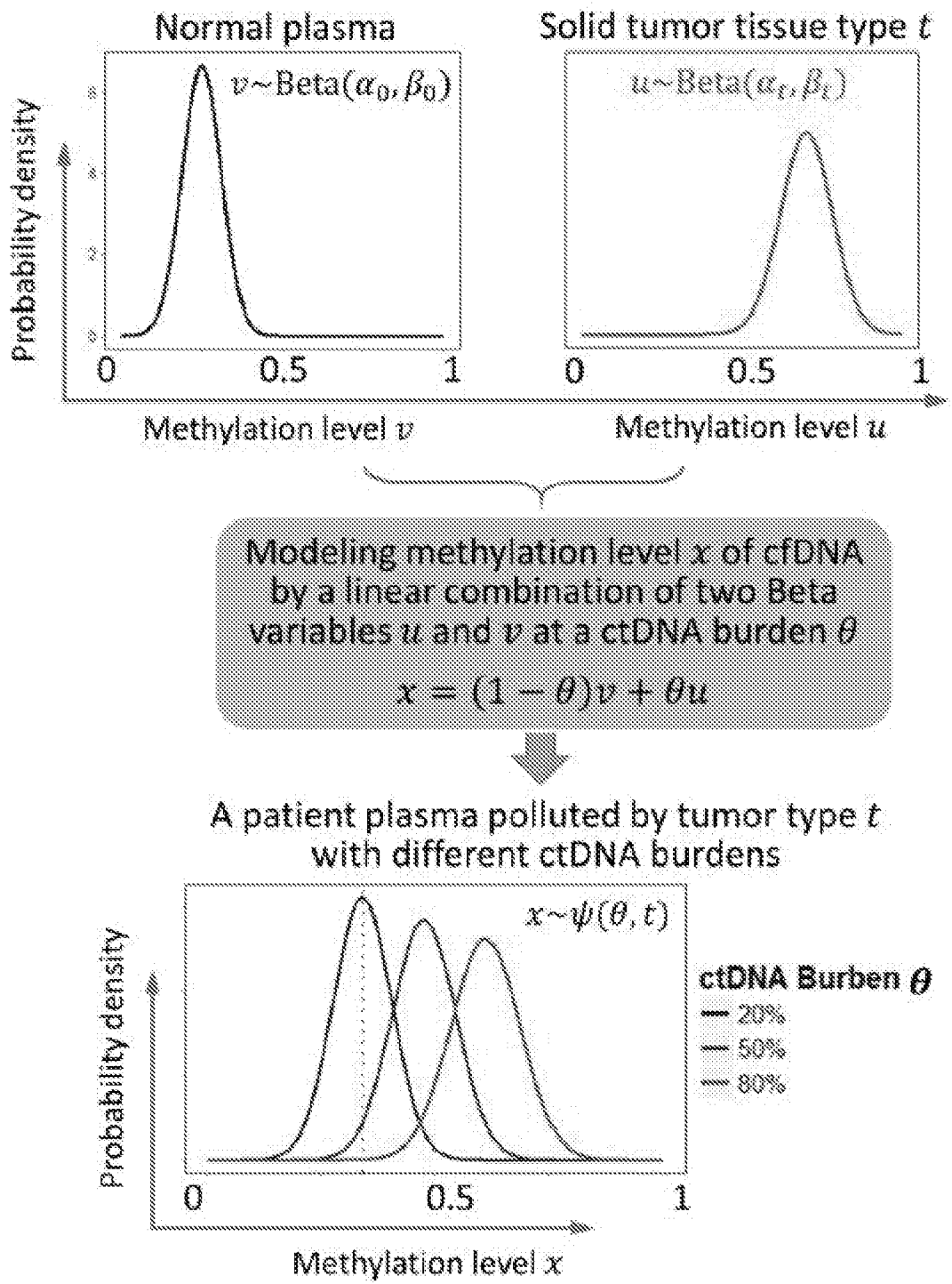

FIG. 13 is a mixture model of methylation level (x) in a patient's plasma cfDNA, for different burdens of ctDNAs from the tumor type t, according to one embodiment.

Figure 14A:
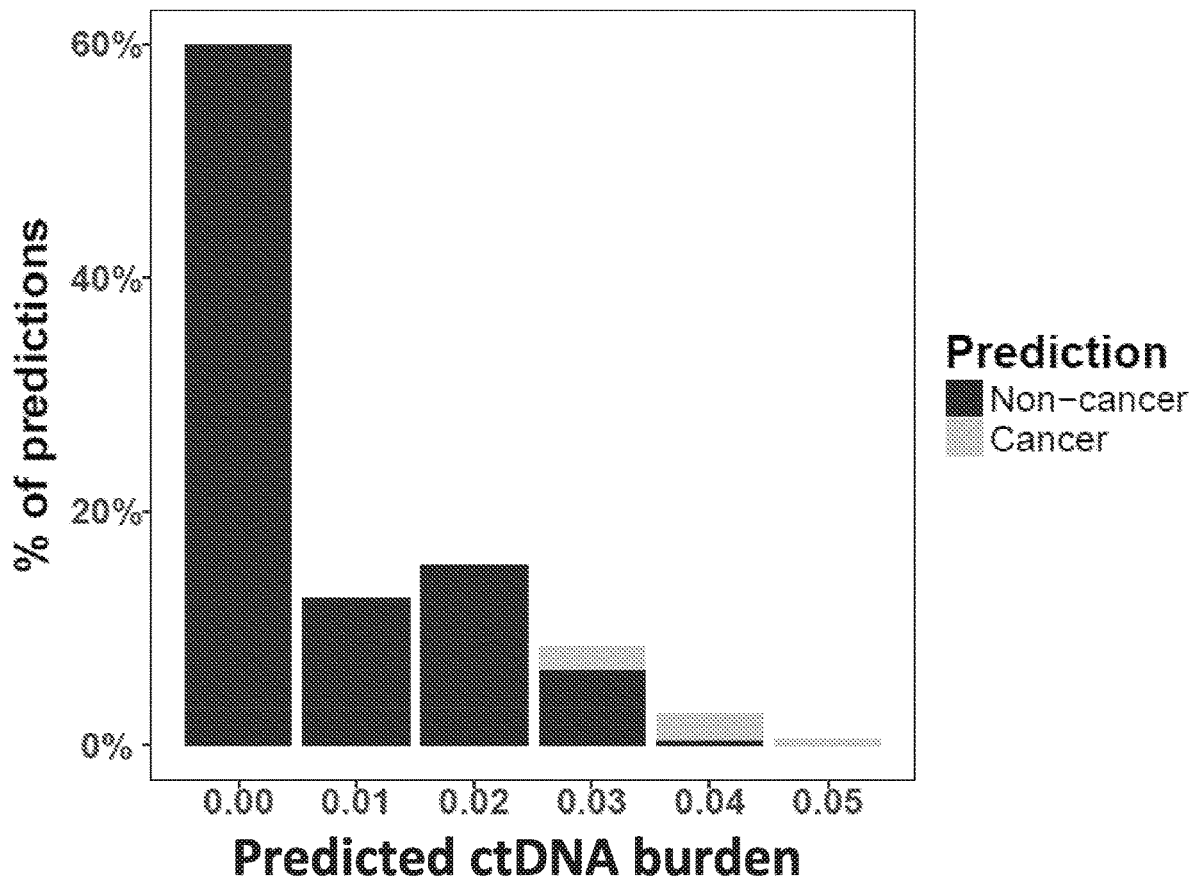
Figure 14B:
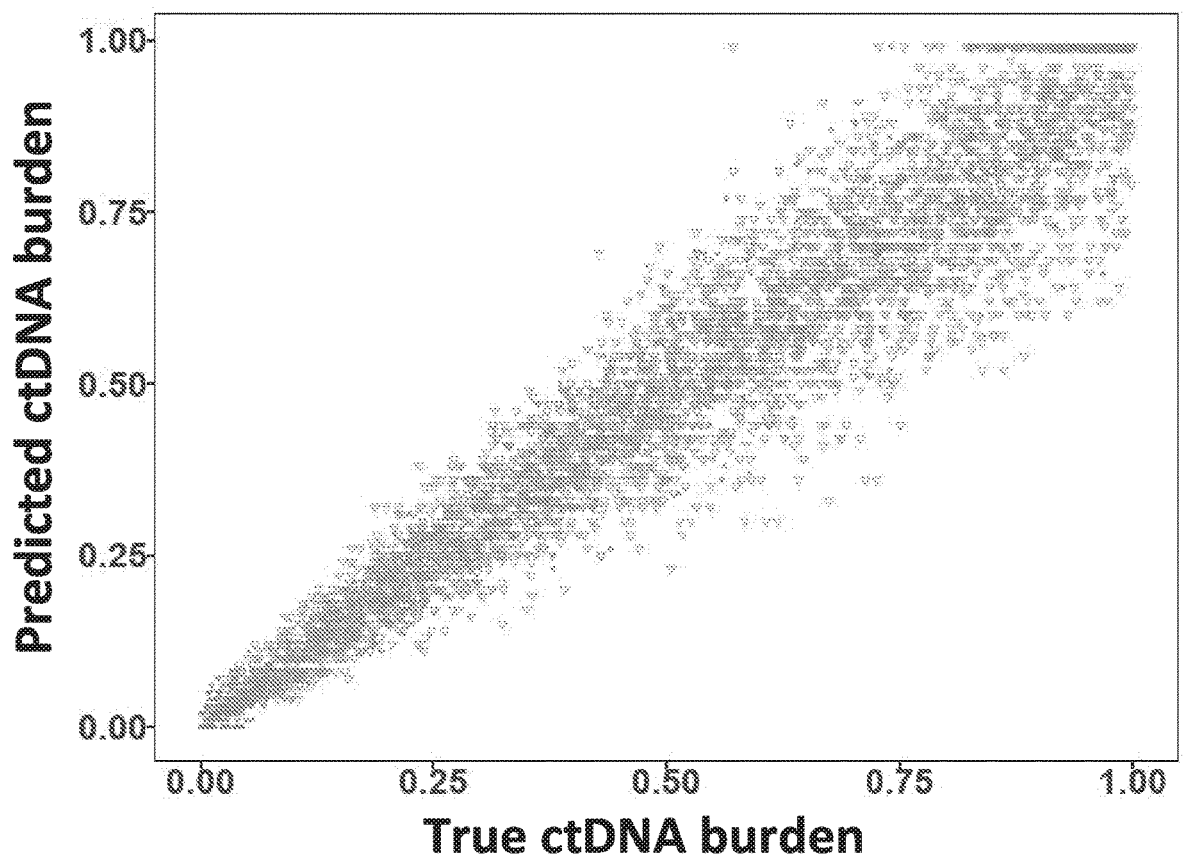

FIG. 14A-B. A is a histogram of predicted ctDNA burdens for normal samples, according to one embodiment. B is a comparison of predicted and true ctDNA burdens for cancer samples, according to one embodiment.

Figure 15:
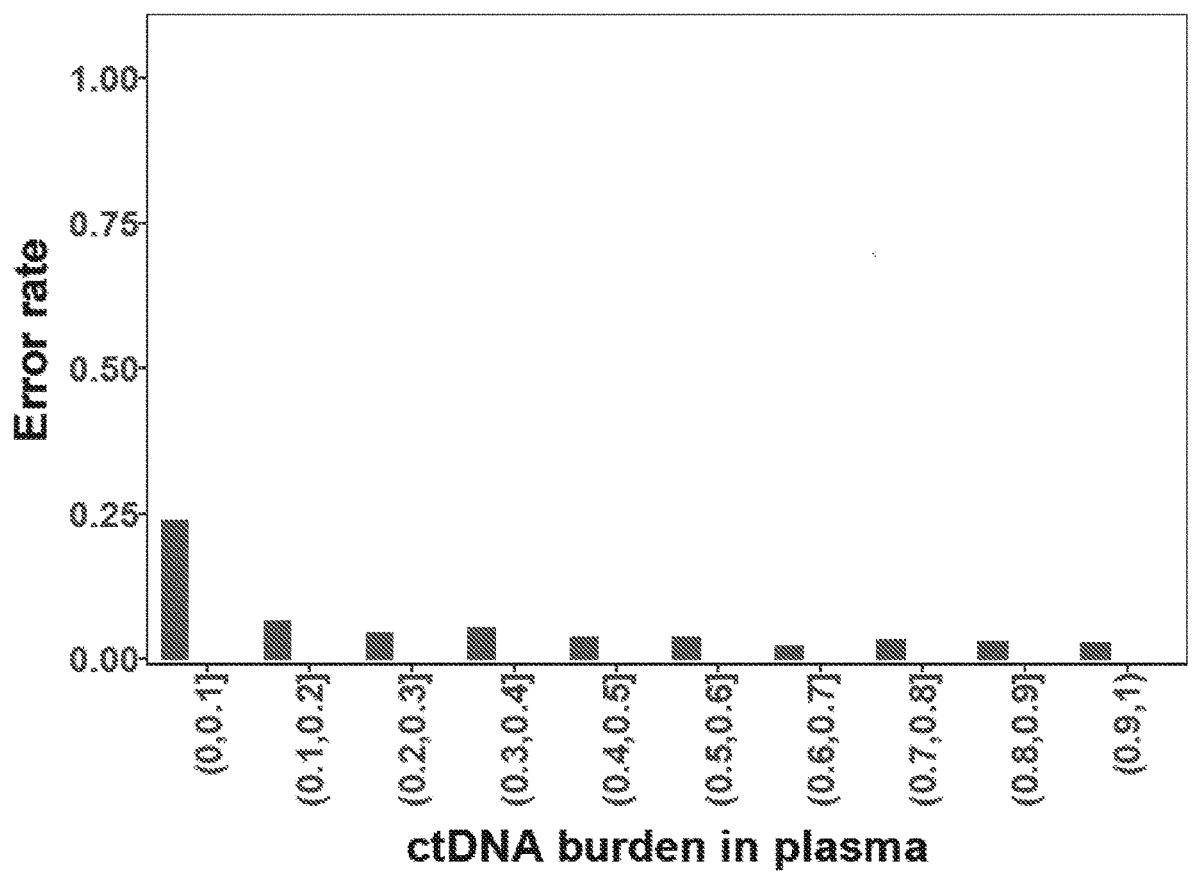

FIG. 15 is a bar chart showing the prediction performance of an embodiment of the disclosure.

Figure 16:
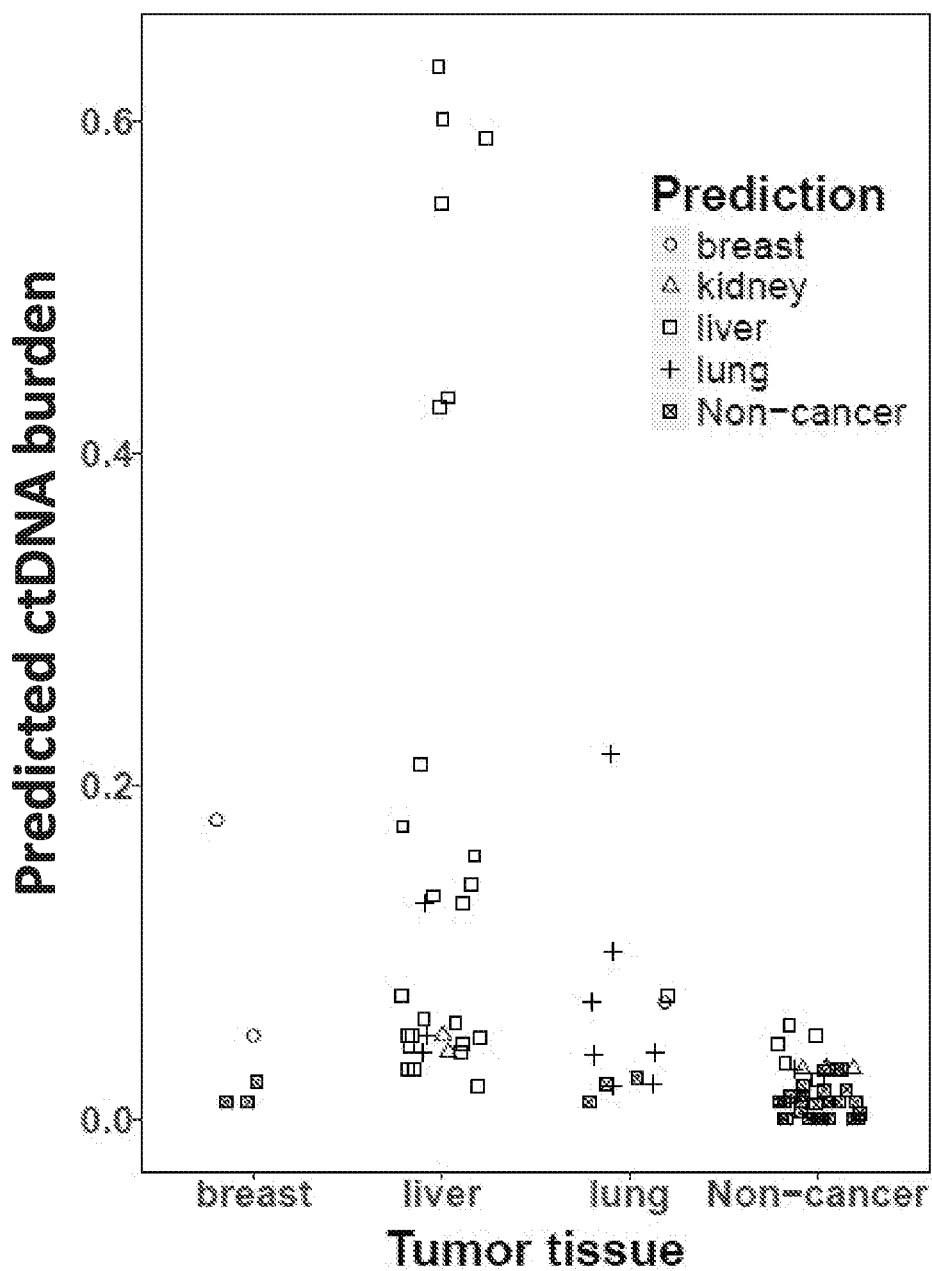

FIG. 16 is a relationship between ctDNA burden and tumor tissue prediction for each plasma of the real data according to one embodiment of the disclosure.

Figure 17:
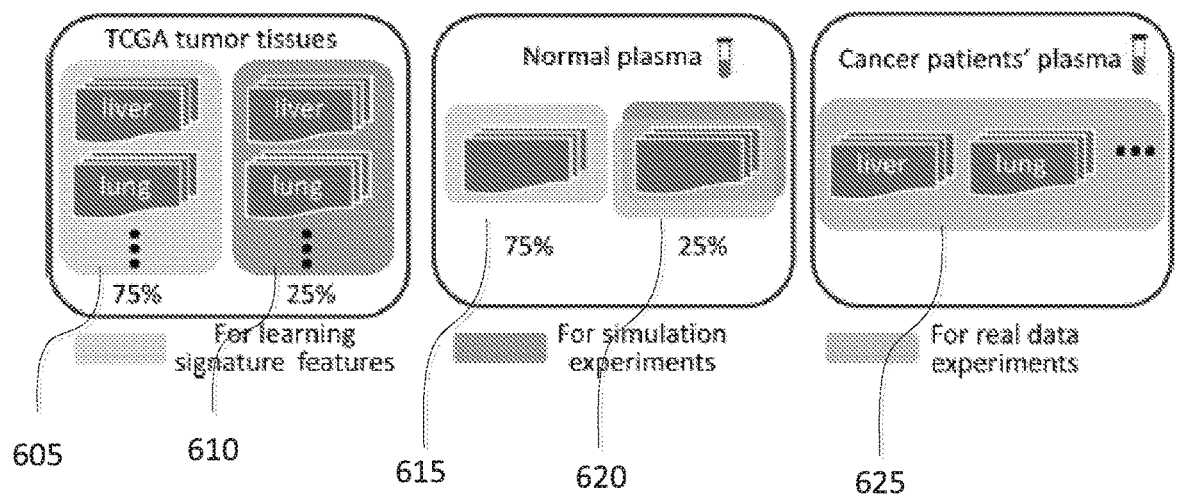

FIG. 17 illustrates the data partition for learning discriminating features, in both simulation experiments and real data experiments according to one embodiment of the disclosure.

Figure 18:
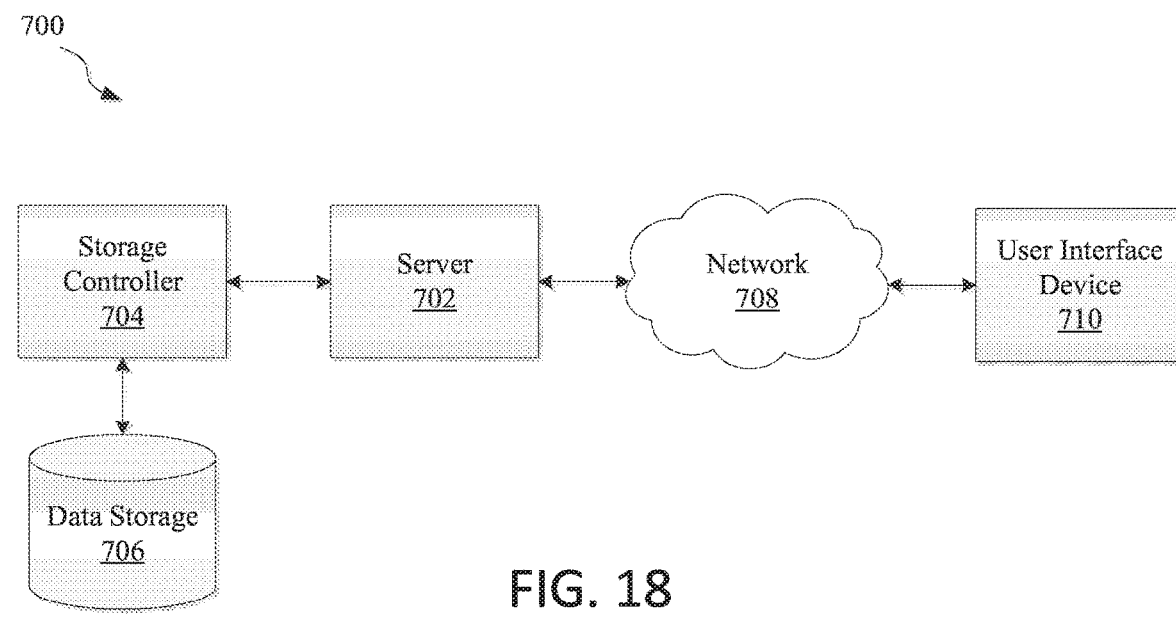

FIG. 18 illustrates a computer system for obtaining access to database files for detecting cancer and identifying tissue-of-origin according to one embodiment of the disclosure.

Figure 19:
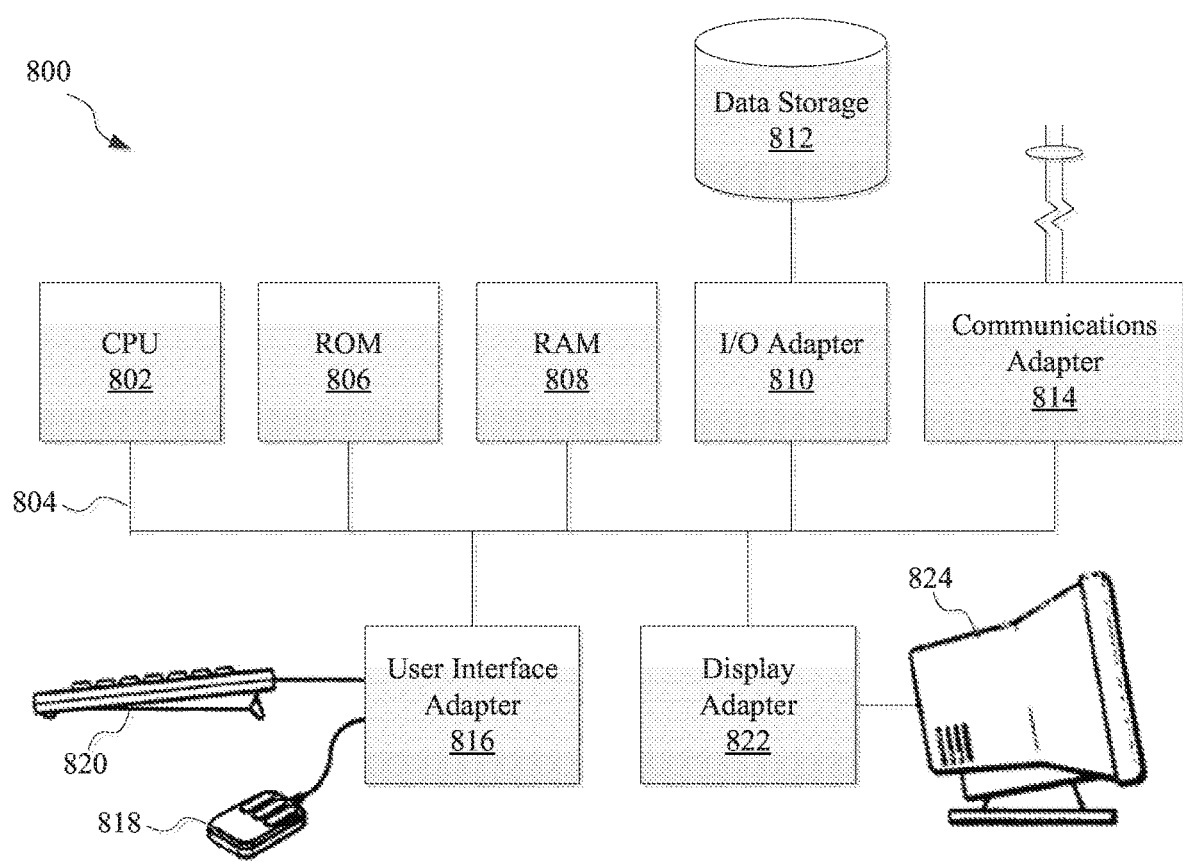

FIG. 19 illustrates a computer system configured for cancer detection and tissue-of-origin identification according to one embodiment of the disclosure.

Figure 20:
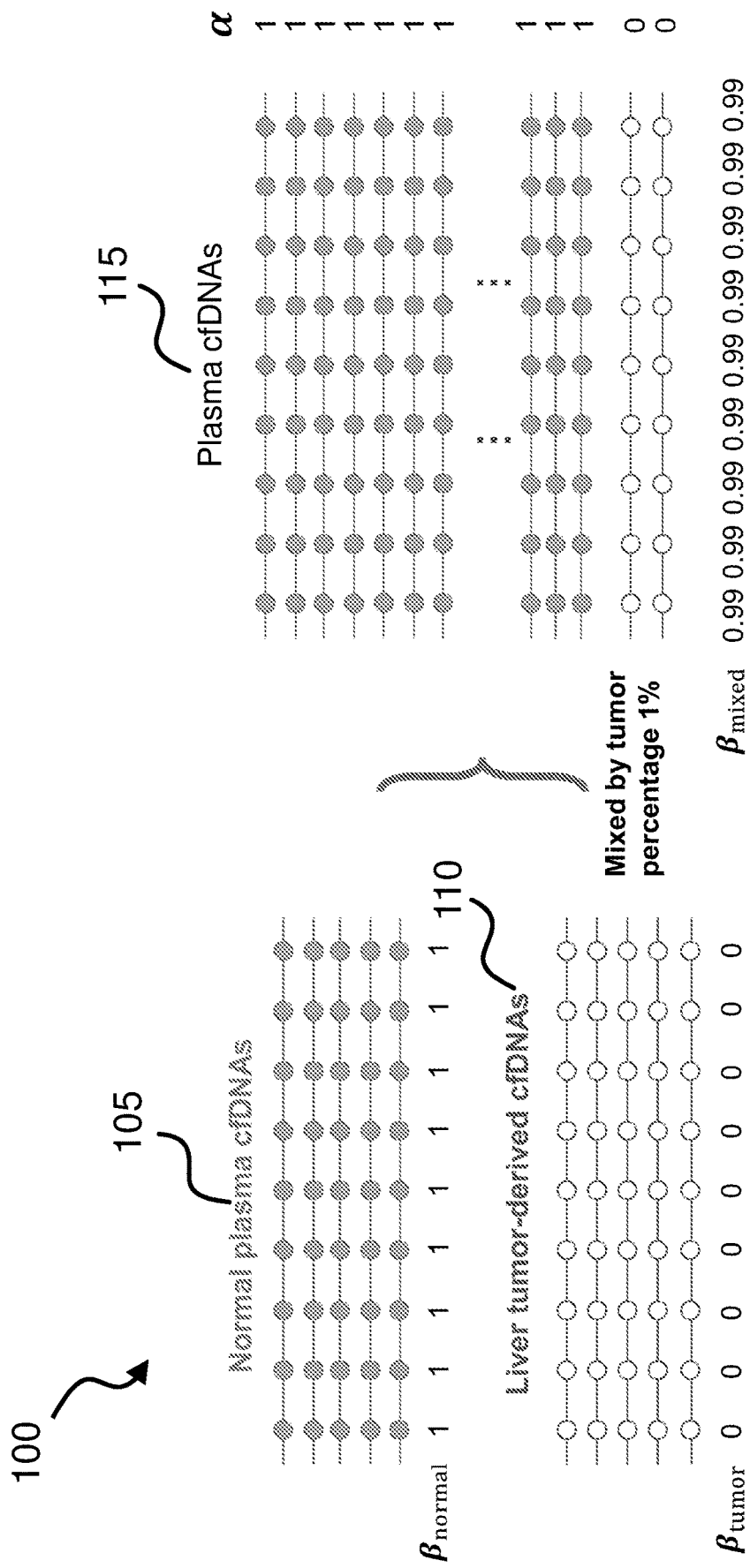

FIG. 20 Illustration of the rationale why the methylation value averaged across all CpG sites in a sequencing read ($\alpha$-value) is more sensitive at detecting tumor-derived cfD-NAs than the traditional methylation level of a CpG site averaged across all reads ($\beta$-value). Each line represents a sequencing read and each dot represents a CpG site.

Figure 21:
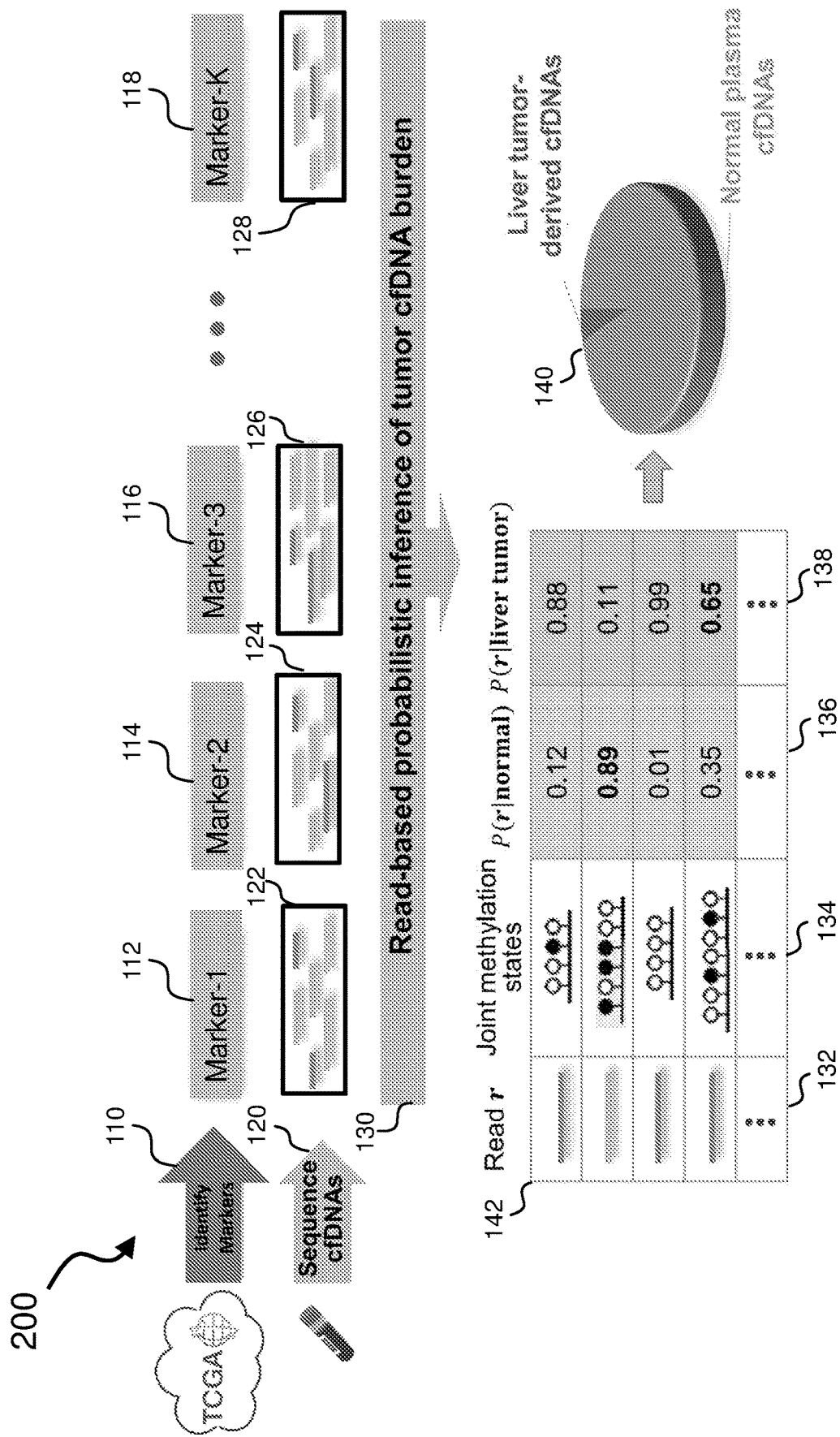

FIG. 21 Overview of the CancerDetector method. The color of cfDNA sequencing reads represents their origin: red (green) reads are from tumor (normal plasma) cfDNA fragments.

Figure 22:
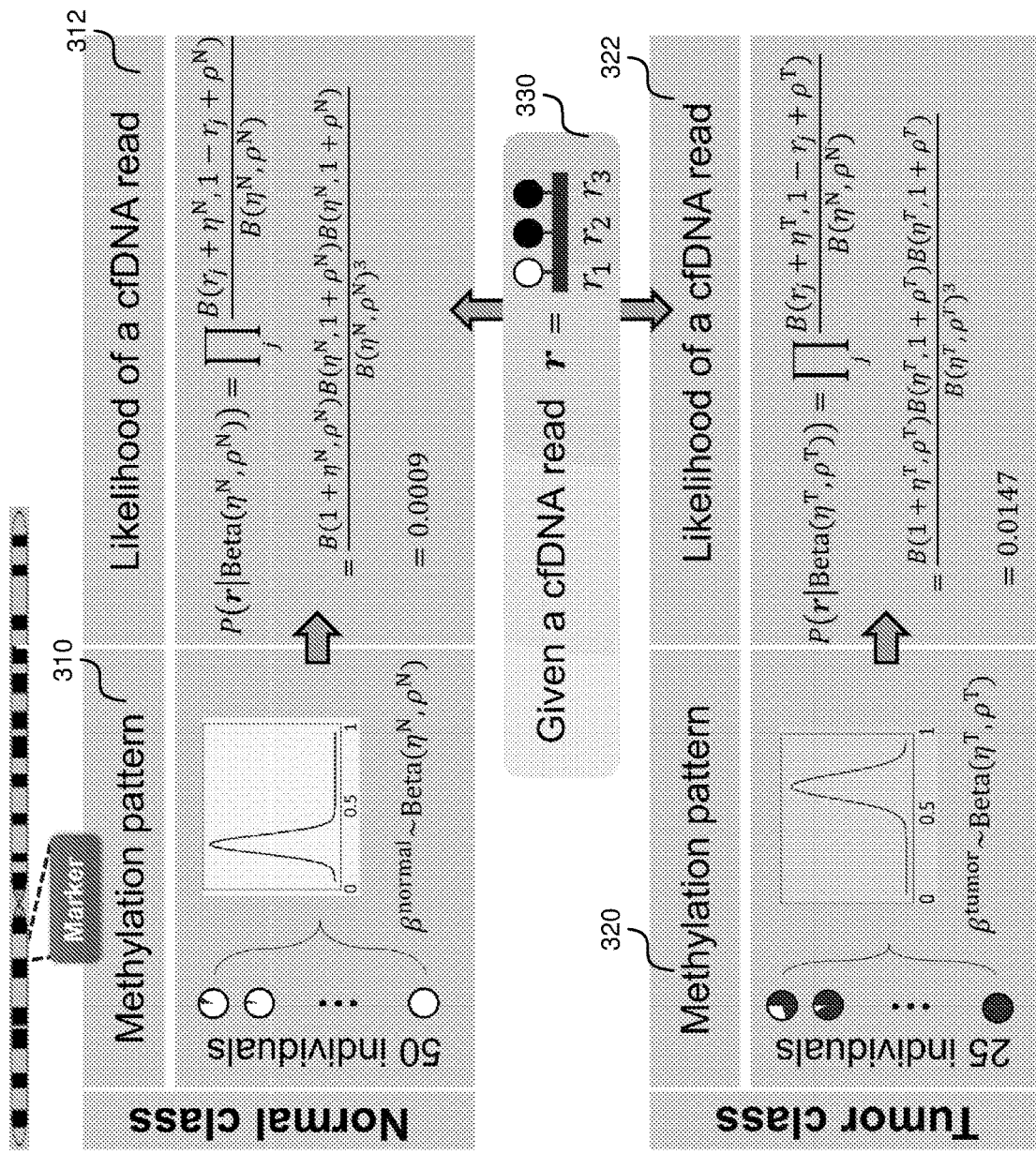

FIG. 22 Illustration of calculating the likelihood of a cfDNA sequencing read in a marker, given the methylation patterns of normal and tumor classes.

Figure 23:
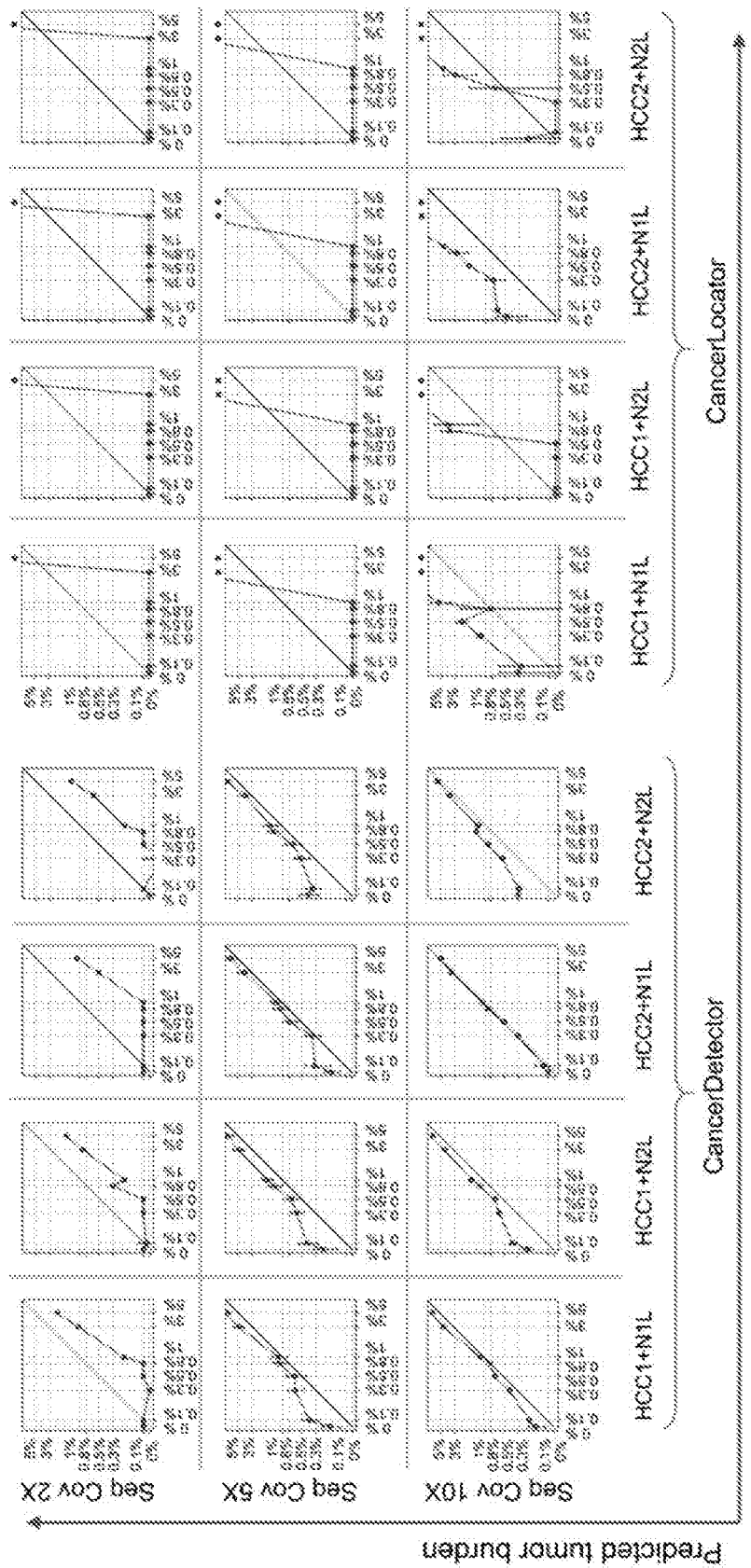

FIG. 23 Predicted blood tumor burdens (averaged over 10 runs) for the liver cancer cfDNA samples, simulated by subsampling and mixing sequencing reads from a real healthy cfDNA sample (N1L or N2L) and a solid liver tumor sample (HCC1 or HCC2) at 8 different tumor burdens: 0, 0.1%, 0.3%, 0.5%, 0.8%, 1%, 3%, 5%, and at 3 different sequencing coverages (2×, 5×, and 10×). In each log-log plot, a blue point represents a simulated sample with error bars (standard deviation of predicted tumor burden), the x-axis is its true tumor burden and the y-axis is its predicted tumor burden. When the predicted tumor burden is out of range (>5%), we draw the point above the box.

Figure 24:
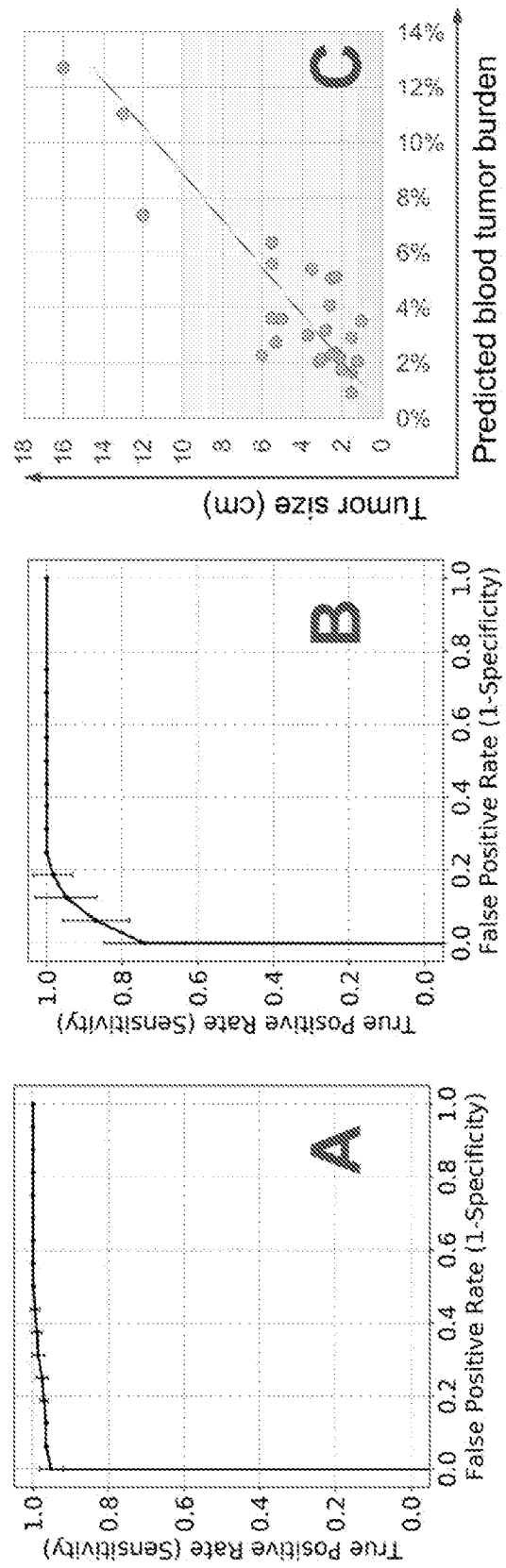

FIG. 24 Predicted blood tumor burdens for the real data in all 10 runs: (A) average ROC curve with standard deviation bars for CancerDetector, (B) average ROC curve with standard deviation bars for our previous method CancerLocator, and (C) the relationship between the tumor size and average blood tumor burden predicted by CancerDetector.

Figure 25:
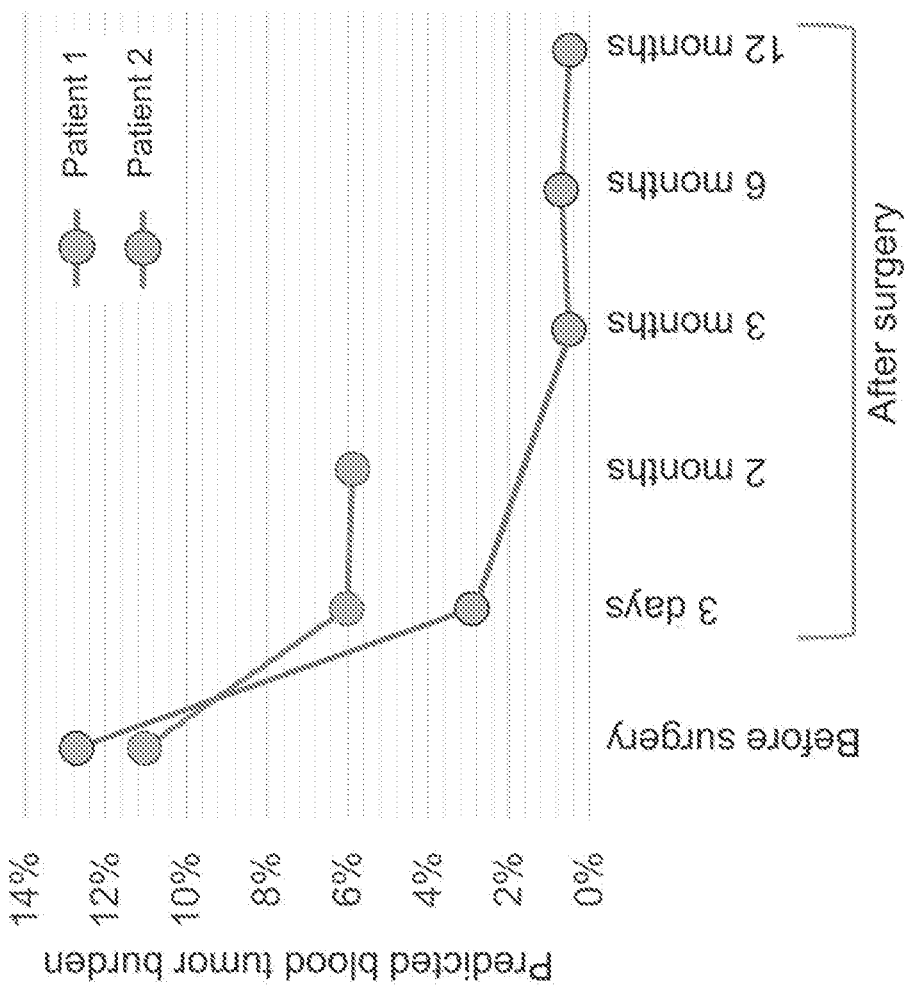

FIG. 25 Average predicted blood tumor burdens for longitudinal data of two liver cancer patients before and after tumor resections in all 10 runs. The $2^{nd}$ patient passed away after surgery.

DETAILED DESCRIPTION OF EMBODIMENTS

Definitions

Unless otherwise noted, terms are to be understood according to conventional usage by those of ordinary skill in the relevant art.

In one aspect, disclosed herein are methods for disease diagnosis based on sequencing data (e.g., nucleic acid) from blood samples. As disclosed herein, sequencing data include information concerning cfDNA, cell-free microRNA, and immune repertoire sequencing. cfDNA is used throughout the application as the main example but it should not in any way limit the scope of the invention.

In one aspect, disclosed herein are methods and systems for establishing libraries of sequencing signatures (e.g., methylation signatures) based on existing sequencing methylation data (e.g., both array-based and conventional non-array based sequencing data). All suitable existing sequencing methylation data can be used here, including, for example, cfDNA, cell-free microRNA, and immune repertoire sequencing data. In some embodiments, the sequencing data can be disease specific (e.g., cancer specific) and/or tissue specific.

In one aspect, methods provided can also be used to identify tissue type and predict cancer prognosis and patient survival. Here, cfDNA is obtained from blood samples via minimally invasive procedures. In some embodiments, sequencing data from the cfDNA samples comprise sequencing reads each including a consecutive sequence of nucleic acids. In some embodiments, sequencing data from the cfDNA samples further comprise methylation status of selected sequences within the consecutive sequence. As disclosed herein, methylation status includes both the presence and absence of methylation modification at nucleic acid sites.

In one aspect, methods disclosed herein can also be used to monitor cancer treatment for identifying driver clones, driver genes and driver regulatory pathways.

In one aspect, methods provided can also be used to identify the composition of tissue types in plasma cfDNA and predict cancer diagnosis and prognosis, and identify the tumor type that a patient is likely to get.

Figure 1:
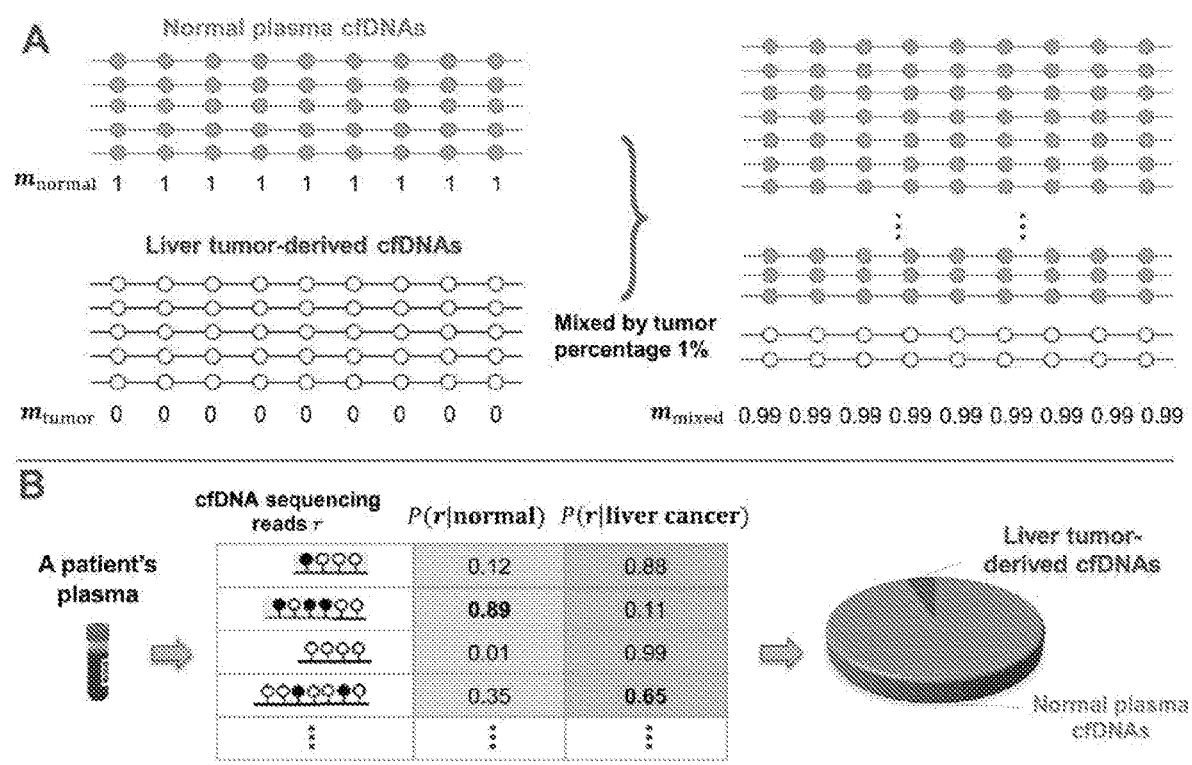
FIG. 1 depicts an exemplary embodiment, illustrating (A) the rationale of how "phased" methylation pattern based analysis is more sensitive for detecting tumor-derived cfDNAs than the analysis based on average methylation rates of individual CpG sites; and (B) the rationale of how "phased" methylation analysis can be naturally used for inferring cfDNAs composition. Filled circles indicate methylated sites and empty circles indicate un-methylated sites.

Among all plasma cfDNAs based cancer diagnosis methods, cfDNA methylation alterations have attracted a lot of research interests, because (i) methylation alterations are hypothesized to be early carcinogenesis mechanism in literatures and thus be potentially early cancer indicators, and (ii) a large amount of aberrant genome-wide DNA methylation patterns are observed in plasma cfDNAs in recent studies. Almost all existing cfDNA-based methylation analysis methods are based on the measurements of average methylation rates over individual CpG sites or genomic regions. The CpG sites or CG sites are regions of DNA where a cytosine nucleotide is followed by a guanine nucleotide in the linear sequence of bases along its 5' to 3' direction. CpG is shorthand for 5'-C-phosphate-G-3', that is, cytosine and guanine separated by only one phosphate; phosphate links any two nucleosides together in DNA. As shown in the toy example of FIG. 1A (taking liver tumor as example), however, the average methylation rates overlook the mixture nature of cfDNAs, by which the true cancer signals (tumor-derived cfDNAs or ctDNAs) are overwhelmed by normal plasma cfDNAs. Therefore, for early cancer stage with a small fraction of ctDNAs, the average methylation rates of individual CpG sites in a mixed cfDNAs, e.g., $m_{mixed}=0.99$ in FIG. 1A, have negligible difference from those of normal plasma cfDNAs, $m_{normal}=1$. Considering measurement errors and biases, this fact often makes existing methods fail to sensitively detect tumor signals for early cancer patients. However, when we investigate each individual cfDNA fragment (that can be captured by methylation sequencing reads), the tumor-derived cfDNA fragments can be easily distinguished from normal plasma cfDNA fragments, although ctDNA fraction in plasma is only 1%. The rationale is depicted in FIGS. 1A and 1B.

The coincidence of methylation status of multiple adjacent CpG sites over an individual cfDNA fragment actually is the so-called "phased" methylation pattern of individual cfDNA fragments or "epialleles" in literature. In this study, we hypothesize that the "phased" methylation pattern on individual cfDNA fragments are more sensitive than average methylation rates of individual CpG sites or genomic bins. There have been several recent studies realizing the sensitivity of "phased" methylation patterns in solid tumor samples for clonal evolution and intra-tumor phylogenies and purification. So far, none studies applied "phased" methylation patterns to cfDNA-based cancer diagnosis. We are therefore the first to propose the "phased" cfDNA methylation analysis for cancer diagnosis. The genome-wide methylation sequencing of cfDNAs, e.g., whole-genome bisulfite sequencing (WGBS) or reduced representation bisulfite sequencing (RRBS), provides abundant "phased" methylation data for fueling our "phased" analysis method. That is, sequencing reads of WGBS or RRBS covering at least 3 CpG sites are "phased" methylation data. FIG. 1A actually reveals an intuitive "phased" methylation analysis method: we can label each cfDNA read which source it is likely to come from (normal plasma or liver tumor), then infer the fraction of those reads most likely from liver tumor among all cfDNA reads. This is indeed a cfDNA reads categorization and two-class composition inference process, as formally illustrated in FIG. 1B. As a result, the elevated fraction of liver tumor derived cfDNA reads can imply the risk of getting liver cancer for a patient. If we repeat this process for other cancer types, we can not only determine if a patient gets a cancer or not, but also predict which cancer type the patient may get. The latter prediction can be made by choosing the cancer type which has the most abnormally elevated fraction in plasma cfDNAs.

Figure 2:
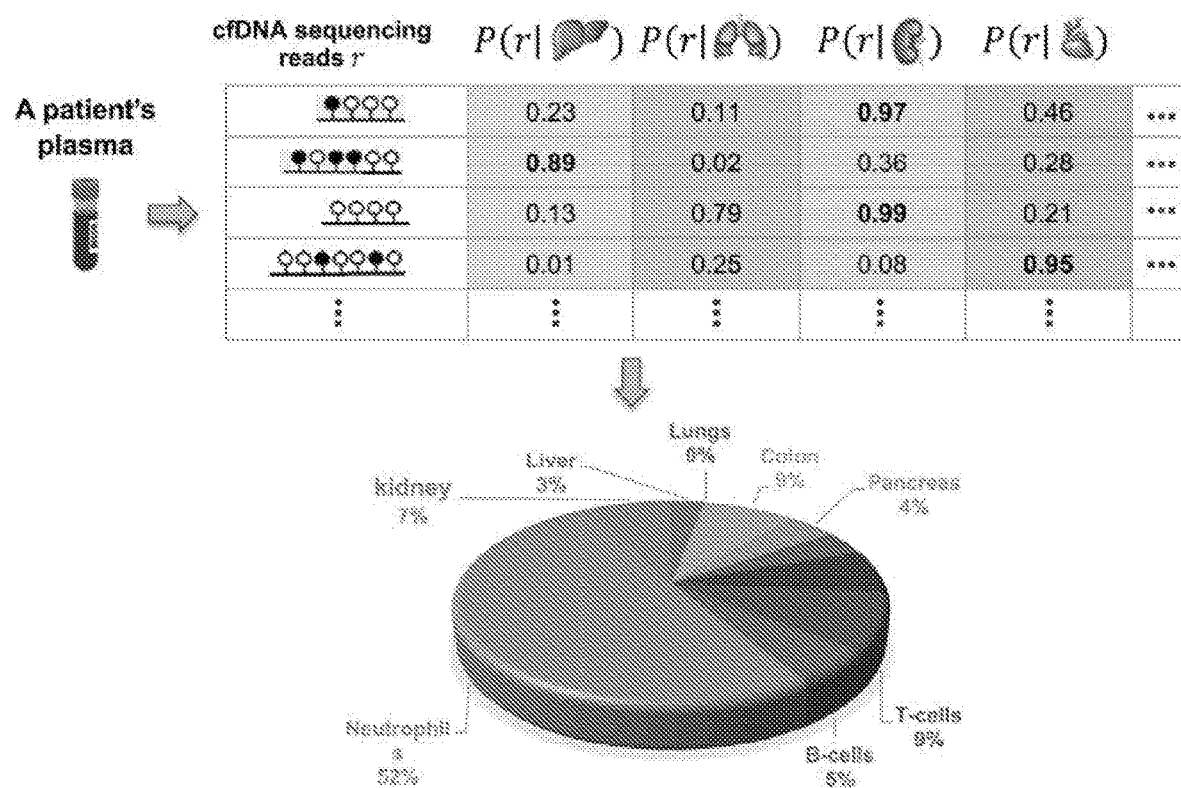
FIG. 2 depicts an exemplary embodiment, illustrating the likelihood of identifying tissue-of-origin of cfDNA sequencing reads and their use for inferring normal tissue composition of plasma cfDNAs.

More than de-convoluting cfDNAs into two classes (normal plasma and a specific tumor type), the fact that plasma cfDNAs are mixture of DNAs released from normal tissues of various organs, reminds us another different process: de-convoluting cfDNAs into a composition of multiple normal tissue types. This is a process of tissue-of-origin identification and tissue composition inference. Methylation data is ideal for this process because previous studies provided rich evidences that methylation patterns have abundant tissue-specific biomarkers4. As shown in FIG. 2, we follow the same procedure as above: first identifying the tissue-of-origin likelihood of each cfDNA read, then inferring the tissue composition of plasma cfDNAs. Sun et al. (2015) have demonstrated the most abnormally elevated tissue fraction of plasma cfDNAs can be used as the evidence for cancer type prediction4, although their method is based on the average methylation rates of genomic regions, not on "phased" methylation data.

The above two different "phased" methylation pattern based cfDNA analyses explore the limited tumor signals overwhelmed in massive tumor-irrelevant cfDNAs from different biological dimensions and based on different genome regions. Our results showed that there is very little overlap (8%) between genomic regions of cancer-specific and tissue-specific methylation patterns. Therefore, this observation leads to the integration of these two non-overlapping analyses for jointly making decision of cancer diagnosis. In this work, we propose to perform the integrative analysis of "phased" cfDNA methylation for noninvasive cancer diagnosis.

Overall Process

Figure 3:
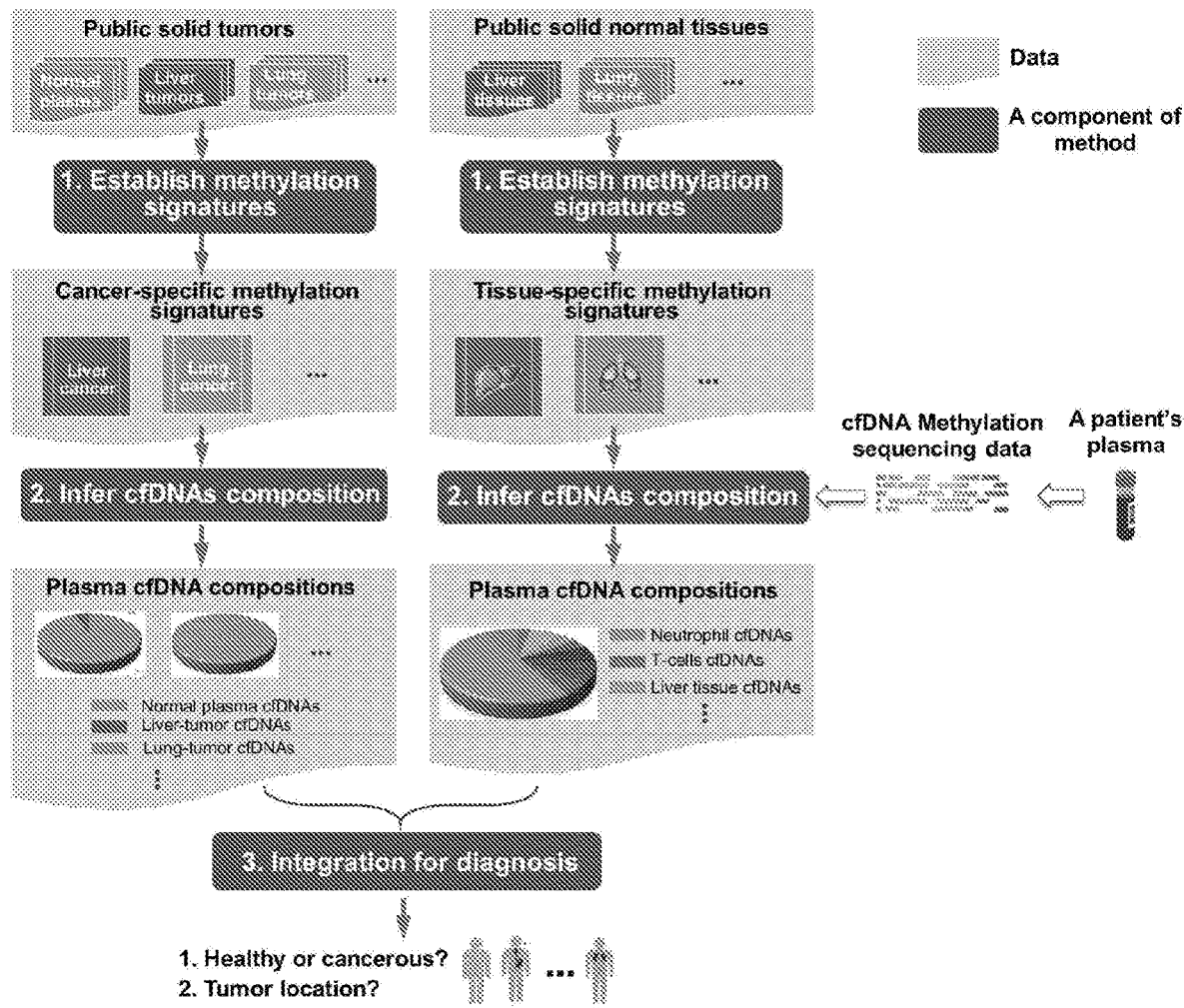
FIG. 3 depicts an exemplary embodiment, illustrating integrative analysis of "phased" cfDNA methylation. The black boxes with white text are components of the method, and the gray boxes are data.

An exemplary overview of the integrative analysis of "phased" cfDNA methylation is illustrated in FIG. 3. There are three components in this method: (i) establishing methylation signatures from public methylation data, (ii) a probabilistic framework of inferring cfDNAs composition, and (iii) integration method for cancer diagnosis. Processes can be established for determining tissue composition and tumor composition in the cfDNA samples.

In the first component, as many methylation data as possible are collected from public data, such as the Cancer Genome Atlas (TCGA), Gene Expression Omnibus (GEO) repository, Roadmap epigenomics, and other articles in the scientific literature. Cancer-specific or normal tissue-specific methylation signatures are established based on the existing methylation data to building a library of methylation signatures where each signature corresponds to a cancer type or tissue type.

In the second component, a patient's plasma cfDNAs is sequenced and his/her "phased" methylation data is obtained, for example, using the Whole Genome Bisulfite Sequencing (WGBS) method from Illumina or the Reduced Representation Bisulfite Sequencing (RRBS) method. Then, a "phased" methylation based probabilistic method is applied to infer the plasma cfDNA compositions with regard to two classes.

Using sequencing data of cancer patients, cancer-specific methylation signatures can be established. The cancer-specific methylation signatures can be used to detect the presence of a specific cancer type as well as determine the relative composition of normal plasma and a specific cancer type within a particular cfDNA sample.

Using sequencing data of normal or non-cancer patients, tissue specific methylation signatures can established. The tissue-specific methylation signatures can be used to detect the presence of a specific tissue type as well as determine the relative composition of different tissue types within a particular cfDNA sample.

In the third component, different plasma cfDNA compositions inferred in the previous step are integrate to answer two questions: (i) is this patient healthy or cancerous? (ii) if he/she gets cancer, where is the tumor?

Additional description and exemplary embodiments of each component are included in the following and the examples.

Methylation Signatures

The massive amount of publicly available methylation data, including WGBS, RRBS and array-based data, can be utilized to establish the cancer-specific and tissue-specific methylation signatures. A methylation signature includes at least two types of information: it denotes a genomic region and it represents the methylation status of the genomic region. In some embodiments, the methylation signatures also describe the inter-individual variance of methylation levels in a population of a tissue (FIG. 2) or tumor type (FIG. 1B).

For examples, a two-step procedure is adopted to establish methylation signatures:

Step 1: Genomic regions that can differentiate cancer types (or normal tissue types), so called "cancer-specific" methylation regions (or "tissue-specific" methylation regions) will be identified. In some embodiments, genomic regions can be represented as a segment on a particular chromosome; for example, chromosome 11, nt 2,000 to nt 3,000. We can either use existing "differential methylation region" (DMR) detection methods, or design a simple scoring function, that describes the differential power of each region, such as in the work by Sun et al. (2015).

Step 2: In each region identified in Step 1, methylation signature is characterized at different genomic resolutions (CpG sites or genomic bins), for each class (i.e., a cancer type, or a tissue type, or normal plasma) using a population of samples of this class. Choosing a genomic resolution for methylation signature depends on the information public methylation data can provide.

Figure 4:
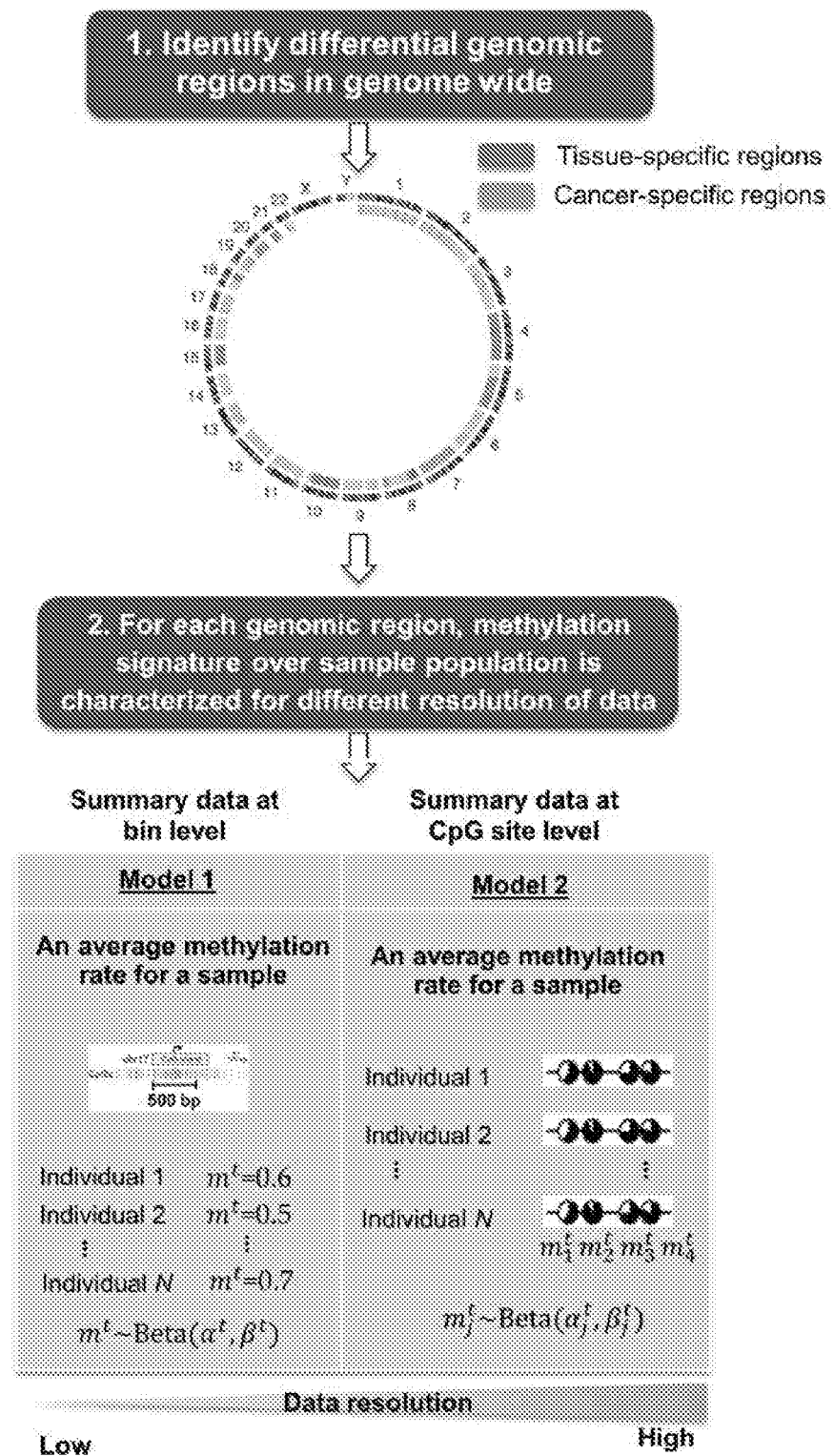
FIG. 4 depicts an exemplary embodiment, illustrating how methylation signatures can be established based on averaged value across a population of tissue samples. Two models are used for characterizing methylation signature at different resolutions: bins (model 1) and CpG sites (model 2).

As noted above, methylation signatures comprise at least two types of information: genomic regions or locations and methylation status within the genomic regions or locations. Methylation signatures can be represented in multiple ways. Methylation signatures can be established at both population and individual levels. For example, at the population level, the Beta distribution modeling methylation rates of a set of individuals for a particular genomic region can be determined either at the bin level (model 1) or at individual CpG site level (model 2); see, FIG. 4. At the individual level, methylation rate can be determined from raw bisulfite sequencing data (model 1), at individual site level (model 2) and at bin level (model 3); see, FIG. 11.

It would be understood that a particular disease can correspond to multiple methylation signatures. In some embodiments, a disease corresponds to two methylation signatures; five or fewer methylation signatures; 10 or fewer methylation signatures; 15 or fewer methylation signatures; 20 or fewer methylation signatures; 50 or fewer methylation signatures; 100 or fewer methylation signatures; 150 or fewer methylation signatures; 200 or fewer methylation signatures; 250 or fewer methylation signatures; 500 or fewer methylation signatures; 750 or fewer methylation signatures; 1,000 or fewer methylation signatures; 1,500 or fewer methylation signatures; 2,000 or fewer methylation signatures; 3,000 or fewer methylation signatures; 4,000 or fewer methylation signatures; 5,000 or fewer methylation signatures; 7,500 or fewer methylation signatures; 10,000 or fewer methylation signatures; 15,000 or fewer methylation signatures; or 20,000 or fewer methylation signatures. In some embodiments, a disease corresponds to 20,000 or more methylation signatures.

In some embodiments, the methylation signatures are disease specific. In some embodiments, the methylation signatures are not disease specific. However, the methylation signatures vary significant between diseases such that the variance can be used to detect the presence of a particular disease type.

In some embodiments, methylation data can be established at the bin level. See, for example, FIG. 11 model 3. The size of a bin is a pre-determined length of nucleic acid sequence. For example, a bin can include 10,000 nt or fewer; 5,000 nt or fewer; 2,500 nt or fewer; 1,500 nt or fewer; 1,000 nt or fewer; 800 nt or fewer; 600 nt or fewer; 500 nt or fewer; 400 nt or fewer; 300 nt or fewer; 200 nt or fewer; 100 nt or fewer; 50 nt or fewer; 40 nt or fewer; 20 nt or fewer; or 10 nt or fewer. In some embodiments, a bin can include 10,000 nt or more;

For example, for a class t of samples, each sample has a methylation rate $m^t$ in the range [0,1] in the same bin. It is usually modeled by Beta distribution $m^t \sim Beta(\alpha^t, \beta^t)$.

In some embodiments, methylation data can be established at individual CpG site level. See, for example, FIG. 11 model 2. For CpG site j of the class t, each sample has a methylation rate $m_j^t$, which is usually modeled by Beta distribution $m_j^t \sim Beta(\alpha_j^t, \beta_j^t)$. In these embodiments, methylation status is provided for each CpG site for a given segment of nucleic sequence.

As disclosed herein, the symbol $\Omega t$ is used to denote all methylation signatures for class t. Here, each class can be a disease type, a cancer type, a tissue type and etc.

Alternatively, DNA methylation pattern can be defined based on raw bisulfite sequencing data and frequency histogram. See, for example, FIG. 11 model 1.

Similar methods and systems can be used to calculate methylation patterns of sample whose tissue type and disease type are unknown. For example, blood sample can be taken from a patient and sequencing data can be obtained for cfDNA samples derived from the blood sample. Here, a methylation pattern obtained from an unknown sample also comprises two types of information: nucleic acid sequence and methylation status associated therewith.

However, as disclosed herein, sequencing data comprise sequencing reads. Sequencing reads are raw sequences derived from consecutive segments of nucleic acids. As such, methylation status of any sequencing read is "phased;" i.e., it represents the methylation status of only one of the alleles from the diploid chromosomal DNA. When methylation status is averaged over multiple reads, it becomes allele non-specific and can also be called "unphased."

As disclosed herein, a sequencing read may include 1,000 nt or fewer; 800 nt or fewer; 600 nt or fewer; 500 nt or fewer; 400 nt or fewer; 300 nt or fewer; 200 nt or fewer; 100 nt or fewer; 50 nt or fewer; 40 nt or fewer; 20 nt or fewer; or 10 nt or fewer. In some embodiments, a sequencing read may include 1,000 nt or more (or any range derivable therein).

Analytical Framework

As described hereinabove, methylation signatures are established based on existing sequencing data from specific tissue type or disease type (e.g., cancer type), forming libraries of methylation signatures. Each library is associated with a particular tissue type or disease type (e.g., a particular cancer type). These libraries can be used as standards for subsequent analysis.

For example, methylation patterns of a sequencing read can be compared with methylation signatures in one or more established libraries. Methylation patterns similar to established methylation signatures suggest that the cfDNA sample includes nucleic acid fragments from the particular tissue type, thus determining composition of plasma cfDNA. Additionally, methylation patterns similar to established methylation signatures can also suggest the cfDNA sample includes nucleic acid fragments relating to a particular disease such as liver cancer or lung cancer.

In some embodiments, multiple blood samples can be taken from the same patient over a period of time. Methylation patterns derived from these blood samples can be used to monitor disease onset for high risk population. Alternatively, methylation patterns derived from these blood samples can be used to monitor disease progression; e.g., cancer prognosis.

In some embodiments, a probabilistic framework can be used to determine the relation between methylation patterns of unknown samples and established methylation signatures. Within the framework, either an exhaustive search of all possible solutions (called grid search algorithm) or an expectation-maximization (EM) algorithm applied. The EM algorithm is an iterative method for finding maximum likelihood or maximum a posteriori (MAP) estimates of parameters in statistical models, where the model depends on unobserved latent variables.

Exemplary embodiments of a probabilistic analysis are presented in Example 2. This probabilistic framework and EM algorithm is flexible, because we can (i) either add or remove the new unknown tissue type from them; and (ii) consider different models of tissue-specific methylation signature that depend on what resolution methylation data we can collect from public database.

In some embodiments, personalized deconvolution of plasma cfDNAs can be achieved using the buffy coat sample of the same patient. We assume a patient's white blood cells of buffy coat sample releases their DNAs into the plasma. Therefore, in the normal tissue composition inference step, we can use methylation signatures of white blood cells of the patient himself, instead of using methylation signatures of other people's white blood cells. It is expect that this may remove some inter-individual variances or germline variances.

In some embodiments, methods disclosed herein can be applied to analyze the composition and tissue origin of cfDNA. In some embodiments, changes in such compositions can be used to monitor the health of an individual. For example, detecting of cancerous nucleic acid material is an obvious warning sign, which warrants further tests and examinations. For example, the liver DNA component in the cfDNA of a healthy individual may be within a certain range. A sudden rise of liver DNA component in cfDNA samples may indicate altered health conditions. Similarly, the sudden decrease of a particular DNA component in the cfDNA sample of an individual may also suggest altered health conditions.

In some embodiments, methods disclosed herein can be applied to analyze the composition of blood cells such as white blood cells. Recent studies reported that the abnormal composition of different white blood cell types in buffy coat sample of a patient is also a disease indicator. Particularly, the peripheral blood immune cell methylation profiles are reported to be associated with non-hematopoietic cancers. Therefore, we can apply our method to this problem and integrate it as the third dimension for cancer diagnosis.

cfDNA Composition and Disease Diagnosis and Prognosis

After the composition and tissue origin of cfDNA are determined, the information can be integrated for disease diagnosis and prognosis. For example, plasma cfDNA cancer compositions and tissue composition can be integrated for cancer diagnosis. These two kinds of compositions can be used as two features of any patient. Ideally, supposing we have plasma cfDNA samples collected from a large amount of healthy people and the patients with T cancer types, then the naïve Bayes classifier can be used and trained by these 2-feature data for diagnosing whether or not a new coming patient gets cancer and which cancer type he/she gets.

Figure 7:
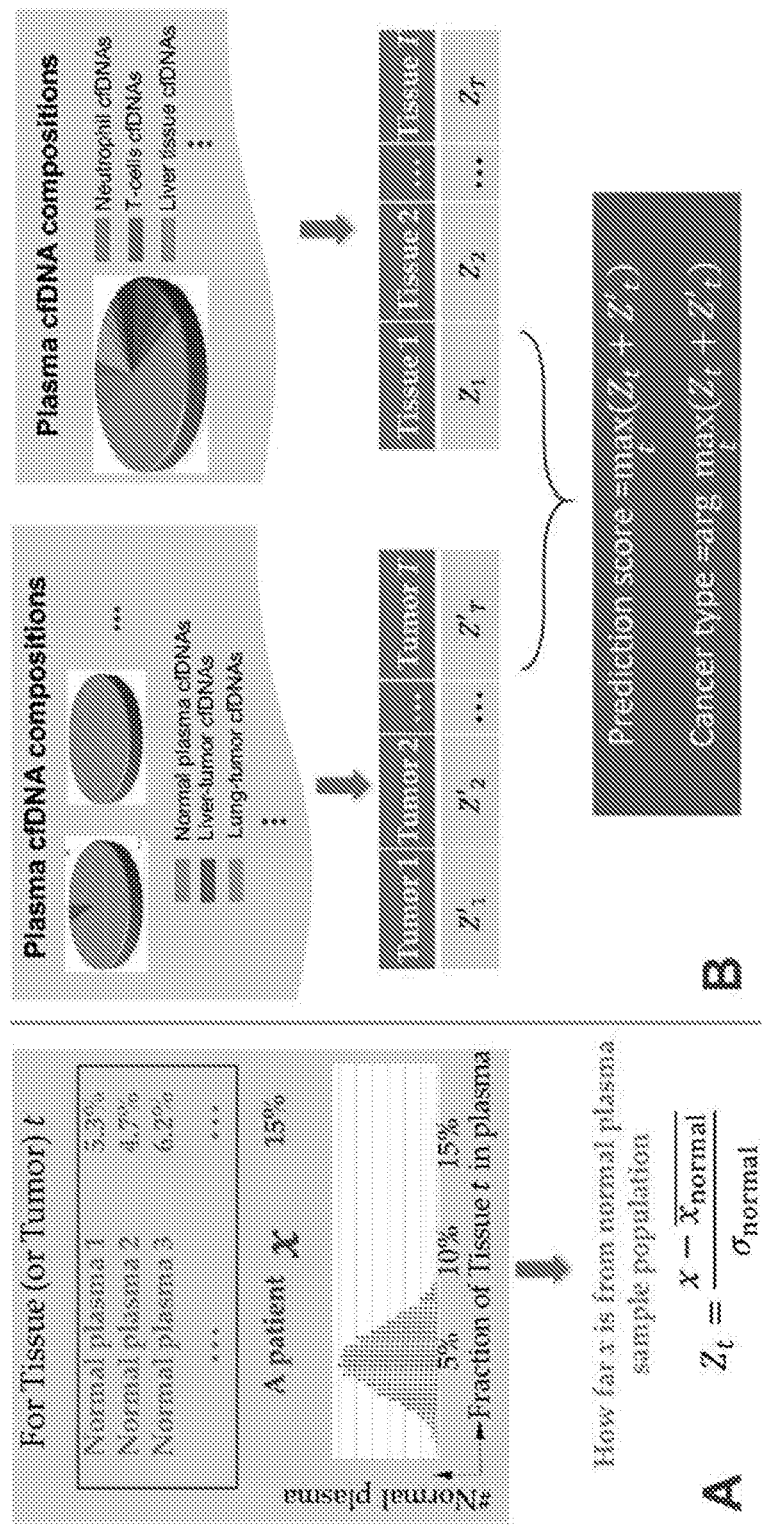
FIG. 7 depicts an exemplary embodiment, illustrating how plasma cfDNA cancer and tissue compositions of a patient are used for cancer diagnosis. (A) Compute Z-score to evaluate how far the fraction of a class t is from normal plasma samples; (B) Integrate Z-score of each class's faction into a prediction score.

However, due to the limited number of plasma samples, it is impossible to train Naïve Bayes method for prediction in real data. Therefore, we designed a simple diagnosis method based on Z-scores for small sample size. The intuition is that The more elevated the fraction of class t of the new patient is from those of normal people, the more likely this patient gets cancer and the cancer type is the class t with the most elevated fraction. As shown in FIG. 7, we assume that we have obtained the empirical distribution of how each tissue's (or tumor's) fraction in a population of normal plasma samples. Therefore, for a new patient, we can first perform Step 2 to obtain his/her fraction (denoted as x) of tissue (or tumor) t, then calculate Z-score $Z_t$ (or $Z_t'$) to evaluate how far x is from normal plasma population:

$$Z_t = \frac{x - \overline{x_{normal}}}{\sigma_{normal}}$$

where $\overline{x_{normal}}$ ($\sigma_{normal}$) is the average (standard deviation) fraction of tissue (or tumor) t in the normal plasma population. Then the prediction score is the maximum of $Z_t+Z_t'$ over all tissues t=1, ..., T. This score is intuitive, because the patient whose two fractions of tissue and tumor t in his/her plasma cfDNAs are farmost from normal people population, is most likely to get cancer type t. If $\max_t(Z_t+Z_t')$ falls into the normal range, then this patient is likely to be heathy.

Computer System and Program Product

The method disclosed herein can be implemented as a computer system and/or a computer program product that comprises a computer program mechanism embedded in a computer readable storage medium. Further, any of the methods of the present invention can be implemented in one or more computers or computer systems. Further still, any of the methods of the present invention can be implemented in one or more computer program products. Some embodiments of the present invention provide a computer system or a computer program product that encodes or has instructions for performing any or all of the methods disclosed herein. Such methods/instructions can be stored on a CD-ROM, DVD, magnetic disk storage product, or any other computer readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise, by transmission of a computer data signal (in which the software modules are embedded) either digitally or on a carrier wave.

Some embodiments of the present invention provide a computer system or a computer program product that contains any or all of the program modules as disclosed herein. These program modules can be stored on a CD-ROM, DVD, magnetic disk storage product, or any other computer readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

In some embodiments, the method disclosed herein can be implemented in a networked device selected from the group consisting of a desktop computer, a laptop computer, a cellular phone, a personal digital assistant (PDA), an iPod, a tablet, a mobile device equipped with a network device, a smart phone, a pager, a television, a media player, a digital video recorder (DVR), and any other networked devices.

Further Embodiments Related to CancerLocator

Cancer cells can often display aberrant DNA methylation patterns, such as hypermethylation of the promoter regions of tumor suppressor genes and pervasive hypomethylation of intergenic regions. Therefore, DNA methylation can be a target for cancer diagnosis in clinical practice. Hyper/hypomethylated tumor DNA fragments can be released into the bloodstream via cell apoptosis or necrosis, where they become part of the circulating cell-free DNA (cfDNA) in plasma. The non-invasive nature of cfDNA methylation profiling may be an effective strategy for general cancer screening.

Some embodiments may include plasma methylation biomarkers for various specific cancers. The differentially methylated marker genes can be identified by comparing methylation profile data from patients with a certain cancer type to healthy controls. With a variety of methylation profiles specific to different cancers being identified, the embodiments disclosed herein can detect many types of cancers and provide tumor location information for further specific clinical investigation based on a simple non-invasive liquid biopsy.

FIG. 12 is a flow chart of a method 100 for screening cancer and identifying tissue-of-origin of a tumor, according to one embodiment.

As shown in FIG. 12, the method 100 learns the informative features of different cancer types from the vast amount of the cancer genome (TCGA) DNA methylation data 110. The method then models the plasma cfDNAs 125 in cancer patients as a mixture of normal cfDNAs 130 and ctDNAs 120. Finally, given the genome-wide methylation profile derived from the cfDNA sample 130 of an unknown patient, the embodiments disclosed herein uses the informative features 115 to estimate the fraction of ctDNA in the plasma 125, and the likelihood that the detected ctDNAs comes from each tumor type 135. Based on those likelihoods embodiments disclosed herein make the final decision 135 on whether the patient has tumors, and if yes, the locations of the primary tumor.

The first step of the method 100 is to identify the informative features of normal plasma 105 and multiple tumor types from the massive TCGA database 110. The method 100 focuses on seven cancer types from the five organs, e.g., breast, colon, kidney, liver, and lung, that are generally regarded as having a high level of blood circulation. The second step, given the plasma cfDNA methylation profile of a patient, the method 100 uses those informative features to simultaneously detect cancer and locate its tissue of origin.

In the first step, the method selects CpG clusters as features if their methylation range (MR) is sufficiently large 115. The "CpG" sites are regions of DNA where a cytosine nucleotide is followed by a guanine nucleotide in the linear sequence of bases along its 5'→3' direction. CpG sites are grouped into CpG clusters. MR is defined as the range of average methylation levels observed in healthy plasma and different solid tumor tissues.

The embodiments disclosed herein group the individual CpG sites into CpG clusters in order to use more mappable reads. For a CpG site covered by a probe in the sequencing process, the embodiment may define the region 100 bp (base pair) upsteam and downstream as its flanking region, and assume that all CpG sites located within this region have the same average methylation level as the CpG sites covered by probes. Two adjacent CpG sites are grouped into one CpG cluster if their flanking regions overlap. Finally, only those CpG clusters containing at least 3 CpG sites covered by microarray probes are used in the embodiments.

In other cases, embodiments disclosed herein generally choose the size of the flanking region and the number of CpGs in a cluster according to three criteria: (i) at least three CpG sites (in the microarray data) are included to obtain a robust measurement of methylation values in the solid tumor samples; (ii) the cluster is reasonably sized, so that there are sufficient CpG sites to calculate the methylation values, even when low coverage sequencing data is used; (iii) keep as many clusters that span within a type of genomic regions (either CpG islands or shores) as possible.

In some embodiments, this procedure yields 42,374 CpG clusters, which together include about one half of all the CpG sites on the Infinium HumanMethylation450 microarray data. For most of those clusters, each cluster is associated with only one gene. These CpG clusters are used for subsequent feature selection. In other embodiments, the procedure may yield from at or around 40,000 to at or around 50,000 CpG clusters. In other embodiments, the procedure may yield from at or around 30,000 to at or around 60,000 CpG clusters. In other embodiments, the procedure may yield from at or around 20,000 to at or around 70,000 CpG clusters. In other embodiments, the procedure may yield from at or around 10,000 to at or around 90,000 CpG clusters. In other embodiments, the procedure may yield from at or around 5,000 to at or around 100,000 CpG clusters.

The method 100 selected a total number of K=14429 CpG clusters (features) on average, whose MR are no less than the threshold of 0.25.

In other embodiments, featured CpG clusters has a total number of K from 14000 to 15000. In other embodiments, featured CpG clusters has a total number of K from 13000 to 16000. In other embodiments, featured CpG clusters has a total number of K from 12000 to 17000. In other embodiments, featured CpG clusters has a total number of K from 10000 to 18000. In other embodiments, featured CpG clusters has a total number of K from 8000 to 20000. In other embodiments, featured CpG clusters has a total number of K from 6000 to 22000. In other embodiments, featured CpG clusters has a total number of K from 5000 to 30000.

In other embodiments, the MR threshold can be equal or around 0.2 to equal or around 0.3. In other embodiments, the MR threshold can be equal or around 0.1 to equal or around 0.5. In other embodiments, the MR threshold can be equal or around 0.05 to equal or around 0.7. In other embodiments, the MR threshold can be equal or around 0.01 to equal or around 0.9. In further embodiments, the MR threshold is, is at least, or is at most 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 300, 400, 500, 600, 700, 800, 900, 1000 or any range derivable therein.

For each CpG cluster, the method takes into account its variation across individuals by modeling the distribution of methylation levels for the same tumor type (or normal plasma) as a beta distribution Beta($\alpha t$, $\beta t$), as shown in 120. The index t=0 represents normal plasma, while t=1, ..., T represents a tumor type.

In the second step, the method 100 uses the selected features (the selected CpG clusters) and their beta distributions to deconvolute a patient's plasma cfDNA methylation profile 130 into the normal plasma cfDNA distribution and, if applicable, a solid tumor DNA distribution at 135. The method 100 may include a probabilistic method that can simultaneously infer the burden and the tissue of origin of the ctDNA. At 135, if the likelihood of presence for any tumor type is not substantially higher than the likelihood that the observed distribution in a normal background, the patient is predicted to be noncancerous. Otherwise, if the likelihood of presence for any tumor type is substantially higher than a normal background, the patient is predicted to have the tumor type that is associated with the highest likelihood.

In one embodiment, the issue of determining the ctDNA burden $\theta$ and tumor type t given a patient's cfDNA methylation profile X can be formulated as a maximum-likelihood estimation function $L(\theta,t|X)$, wherein the likelihood function is expressed as the product of the likelihoods of each selected CpG cluster, assuming that all of the K selected CpG clusters are independent from each other. This is expressed as $L(\theta,t|X)=\Pi_{k=1}^{K} L(\theta,t|x_k)$, where $x_k$ denotes the methylation level of selected CpG cluster k in a cancer patient's cfDNA methylation profile X. In principle, $x_k$ can be a linear combination of the DNA methylation level of a normal plasma and a DNA methylation level of a solid tumor type t with fraction $\theta$. The normal and tumor components of the methylation are denoted by $v_k$ and $u_k$, as shown in FIG. 13. That is, $x=(1-\theta)v+\theta u$ (for simplicity, the subscript k of these notations are skipped). As mentioned earlier, since v and u follow the Beta distributions Beta($\alpha_0,\beta_0$) and Beta($\alpha_t,\beta_t$), respectively, wherein t denotes tumor types and t=0 denotes cancer free profile. Therefore, x follows the distribution $\psi(\theta,t)$, which is calculated as the convolution of two Beta distributions Beta($\alpha_0,\beta_0$) and Beta($\alpha_t,\beta_t$).

In some embodiments, because a patient's plasma may provide low number of cfDNA, the methylation profile of the patient's plasma is usually measured by sequencing-based methods. Therefore, the methylation level $x_k$ of CpG cluster k can be derived from two numbers, $n_k$ and $m_k$, where $n_k$ denotes the total number of cytosines available in the CpG cluster k and $m_k$ denotes the number of methylated cytosines in the CpG cluster k. The embodiments can model $m_k$ and $n_k$ together as a binomial distribution $m_k \sim \text{Binomial}(n_k, x_k)$, and the likelihood function can be rewritten as $L(\theta,t|M,N)=\Pi_{k=1}^{K} L(\theta,t|m_k,n_k)$. The detailed description of this method is expanded in the following items.

In some embodiments, a mixture model of methylation levels of plasma cfDNAs can be used. For example, the cfDNAs in the plasma of cancer patients can be regarded as a mixture of normal background DNAs and tumor-released DNAs. Formally, for each CpG cluster k∈{1, 2, ..., K}, the methylation level $x_k$ of the plasma cfDNA from a given patient can be approximated as a mixture of $v_k$ and $u_k$, where $v_k$ denotes the methylation levels of the normal plasma sample and $u_k$ denotes the methylation levels of the solid tumor tissue. Let $\theta \in (0,1)$, wherein $\theta$ denotes the proportion of tumor-derived DNAs in plasma cfDNA. Then $x_k$ can be expressed as the weighted sum of $v_k$ and $u_k$, i.e. $x_k=(1-\theta)v_k+\theta u_k$.

The embodiments may assume that an individual carries at most one type of tumor among the T possible tumor types. Let t∈{0, 1, 2, ..., T} be the variable representing either normal plasma (t=0) or a tumor type (1≤t≤T). For each CpG cluster k, the embodiments may model its methylation level in a sample of type t as a Beta distribution: $v_k \sim \text{Beta}(\alpha_{k0},\beta_{k0})$ for normal plasma samples (t=0) and $u_k \sim \text{Beta}(\alpha_{kt},\beta_{kt})$ for solid tumor samples of type t∈{1, ..., T}, where $\alpha_{k0}$ and $\beta_{k0}$ (or $\alpha_{kt}$ and $\beta_{kt}$) are the parameters of the beta model of methylation levels of CpG cluster k in normal plasma (solid tumor) samples. As illustrated in Step 1 of FIG. 12, the parameters of these Beta distributions are estimated by the method of moments, using the large amount of public tumor data and normal plasma data.

In some embodiments, by integrating the two Beta distributions ($v_k$ and $u_k$), as shown in FIG. 13, $x_k$ can be modeled by a derived distribution with the given ctDNA burden $\theta$ and source tumor type t. This model is denoted as the probability density function $\psi(x_k|\theta,t)$, which is calculated by the convolution of Beta($\alpha_{k0},\beta_{k0}$) and Beta($\alpha_{kt},\beta_{kt}$). It is formally expressed below:

$$\psi(x_k | \theta, t) = \int_0^1 f_{Beta}\left(\frac{x_k - \theta u_k}{1-\theta} \bigg| \alpha_{k0}, \beta_{k0}\right) f_{Beta}(u_k | \alpha_{kt}, \beta_{kt}) du_k \qquad \text{Eq. (1)}$$

where $f_{Beta}$ is the probability mass function of the Beta distribution.

Some embodiments model the methylated cytosine count of plasma cfDNA sequencing data. In these embodiments, due to its low abundance in plasma, the methylation profile of cfDNA is usually measured by sequencing-based methods, and the methylation levels ($x_k$) of a CpG cluster k can be characterized by the numbers of methylated and unmethylated cytosines on the reads. Let $M=(m_1, m_2, ..., m_K)$ be the number of methylated cytosines and $N=(n_1, n_2, ..., n_K)$ be the total number of cytosines mapped to all CpG sites, where the index runs over all K CpG clusters. For each CpG cluster k, $m_k$ can be modeled by a binomial distribution: $m_k \sim \text{Binomial}(n_k, x_k)$. By integrating the mixture model of $x_k$ in Eq. (1), the embodiments have the likelihood function for each CpG cluster k which has the inputs from the model parameters ($\theta, t, \alpha_{k0}$ and $\beta_{k0}, \alpha_{kt}$ and $\beta_{kt}$) and the sequence measurements of plasma samples ($m_k, n_k$):

$$f(m_k|\theta,t,n_k) = \int_0^1 f_{Binomial}(m_k|n_k,x_k)\psi(x_k|\theta,t)dx_k \qquad \text{Eq. (2)}$$

where $f_{Binomial}$ is the probability density function of the binomial distribution.

Some embodiments utilize maximum likelihood L to estimate blood tumor burden and type, e.g., steps 135 and 140 as shown in FIG. 12. In these embodiments, given the methylation sequencing profile of a patient's plasma cfDNA sample, which can be derived the vectors M and N as previously disclosed, the embodiments aim to find the maximum likelihood estimate of two model parameters: (1) this specific sample's cfDNA tumor burden $\theta$ and (2) its source tumor type t. For integrating the mixture models of multiple markers into the formulation, the embodiments adopted an assumption: all features or markers are independent from each other. This assumption has been widely used in a number of cell-type deconvolution studies. Under this assumption, the log-likelihood can be written as:

$$\log L(\theta,t|M,N) = \Sigma_{k=1}^{K} \log f(m|\theta,t,n_k) \qquad \text{Eq. (3)}$$

Since the integrals in Eqs. (1)-(2) cannot be easily solved analytically, the embodiments use Simpson's rule to calculate the log-likelihood log $L(\theta, t|M, N)$. That is, a set of J predefined $\theta$ values, $$\Theta = \left\{0, \frac{1}{J}, \frac{2}{J}, \ldots, \frac{J-1}{J}\right\},$$

is used to conduct a grid search for the best estimation (i.e., a global optimization solution). The higher the resolution (J), the more precise the estimation. After obtaining the solution (i.e., optimized $\hat{\theta}$ and optimized $\hat{t}$) that maximizes Eq. (3), the embodiments disclosed herein use the estimated parameters to calculate a simple yet effective prediction score that answers two questions "Does the patient have cancer?", and "If the patient has cancer, which tumor type is it?" This prediction score is defined below:

$$\lambda = \frac{1}{K}\left[\log L(\hat{\theta}, \hat{t}|M, N) - L(\theta = 0|M, N)\right] \quad \text{Eq. (4)}$$

where the denominator K is used to normalize the log-likelihood, so that $\lambda$ is comparable when using a different number of features. The variable t is not included in $L(\theta=0|M,N)$ because $\theta=0$ indicates a normal plasma sample. The larger the prediction score $\lambda$, the higher the chance that the patient has a cancer tumor of type $\hat{t}$. Specifically, if $\lambda > a$ threshold, the patient is predicted as getting cancer with the ctDNA burden $\hat{\theta}$ and the tumor type $\hat{t}$; otherwise, he/she is classified as noncancerous.

In some embodiments, in establishing the prediction model, the methylation data of a simulated plasma cfDNA sample is generated by computationally mixing the entire methylation profiles of a normal plasma cfDNA sample and a solid tumor sample (e.g., breast, colon, kidney, liver, or lung tumors), at a variety of ctDNA burdens ($\theta$ values). This strategy can make the simulated methylation data reflecting the potential correlations of methylation values between CpG clusters in real data. In some embodiments, when establishing the prediction model, tumor copy number aberration (CNA) events are added at pre-defined probabilities (10%, 30% and 50% across all CpG clusters).

In some embodiments, the prediction model is evaluated on simulation data with known ctDNA fractions. The results show that prediction model can achieve a Pearson's correlation coefficient (PCC) of 0.975 between the predicted and true proportions of ctDNA, and an error rate of 0.074 for the classification of non-cancer and tumor types. Moreover, the prediction model well performed when the proportion of tumor-derived DNAs in the case that cfDNAs is lower than 50%, which typically in reality represents low CNA. The embodiments of this disclosure achieved promising prediction results on patient plasma samples, including cancer samples collected from early-stage cancer patients.

As shown in FIG. 14A, the majority (87.9%) of the estimated ctDNA burdens for the normal samples are not more than 0.02, and none of them is greater than 0.05. Please note that, whether a sample is from cancer patient or not is determined by the optimal likelihood calculated in the prediction model, not the predicted ctDNA burden. The prediction results for the simulated cancer-patient plasma samples are shown in FIG. 14B.

As shown in FIGS. 14A and 3B, the results show that the variance of the predicted ctDNA burdens ($\theta$) increases with the true $\theta$, implying that the burden estimation becomes less precise when patients are in mid or late cancer stages. This result could be partially explained by the fact that there may exist higher tumor heterogeneity in tumor samples of late stage which introduces the complexity of ctDNA burden prediction. However, this increased variance does not reduce the performance of the cancer detection, because the predicted $\theta$ is still much higher than the normal background. Indeed, as demonstrated in FIG. 14B, the prediction of cancer tissue-of-origin of ctDNA becomes more distinguishable with high ctDNA burden, despite the increased variance in ctDNA prediction. Note that in FIG. 14B, cyan and red circles represent correct and incorrect predictions.

In FIG. 15, the embodiments of the prediction model are further evaluated. For a systematic comparison, the embodiments divide the simulation data into 10 subsets for different cancer stages, each of which includes 200 normal plasma samples and 200 cancer plasma samples of each tumor type. The different cancer stages (from early, mid to late stages) are represented by a set of ctDNA burden ranges ($\theta, \theta+10\%$] as the x axis, where $\theta=0$, 10%, 20%, 15 30%, 40%, 50%, 60%, 70%, 80%, 90%. For a 6-class (t=0, 2, . . . 5) cancer classification problem (normal, breast, colon, kidney, liver, and lung), the embodiments in FIG. 15 adopt the error rate measure for assessing the classification performance. As shown in FIG. 15, for early-stage cancer patients with ctDNA burdens in the range $\theta \in (0, 10\%]$, the prediction model has an error rate of 0.240. For the second lowest ctDNA burdens $\theta \in (10\%, 20\%]$, the prediction model reaches a very high prediction performance of error rate 0.067. The results are notable, because the embodiments of the prediction model perform well with low number of ctDNA fractions, highlighting the usefulness of the embodiments in screening early stage cancers.

As shown in FIG. 17, the embodiments randomly choose 75% of solid tumor samples 605 and 75% of healthy plasma cfDNA samples 615 into the training set to establish the model parameters. The remaining 25% of the healthy plasma samples 620 and the 25% of the tumor ctDNA samples 610 form the simulation data set. The remaining 25% of the healthy plasma samples 620 and all the tumor ctDNA samples 625 collected from cancer patients form the testing set.

Table 1 shows the model prediction results described in FIG. 17. After performing this procedure (including random data partition and predictions) ten times, the predictions of the embodiments are summarized into a confusion matrix, as shown in Table 1. For a new patient's plasma sample 625, the prediction model assumes no prior information about the cancer type. Therefore, the models consider colon and kidney tumors as possible results, even though our real plasma data in Table 1 does not include colon or kidney tumors. The results in Table 1 show that the model performed well. Specifically, the majority of the breast, liver, and lung cancer samples are accurately predicted by the cancer detection model. The cancer detection model obtains a low error rate of 0.265 for the 6-class prediction problem. The results in Table 1 are consistent with the simulation experiments for ctDNA burdens lower than 50% shown in FIGS. 14A and 14B.

To further explore the relationship between estimated ctDNA burdens and tumor types in real data, the inventors plot their relationships in FIG. 16 by summarizing predictions for each plasma sample in all ten runs: the average predicted ctDNA burden (y-axis value) and the most frequently predicted tumor type among ten runs for each sample. It can be observed that the higher the estimated ctDNA burden, the more accurate the prediction of tumor type. This is highly consistent with the results of simulation data shown in FIGS. 14A and 14B. As shown in FIG. 16, for the breast cancer samples, three out of five samples have ctDNA burdens ≤2.2%, and they are predicted as non-cancer. The predicted ctDNA burden of the two correctly predicted samples are 5.0% and 18.0%, respectively, and the latter one is a metastatic sample. For the liver cancer samples, at least 25 of all samples are from early-stage (Barcelona Clinic Liver Cancer stage A) patients. A majority of them (80%) were correctly classified by the prediction model as liver cancer and all of them were detected as cancer samples. Compared to the breast cancer samples, most of the liver samples, even at early stage, can have moderate to high tumor burden (average predicted tumor burden of 14.9% and the highest reaching 59.0%), given that liver has generally strong blood circulation, but we also correctly classified the one with only 2.0% predicted ctDNA burden as liver cancer. Among the twelve lung cancer samples (two samples do not have cancer stage information), at least five of them are collected from early-stage patients. These early-stage samples have predicted ctDNA burdens ranging from 2.0% to 4.0%. Among these five early-stage lung cancer samples, four have been correctly predicted as lung cancer, whereas the remaining one is predicted as non-cancer.

The model correctly predicted 7 out of 8 chronic hepatitis B virus (HBV) samples to be non-cancer samples. In addition, our method successfully predicted the single one sample with benign lung tumor as non-cancer in all ten runs, with the predicted ctDNA burden being 0.0%. These results demonstrate that the cancer detection model disclosed herein can go beyond distinguishing healthy samples from cancer samples and handle more sophisticated scenarios, such as differentiating hepatitis B virus carriers or benign tumor patient from cancer patients.

In addition to being non-invasive, blood-based cancer diagnosis, unlike traditional diagnosis based on tissue biopsy, has the potential to diagnose tumors from many organs. The prediction models disclosed herein aim to exploit this potential of cfDNA by not only diagnosing the presence of tumors, but also detecting the tissue of origin. The embodiments disclosed herein lay out a systematic prediction method for cfDNA-based cancer type inference, comprehensively evaluate its performance on both simulated data and real data. The embodiments disclosed show accurate and useful predictions especially in early stage cancer when the proportion of tumor-derived DNAs is lower than 50%. In addition, the embodiments show the predictions are robust to CNA events, because the genome-wide features may outweigh the local aberrations.

In some embodiments, DNA methylation microarrays of solid tumor tissues were used to obtain the data to train the model, due to the scarcity of whole-genome bisulfite sequencing data in the public domain. Using DNA methylation microarray data is reasonable because it focuses methylation on promoter regions. Therefore, it is expected that the growing amount of whole-genome bisulfite sequencing data will significantly empower the embodiments disclosed herein because it potentially provides higher resolution data.

In some embodiments, the methylation data are collected and processed in the following manner. The embodiments collect a large set of public methylation data of solid tumors and plasma cfDNA samples taken from both healthy people and cancer patients. The majority of tumor methylation profiles in the TCGA (The Cancer Genome Atlas) were assayed using DNA microarrays, e.g., the Infinium Human Methylation450 microarray. The embodiments collect those data for solid tumors with >100 samples from five different organs: 681 samples of breast (BRCA), 290 samples of colon (COAD), 522 samples of kidney (including 300/156 samples of KIRC/KIRP), 169 samples of liver (LIHC), and 809 samples of lung (including 450/359 samples of LUAD/LUSC). In this paragraph, the abbreviation has the following meanings, BRCA: Breast Invasive Carcinoma; COAD: Colon Adenocarcinoma; KIRC: Kidney Renal Clear Cell Carcinoma; KIRP: Kidney Renal Papillary Cell Carcinoma; LIHC: Liver Hepatocellular Carcinoma; LUAD: Lung Adenocarcinoma; LUSC: Lung Squamous Cell Carcinoma.

In some embodiments, two datasets of whole-genome bisulfite sequencing (WGBS) data of plasma samples are taken from 32 normal people, 8 patients infected with HBV, 29 liver cancer patients, 4 lung cancer patients, 5 breast cancer patients, and a number of patients with tumors in organs without a large blood flow. The embodiments also generated WGBS data of plasma samples collected from 8 cancer patients (5 early-stage lung cancer patients, 1 late-stage lung cancer patient, 2 lung cancer patients with unknown stage information) and 1 patient with benign lung tumor. The embodiments used only the normal, HBV, and breast/liver/lung cancer patients in our study, for the total of 87 plasma samples. Note that these public WGBS data have very low sequencing coverage (~4× on average), while the coverage of our newly generated data of all the 9 samples is around 10×.

In some embodiments, blood samples of human subjects are used. The embodiments include blood samples of eight lung cancer patients and one benign lung tumor patient.

Cell-free DNA (cfDNA) isolation and Whole Genome Bisulfite Sequencing (WGBS) are included in the embodiments disclosed herein. In some embodiments, cfDNA isolation and WGBS are processed in the following manners: blood samples were centrifuged first at 1,600×g for 10 minutes, and then the plasma was transferred into new micro tubes and centrifuged at 16,000×g for another 10 minutes. The plasma was collected and stored at −80° C. CfDNA was extracted from 5 ml plasma using a reagent kit, e.g., the Qiagen QIAamp Circulating Nucleic Acids Kit and quantified by a fluorometer, e.g., Qubit 3.0 Fluorometer (Thermo Fisher Scientific). Bisulfite conversion of cfDNA was performed by using a reagent kit, e.g., EZ-DNA-Methylation-GOLD kit (Zymo Research). After that, another reagent kit, e.g., Accel-NGS Methy-Seq DNA library kit (Swift Bioscience) was used to prepare the sequencing libraries. The DNA libraries were then sequenced with 150 bp paired-end reads.

The embodiments build an recognize selected CpG features, i.e., CpG clusters. In some embodiments, the CpG features are built in the following manners. Appropriate microarray data was collected, e.g., Infinium HumanMethylation450 microarray data from TCGA measuring solid tumor samples for about 450,000 CpGs. Since the testing sample of the embodiments can be WGBS data with very low sequencing coverage, the embodiments group the CpG sites into CpG clusters in order to use more mappable reads. For a CpG site covered by a probe on the microarray, the embodiment may define the region 100 bp (base pair) upsteam and downstream as its flanking region, and assume that all CpG sites located within this region have the same average methylation level as the CpG sites covered by probes. Two adjacent CpG sites are grouped into one CpG cluster if their flanking regions overlap. Finally, only those CpG clusters containing at least 3 CpG sites covered by microarray probes are used in the embodiments. The embodiments choose the size of the flanking region and the number of CpGs in a cluster according to three criteria: (i) at least three CpG sites (in the microarray data) are included to obtain a robust measurement of methylation values in the solid tumor samples; (ii) the cluster is reasonably sized, so that there are sufficient CpG sites to calculate the methylation values, even when low coverage sequencing data is used; (iii) keep as many clusters that span within a type of genomic regions (either CpG islands or shores) as possible. In some embodiments, this procedure yields 42,374 CpG clusters, which together include about one half of all the CpG sites on the Infinium HumanMethylation450 microarray data. For most of those clusters, each is associated with only one gene. These CpG clusters are used for subsequent feature selection.

In some embodiments, methylation microarray data are processed. Methylation microarray data may be processed in the following manner. The microarray data (level 3 in the TCGA database) provide the methylation levels of individual CpG sites. The embodiments define the methylation level of a CpG cluster as the average methylation level of all CpG sites in the cluster. A cluster's methylation level is marked as Not Available (NA) if more than half of its CpG sites do not have methylation measurements.

In some embodiments, WGBS data are processed. WGBS data may be processed in the following manner. A DNA sequence alignment tool, e.g., Bismark, can be employed to align the reads to the reference genome HG19 and call the methylated cytosines. After the removal of PCR duplications, the numbers of methylated and unmethylated cytosines are counted for each CpG site. The methylation level ($x_k$) of a specific CpG cluster (k) is calculated as the ratio between the number of methylated cytosines ($m_k$) and the total number of cytosines ($n_k$) within the cluster. However, if the total number of cytosines ($n_k$) in the reads aligned to the CpG cluster is less than 30, the methylation level of this cluster is treated as "NA".

In some embodiments, the CpG clusters are further filtered. Feature filtering can be done in the following manner. For each CpG cluster, the embodiments may use the methylation range (MR) to indicate a feature's differential power between classes. The embodiments first obtained the average methylation level of all samples from each class (i.e., healthy plasma, or each tumor type), then defined MR as the range of this set of mean values (i.e., the difference between the largest and smallest mean values). The higher MR of a cluster is, the more differential power it has. Finally, those CpG clusters whose MRs are no less than a threshold were selected.

Some embodiments generate simulation data, e.g., the combination of 610 and 620 in shown in FIG. 17. The simulation data are computationally generated from normal plasma and tumor plasma for verifying the accuracy of the prediction model L. The embodiments simulate the methylation sequencing data of a patient's plasma cfDNAs using the previously described probabilistic models: (i) a mixture model that treats the cfDNA as a mixture of normal plasma cfDNA and DNAs released from primary tumor sites and (ii) a binomial model for the methylated cytosine count of plasma cfDNA sequencing data. In addition, to make the simulation data more realistic, the embodiments incorporate copy number aberrations and read depth bias. The procedure for generating simulation plasma cfDNA methylation sequencing data is detailed below.

Generating simulation data may need the following inputs: (i) the genomic regions of all K CpG clusters, (ii) the total number of cytosines (Z) on the sequencing reads that are aligned to any CpG cluster, (iii) the range of $\theta$: ($\theta_L, \theta_U$), (iv) the collections of normal plasma samples (denoted as $POOL_{normal}$) and solid tumor samples (denoted as $POOL_{tumor}$), and (v) $b_k$, the background probability for a CpG dinucleotide to be aligned to CpG cluster k, satisfying $\sum_{k=1}^{K} b_k = 1$. The last input reflects the read depth bias introduced during sequencing process and reads alignment, and the density of CpG sites in the clusters.

A simulated methylation sequencing profile of a plasma sample is generated, represented by the integer vectors $M=(m_1, m_2, \ldots, m_K)$ and $N=(n_1, n_2, \ldots, n_K)$. The elements $m_k$ and $n_k$ are the number of methylated cytosines and the total number of cytosines in the reads mapped to CpG cluster k, respectively.

In one embodiment, the simulated methylation sequencing profile of a plasma sample is generated with the following procedures. The procedure includes six steps. Step 1: Generate a random ctDNA fraction $\theta$ from the distribution $\theta \sim \text{Uniform}(\theta_L, \theta_U)$.

Step 2: Generate a random integer copy number $c_k$, for each CpG cluster k, from the categorical distribution $c_k \sim \text{Cat}(6, p_0, p_1, p_2, p_3, p_4, p_5)$, where Cat refers to a categorical distribution. Here $p_c$ denotes the probability of observing copy number $c \in \{0, 1, 2, 3, 4, 5\}$ in the sequencing data. The probabilities $p_c$ satisfy three criteria: (i) their sum is equal to one, $\sum_{c=0}^{5} p_c = 1$; (ii) the average copy number is equal to two, $\sum_{c=0}^{5} c \cdot p_c = 2$; and (iii) extreme copy number alterations are less likely to occur. In some cases, the embodiments may predefine $p_0 = 0.005$, $p_1 = 0.16$, $p_2 = 0.7$, $p_3 = 0.105$, $p_4 = 0.025$, $p_5 = 0.005$. Note that the sum of all these probabilities except $p_2$ (30% in this case) is the probability of any given CpG cluster having a CNA event. The embodiments may have other probability configurations for the simulation with more (50%) or fewer (10%) CNA events, and obtained similar results. No CNA event is considered (i.e. $c_k$ is fixed to two) when simulating a normal plasma sample.

Step 3: Randomly select a normal plasma sample from $POOL_{normal}$ whose methylation profile is denoted by $(v_1, v_2, \ldots, v_K)$, and randomly select a solid tumor from $POOL_{tumor}$ whose methylation level profile is denoted by $(u_1, u_2, \ldots, U_K)$. Note that some embodiments may also randomly select two normal plasma samples from $POOL_{normal}$, in order to simulate a new normal plasma sample.

Step 4: Calculate the methylation level $x_k$ of plasma cfDNA at CpG cluster k. This is the adjusted linear combination of $v_k$ and $u_k$ after incorporating the copy number $c_k$ generated in Step 2. That is, $x_k = (1-\theta_k')v_k + \theta_k' u_k$, where $\theta_k'$ is the adjusted value of $\theta$ given by $$\theta_k' = \frac{\theta c_k}{\theta c_k + 2(1-\theta)}, \theta_k'$$

describes the actual ctDNA fraction after considering the copy number $c_k$ of the ctDNA.

Step 5: Generate a random number $n_k$, representing the total number of cytosines in CpG cluster k, from the Poisson distribution $n_k \sim \text{Poisson}(ZB_k)$. $B_k$ is the adjusted CpG dinucleotide bias $b_k$, given by $$B_k = \frac{b_k(1 - \theta + \theta c_k/2)}{\sum_{k=1}^{K} b_k(1 - \theta + \theta c_k/2)},$$

after scaling with the copy number $c_k$ generated in Step 2.

Step 6: Generate a random number $m_k$ from the binomial distribution $m_k \sim \text{Binomial}(n_k, x_k)$.

Some embodiments also simulated new normal plasma sample by mixing two normal plasma samples at different mixture ratios. The procedure is the same as above except that Step 2 is ignored by fixing all copy numbers as two, because there are no CNA events in the normal plasma samples.

Some embodiments have the following method for data partitions for learning signature features, simulation and real data experiments. All the TCGA solid tumor tissues and plasma samples are divided into non-overlapping sets for three tasks: (i) learning discriminating features, (ii) simulation experiments, and (iii) testing on the real data. Specifically, as shown in FIG. 17, the embodiments split the TCGA solid tumors of each tissue type into two partitions: 75% 605 for learning signature features, and 25% 610 for generating simulation data. The embodiments also split all normal plasma samples into two partitions: 75% 615 for learning signature features, and 25% 620 for generating simulation data or for real data experiments. All the plasma samples of the cancer patients 625 are used to form the testing set in the real data experiments. Note that not these plasma samples, but only solid tumor samples collected from public methylation databases, and a subset of normal plasma samples that were not used for testing, were used for learning features. All data are randomly partitioned following the above proportions, and applying a method on one such partition is regarded as "one run". For making the robust results, the embodiments repeat the experiments for ten runs, and aggregate all predictions obtained in the ten runs into a single confusion matrix as the final result. Because the embodiments have limited number of real cancer plasma samples (only 5, 12, and 29 cfDNA samples from breast, lung, and liver cancer patients respectively) for testing, it would not allow the typical cross-validation for the method's hyperparameter estimation.

Various methods, steps, calculations of parameters for cancer detections and tissue-of-origin identification disclosed herein can be implemented in a computer system 700 as shown in FIG. 18 and/or the computer system 800 shown in FIG. 19. For example, the flow chart of the method 100 shown in FIG. 12 can be implemented in the computer system 700 and/or the computer system 800. In another example, as shown in FIG. 13, the equation $p(x_k|\theta,t)$ and the parameters involved x, θ, u, v, k, and t can be implemented as computer readable instructions on computer system 700 and/or computer system 800. In another example, the cancer detection results shown in FIGS. 14A-16 can be executed by computer system 700 and/or computer system 800. In yet another example, the data partitions for learning signature features, simulation experiments, and real data experiments can be executed by computer system 700 and/or computer system 800. In yet another example, the confusion matrix shown in Table 1 can be executed by computer system 700 and/or computer system 800.

FIG. 18 illustrates a computer system 700 for obtaining access to database files for detecting cancer and identifying tissue-of-origin according to one embodiment of the disclosure. The computer system 700 may include a server 702, a data storage device 706, a network 708, and a user interface device 710. The server 702 may also be a hypervisor-based system executing one or more guest partitions hosting operating systems with modules having server configuration information. In a further embodiment, the system 700 may include a storage controller 704, or a storage server configured to manage data communications between the data storage device 706 and the server 602 or other components in communication with the network 708. In an alternative embodiment, the storage controller 604 may be coupled to the network 708.

In one embodiment, the user interface device 710 is referred to broadly and is intended to encompass a suitable processor-based device such as a desktop computer, a laptop computer, a personal digital assistant (PDA) or tablet computer, a smartphone or other mobile communication device having access to the network 708. In a further embodiment, the user interface device 710 may access the Internet or other wide area or local area network to access a web application or web service hosted by the server 702 and may provide a user interface for enabling a user to enter or receive information.

The network 708 may facilitate communications of data between the server 702 and the user interface device 710. The network 708 may include any type of communications network including, but not limited to, a direct PC-to-PC connection, a local area network (LAN), a wide area network (WAN), a modem-to-modem connection, the Internet, a combination of the above, or any other communications network now known or later developed within the networking arts which permits two or more computers to communicate.

FIG. 19 illustrates a computer system 800 configured for cancer detection and tissue-of-origin identification according to one embodiment of the disclosure. FIG. 19 also illustrates a computer system 800 adapted according to certain embodiments of the server 702 and/or the user interface device 710. The central processing unit ("CPU") 802 is coupled to the system bus 804. The CPU 802 may be a general purpose CPU or microprocessor, graphics processing unit ("GPU"), and/or microcontroller. The present embodiments are not restricted by the architecture of the CPU 802 so long as the CPU 802, whether directly or indirectly, supports the operations as described herein. The CPU 802 may execute the various logical instructions according to the present embodiments.

The computer system 800 may also include random access memory (RAM) 808, which may be synchronous RAM (SRAM), dynamic RAM (DRAM), synchronous dynamic RAM (SDRAM), or the like. The computer system 800 may utilize RAM 808 to store the various data structures used by a software application. The computer system 800 may also include read only memory (ROM) 806 which may be PROM, EPROM, EEPROM, optical storage, or the like. The ROM may store configuration information for booting the computer system 800. The RAM 808 and the ROM 806 hold user and system data, and both the RAM 808 and the ROM 806 may be randomly accessed.

The computer system 800 may also include an I/O adapter 810, a communications adapter 814, a user interface adapter 816, and a display adapter 822. The I/O adapter 810 and/or the user interface adapter 816 may, in certain embodiments, enable a user to interact with the computer system 800. In a further embodiment, the display adapter 822 may display a graphical user interface (GUI) associated with a software or web-based application on a display device 824, such as a monitor or touch screen.

The I/O adapter 810 may couple one or more storage devices 812, such as one or more of a hard drive, a solid state storage device, a flash drive, a compact disc (CD) drive, a floppy disk drive, and a tape drive, to the computer system 800. According to one embodiment, the data storage 812 may be a separate server coupled to the computer system 800 through a network connection to the I/O adapter 810.

The communications adapter 814 may be adapted to couple the computer system 800 to the network 708, which may be one or more of a LAN, WAN, and/or the Internet. The user interface adapter 816 couples user input devices, such as a keyboard 820, a pointing device 818, and/or a touch screen (not shown) to the computer system 800. The display adapter 822 may be driven by the CPU 802 to control the display on the display device 824. Any of the devices 802-822 may be physical and/or logical.

The cancer detection models of the present disclosure are not limited to the architecture of computer system 800. Rather the computer system 800 is provided as an example of one type of computing device that may be adapted to perform the functions of the server 702 and/or the user interface device 710. For example, any suitable processor-based device may be utilized including, without limitation, personal data assistants (PDAs), tablet computers, smartphones, computer game consoles, and multi-processor servers to implement various embodiments and/or steps the cancer detection models disclosed herein. Moreover, various embodiments of the cancer detection methods of the present disclosure may be implemented on application specific integrated circuits (ASIC), very large scale integrated (VLSI) circuits, or other circuitry. In fact, persons of ordinary skill in the art may utilize any number of suitable structures capable of executing logical operations according to the described embodiments. For example, the computer system 700 and 800 may be virtualized for access by multiple users and/or applications.

Various methods, steps, calculations of parameters disclosed herein if implemented in firmware and/or software, the various functions described above may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc includes compact discs (CD), laser discs, optical discs, digital versatile discs (DVD), floppy disks and blu-ray discs. Generally, disks reproduce data magnetically, and discs reproduce data optically. Combinations of the above should also be included within the scope of computer-readable media.

In addition to storage on computer-readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims.

Further Embodiments Related To Cancer Detector

Several reasons motivate methylation-based tumor cfDNA detection: (i) DNA methylation patterns are pervasive, meaning that the same methylation patterns (methylated or unmethylated) tend to spread throughout a genome region. This feature has been employed by one group to evaluate DNA hypomethylation across large genome regions for cancer diagnosis (Chan et al. (2013)). As disclosed herein this feature is used to amplify aberrant cfDNA signals but at the resolution of single sequencing reads, therefore providing an ultra-sensitive detection of a tiny amount of tumor cfDNA even at a low sequencing coverage. (ii) Aberrant DNA methylation patterns occur early in the pathogenesis of cancer (Baylin et al. (2001)), therefore facilitating early cancer detection. In fact, DNA methylation abnormalities are one of the hallmarks of cancer and are associated with all aspects of cancer, from tumor initiation to cancer progression and metastasis (Cheishvili et al. (2015), Roy et al. (2014), Plass et al. (2013)), and have become attractive targets for cancer epigenetic therapy (Smith et al. (2007), Sigalotti et al. (2007)).

A key aspect involves focusing on the joint methylation patterns of multiple adjacent CpG sites on an individual cfDNA sequencing read, in order to exploit the pervasive nature of DNA methylation for signal amplification. Traditional DNA methylation analysis focuses on the methylation rate of an individual CpG site in a cell population. This rate, often called the β-value, is the proportion of cells in which the CpG site is methylated (see an example in FIG. 1). However, such population-average measures are not sensitive enough to capture an abnormal methylation signal affecting only a small proportion of the cfDNAs. FIG. 20 illustrates this point: the average methylation rates of the individual CpG sites are $\beta_{normal}=1$ for normal plasma cfDNAs, and $\beta_{tumor}=0$ for tumor cfDNAs; assuming the presence of 1% tumor cfDNAs, the traditional measure yields $\beta_{mixed}=0.99$, which is hard to differentiate from $\beta_{normal}=1$. However, based on the pervasive nature of DNA methylation, a new way to differentiate disease-specific cfDNA reads from normal cfDNA reads was investigated. When the methylation values of all CpG sites in a given read (denoted α-value) are averaged, there is a striking difference (0 and 1) between the abnormally methylated cfDNAs and the normal cfDNAs ($\alpha_{tumor}=0\%$ and $\alpha_{normal}=100\%$). In other words, given the pervasive nature of DNA methylation, the joint methylation patterns of multiple adjacent CpG sites can easily distinguish cancer-specific cfDNA reads from normal cfDNA reads. Inspired by the α-value, it was realized that the key to exploiting pervasive methylation is to estimate whether the joint probability of all CpG sites in a read follows the DNA methylation signature of a disease. This read-based probabilistic approach, is termed "CancerDetector"; it can sensitively identify a trace amount of tumor cfDNAs out of all cfDNAs in plasma.

Some CancerDetector embodiments were evaluated on simulated plasma samples that subsample and combine sequencing reads of a normal plasma cfDNA sample and a solid tumor sample at known mixing rates (or tumor burdens). The results showed that CancerDetector can achieve a Pearson's correlation coefficient (PCC) of 0.9974 (P-value 9.8E-8) between the predicted and true proportions of tumor cfDNAs at medium sequencing coverage (10×). And the prediction performance increases with the sequencing coverage—the higher the sequencing coverage, the closer the predicted tumor burden is to the true value. Moreover, CancerDetector outperformed our previous method of cfDNA tumor burden prediction, i.e., "CancerLocator" (Kang et al. (2017)), in terms of both prediction performance and robustness. We then tested CancerDetector on real plasma cfDNA samples and demonstrated its high performance across 10 experimental runs, i.e., sensitivity of 94.4%±3.7% (when specificity is 100%) for early-stage cancer patients; while CancerLocator has a sensitivity of 74.4%+10.0% (when specificity is 100%). In addition, the tumor burden predicted by CancerDetector showed great consistency with clinical information, such as tumor size and survival outcome, in longitudinal samples. Note that we achieved these results based on real samples that have low sequencing coverage (1×~3×, averaged across all genome positions).

FIG. 21 is a method 200 for detecting a cancer, according to one embodiment. The method 200 includes a step of identifying DNA methylation markers 110. The method 200 includes a step of sequencing a cfDNA methylation profile of a patient 120. The method includes a step of inferring cfDNA composition using read-based probabilistic model 130.

At the step 110, DNA methylation markers are identified, for example, marker-1 112, marker-2 114, marker-3 116, . . . and marker-K 118. Methylation markers 112, 114, 116, 118 are methylation patterns specific to a certain type a cancer, e.g., liver cancer.

To identify DNA methylation markers, a J number of CpG clusters are identified in a cfDNA methylation profile. Using liver cancer as an example, among all J CpG clusters, a set of CpG clusters are chosen to be markers, whose methylation levels can differentiate most liver tumor from both normal liver cell and normal plasma. This task may further include two steps: (1) selecting those "frequently differential methylation regions (FDMR)," in which the methylations are differential (greater than a cutoff) between matched liver tumor and normal liver tissue in more than half of the matched paired. This step can remove markers specific to healthy liver tissues and retain markers specific to liver cancer. (2) Selecting those FDMRs that can distinguish tumor samples from normal plasma samples. This can be done by selecting the FDMRs whose difference between the medians of its methylation pattern in the normal class (N-class) and the tumor class (T-class) is greater than a predetermined threshold. This step ensures that the tumor mehtylatinsignal can be identified in blood. Given a fixed sequencing coverage of cfDNAs, the more markers are used, the lower quality these markers may have, but the more tumor-derived cfDNA reads may be identified. Therefore, there is a tradeoff between the amrker's quality and the amount of tumor cfDNA signals can be used.

In one embodiment, the above mentioned predetermined thresholds for the two steps mentioned in the previous paragraph can be 0.1 to 0.9, e.g., 0.1, 0.2, 0.3, 0.4, 0.5, 0.6, 0.7, 0.8, and 0.9. In one embodiment, the predetermined threshold can be 0.1 to 0.3. In yet another embodiment, the threshold is 0.2.

Each marker 112, 114, 116, 118 corresponds to a marker region 122, 124, 126, and 128 in the cfDNA methylation profile of the patient. Each marker region 122, 124, 126, and 128 has two methylation patterns: one normal class (N-class) pattern and one tumor class (T-class) pattern. The methylation pattern in any class is modeled as beta function Beta($\eta,\rho$). Specifically, a marker k is associated with two methylation patterns, i.e., Beta($\eta_k^T, \rho_k^T$) for the class T and Beta($\eta_k^N, \rho_k^N$) for the class N. Note that $\eta_k^c$ and $\rho_k^c$ are two shape parameters (usually denoted $\alpha$ and $\beta$) of a Beta distribution, but here we used the symbols $\eta$ and $\rho$ to avoid the confusion with $\alpha$-value and $\beta$-values defined in Introduction section. The parameters of a Beta distribution can be easily learnt from the sample population of a class, using either the method of moments or maximum likelihood. To simplify notation, we denote the methylation pattern of marker k for class T as $m_k^T \equiv \text{Beta}(\eta_k^T, \rho_k^T)$, and for class N as $m_k^N \equiv \text{Beta}(\eta_k^T, \rho_k^T)$.

The method 200 further includes calculating the class-specific likelihood of each cfDNA sequencing read 142. The goal was to classify each cfDNA read as class T or N, based on the joint-methylation-status of multiple CpG sites on the read. The joint-methylation-status 134 in a cfDNA read 132 is denoted as $r=(r_1, r_2, \ldots )$, where the binary value $r_j=1$ or 0 represents methylated or unmethylated status of the CpG site j in read r. This binary vector r was modelled by the Beta-Bernoulli distribution.

As shown in FIG. 22, specifically, given a methylation pattern m $\equiv$ Beta($\eta,\rho$) of the marker where read r falls into, the methylation status $r_j$ of each CpG site j in the read is distributed as $r_j$~Bernoulli(p), where p is the prior of average methylation rate of CpG sites within the marker and follows the Beta prior distribution p~Beta($\eta,\rho$). Using this statistical model, the likelihood of the joint methylation status in read $r=(r_1, r_2, \ldots )$ 330, given the methylation pattern m 310 or 320, can be calculated as below:

$$P(r \mid m) = \prod_j P(r_j \mid \text{Beta}(\eta, \rho))$$

$$= \prod_j \int_0^1 \text{Bounoulli}(r_j \mid p) \text{Beta}(p \mid \eta, \rho) dp$$

$$= \prod_j \int_0^1 p^{r_j}(1-p)^{1-r_j} \frac{p^{\eta-1}(1-p)^{\rho-1}}{B(\eta, \rho)} dp$$

$$= \prod_j \frac{B(r_j + \eta, 1 - r_j + \rho)}{B(\eta, \rho)}$$

where B (x,y) is the beta function. Therefore, for marker k with methylation pattern $m_k^T$ of class T and $m_k^N$ of class N, we can use the above formula to compute the class-specific likelihoods of read r, i.e., $P(r \mid m_k^T)$ 322 and $P(r \mid m_k^N)$ 312. Note that this likelihood calculation implements a probabilistic version of $\alpha$-value for individual reads.

Method 200 includes a step 130 of predicting tumor-derived cfDNA burden. As illustrated in FIG. 20, a probabilistic framework was developed to infer the tumor-derived cfDNA fraction (i.e. tumor burden), denoted as $0 \leq \theta < 1$, by classifying cfDNA reads into two classes (class T for tumor-derived DNAs and class N for normal plasma cfDNAs), based on a set of markers associated with the methylation patterns of two classes. Denoted are the methylation patterns of all K markers as $\mathcal{M}\{(m_1^T, m_1^N), \ldots, (m_k^T, m_k^N), \ldots, (m_K^T, m_K^N)\}$. It is also denoted that the methylation sequencing data of a patient's cfDNAs as a set of N reads $R = \{r^{(1)}, \ldots, r^{(N)}\}$ that in total cover M CpG sites. For a read that is aligned to the region of marker k, we assume that it can come from one of two classes with the class-specific likelihood $P(r \mid m_k^c)$, where $m_k^c$ is the methylation pattern of class c. Let $\theta$ be the tumor-derived cfDNA burden, so the fraction of normal cfDNA is $1-\theta$. It is desirable to estimate $\theta$ by maximizing the log-likelihood log $P(R \mid \theta, \mathcal{M})$. This is a maximum likelihood estimation problem. The independence of each read was assumed, $P(R \mid \theta, \mathcal{M}) = \prod_{i=1}^N P(r^{(i)} \mid \theta, \mathcal{M})$. The likelihood $P(r^{(i)} \mid \theta, \mathcal{M})$ of read $r^{(i)}$ is expanded as follows:

$$P(r^{(i)} \mid \theta, \mathcal{M}) = \theta P(r^{(i)} \mid m_k^T) + (1-\theta) P(r^{(i)} \mid m_k^N)$$

Because $P(R \mid \theta, \mathcal{M})$ has only one parameter $\theta$ to be estimated, a grid search can be applied to exhaustively enumerate all 1000 fraction values which are uniformly distributed between 0% and 100%, i.e., 0%, 0.1%, . . . , 0.99% and 100%. This method can get the global optimization at the precision of 0.1%, which we think is sufficient for capturing the tiny amount of tumor-derived cfDNAs. Because the grid search is computationally fast, the steps to determine θ at higher resolutions can be readily refined.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Methylation Signatures

Since most public methylation data of GEO and TCGA are microarray data, a type of summary data which can be best modeled at bin level. Therefore, in this work, bin-level methylation data are used, i.e., Model 1 of FIG. 4, to characterize the methylation signature of each "cancer-specific" or "tissue-specific" region.

It is noted that the method is flexible to allow two different levels of methylation data to be used in the method.

Example 2

Probabilistic Framework of Inferring Plasma cfDNA Compositions with "Phased" Methylation Data The second step is to infer plasma cfDNA compositions of T≥2 classes. As shown in FIG. 3, for "cancer composition", T=2 classes refer to normal plasma cfDNAs and a specific tumor type; while for "tissue composition", T>2 classes refer to T normal tissue types.

Figure 5:
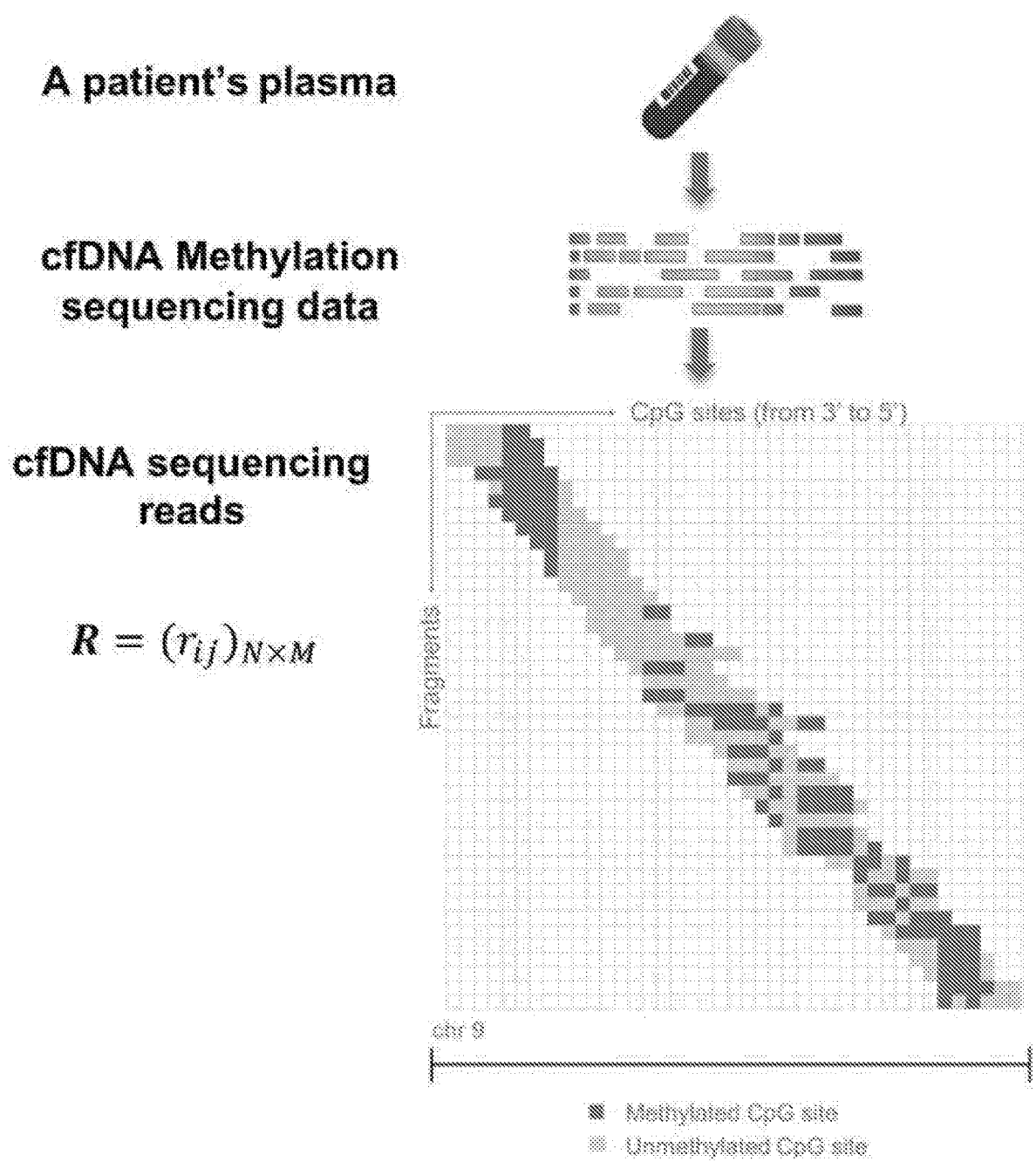
FIG. 5 depicts an exemplary embodiment, illustrating a process for obtaining plasma cfDNA methylation sequencing data.

Due to the small abundance of cfDNA in plasma and utilize the advantages of "phased" data, as shown in FIG. 2, we always perform the methylation sequencing on the patient's plasma cfDNAs. As a result, we have a collection of N cfDNA sequencing reads, covering M CpG sites in all methylation signatures identified in Component 1 of the method. As shown in FIG. 5, these methylation data of fragments can be represented by a ternary matrix $R=(r_{ij})_{N \times M}$, where each row (or column) corresponds to a fragment (or CpG site) and each entry $r_{ij} \in \{0,1,-\}$. $r_{ij}=0$ (or 1) indicates the j-th CpG site is covered by the i-th fragment and is unmethylated (or methylated), while $r_{ij}=-$ indicates site j is not covered by fragment i.

We assume that a patient's plasma cfDNAs is constituted by T known classes with methylation signatures $\Omega^t (1 \leq t \leq T)$ learned in Component 1 of the method and a new unknown tissue type consisting of all cfDNAs that are unlikely to belong to any known classes (for easy understanding, we use "tissues" instead of "classes" in the rest of this section), because it is true in real data that not all cfDNAs are released from T known tissues. So a set of methylation signatures are defined as $\Omega = \{\Omega^1, \Omega^2 \ldots, \Omega^T, \Omega^{T+1}\}$, where $\Omega^t (1 \leq t \leq T)$ is known, $\Omega^{T+1}$ is unknown and will be estimated by our method. Given the input matrix R derived from methylation sequencing data of a patient plasma cfDNA, we have two assumptions:

Assumption 1: each cfDNA fragment is released from a tissue cell subpopulation and the composition of T tissues contributing to the plasma cfDNA is denoted as a composition vector $\Phi = (\theta_1, \theta_2, \ldots, \theta_T, \theta_{T+1})$, where $\theta_t$ ($1 \leq t \leq T+1$) is the cfDNA proportion of tissue t in the plasma cfDNA and $\Sigma_{t=1}^{T+1} \theta_{t=1}$.

Assumption 2: Proportion of cfDNA fragments from a tissue t in the input matrix R can reveal the cfDNA fraction θt of tissue t in the plasma.

Based on these assumptions, the input fragment matrix R and the tissue-specific signatures Ω, we aim to maximize the likelihood (R|Φ,Ω) for estimating the tissue composition θ Φ in plasma cfDNAs. It is formally expressed as below:

$$\max_\Theta \log P(R | \Theta, \Omega) \qquad (1)$$

$$\text{s.t.} \sum_{t=0}^{T+1} \theta_t = 1$$

where Φ and $\Omega^{T+1}$ (in Ω) are parameters to be estimated. This is a typical maximum likelihood estimation (MLE) problem. The log-likelihood can be expanded the summation of the log-likelihood of each cfDNA sequencing read as $$\log P(R | \Theta, \Omega) = \sum_{i=1}^{N} \log P(R_i | \Theta, \Omega) \qquad (2)$$

We optimize Eq. (1) by the Expectation-Maximization (EM) algorithm, and introduce a latent random variable $z_i$ for each cfDNA sequencing read $R_i$ (the i-th row of the matrix R) to indicate which tissue t this read is released from, i.e., $z_i$=t and t=1, 2, . . . , T, T+1. We model $z_i$ to follow the categorical distribution: $z_i \sim Ca(T, \Phi)$, and therefore we have $P(z_i=t|\Phi)=\theta t$. We then rewrite the likelihood of a cfDNA fragment $R_i$ in Eq. (2) as $$P(R_i | \Theta, \Omega) = \sum_{t=1}^{T+1} P(R_i, z_i = t | \Theta, \Omega^t) \qquad (3)$$

$$= \sum_{t=1}^{T+1} P(z_i = t | \Theta) P(R_i | \Omega^t)$$

$$= \sum_{t=1}^{T+1} \theta_t P(R_i | \Omega^t)$$

where $P(R_i|\Omega^t)$ is the tissue-of-origin likelihood of the cfDNA read $R_i$ for tissue t. Let q(t) be the posterior probability of $z_i$=t. Then we have the following Jensen's inequality and the log-likelihood function in Eq. (1) can be lower-bounded by the new function F(q,Φ) defined below.

$$\log P(R \mid \Theta, \Omega) = \sum_{i=1}^{N} \log P(R_i \mid \Theta, \Omega) \quad (4)$$

$$= \sum_{i=1}^{N} \log \sum_{t=1}^{T+1} \theta_t P(R_i \mid \Omega^t)$$

$$= \sum_{i=1}^{N} \log \sum_{t=1}^{T+1} q_i(t) \frac{\theta_t P(R_i \mid \Omega^t)}{q_i(t)} \geq$$

$$\sum_{i=1}^{N} \sum_{t=1}^{T+1} q_i(t) \log \frac{\theta_t P(R_i \mid \Omega^t)}{q_i(t)}$$

$$= F(q, \Theta, \Omega^{new})$$

where we denote $\Omega^{T+1}$ as anew for emphasizing it is a parameter, and q is a set of all $q_i(t)$ over all $i=1, \ldots, N$ and all t over all $t=1, \ldots, T, T+1$. According the EM algorithm, we have the following alternative steps to optimize $(q, \Phi)$ via coordinate ascent.

$$E\text{-Step: } q^{(k+1)} = \underset{q}{\operatorname{argmax}} F(q, \Theta^{(k)}, \Omega^{new(k)}) \quad (5)$$

$$M\text{-step: } \Theta^{(k+1)}, \Omega^{new(k+1)} = \underset{\Theta, \Omega^{new}}{\operatorname{argmax}} F(q^{(k+1)}, \Theta, \Omega^{new}) \quad (6)$$

$\Omega^{new}$ can be the methylation rate at the bin level or CpG site level, denoted as $m_j^{new}$ for bin j (or CpG site j). In the E-step, each $q_i(t)$ of q can be estimated by the posterior probability of $z_i$ given $R_i$, $\Omega^t$ and a predefined parameter setting $\Phi^{(k)}$, that is $$q_i(t) = P(z_i = t \mid \Theta, R_i, \Omega^t) = \frac{\theta_t P(R_i \mid \Omega^t)}{\sum_{t=1}^{T+1} \theta_t P(R_i \mid \Omega^t)} \quad (7)$$

In the M-step, we have $$\theta_t = \frac{\sum_{i=1}^{N} q_i(t)}{\sum_{t=1}^{T+1} \sum_{i=1}^{N} q_i(t)} \quad (8)$$

When methylation signature is modeled by each CpG site j (Model 2):

$$m_j^{new} = \frac{\sum_{\text{read } i \text{ covering CpG site } j} q_i(\text{new}) R_{ij}}{\sum_{\text{read } i \text{ covering CpG site } j} q_i(\text{new})} \quad (9)$$

Figure 6:
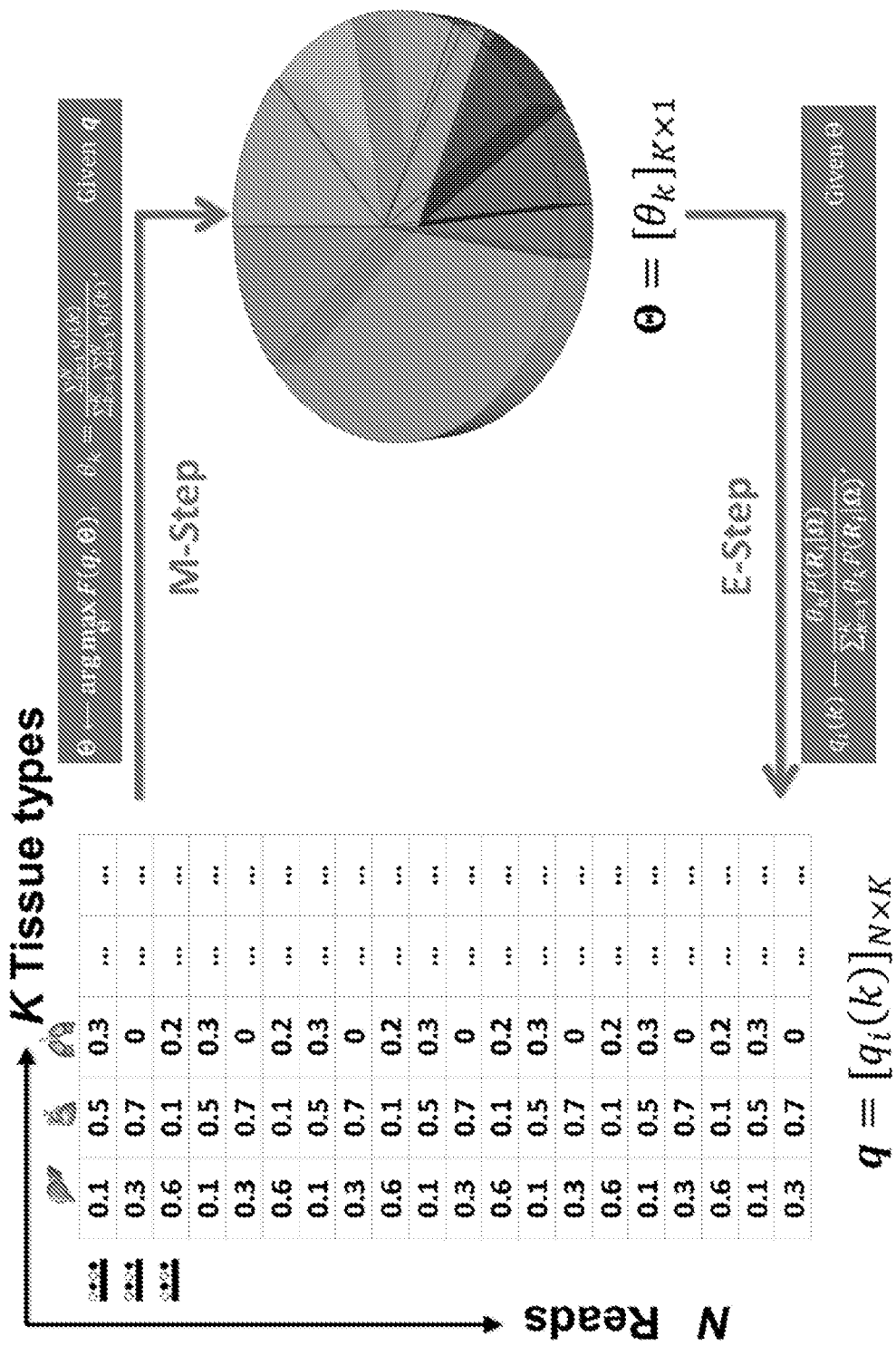
FIG. 6 depicts an exemplary embodiment, illustrating an EM algorithm's flowchart. For the new unknown tissue, its estimated methylation signature $m_j^{new}=f(q,R)$, where $f(q,R)$ is either Eq. (9) or Eq. (10), depending on which model of methylation signature is used

When methylation signature is modeled by each bin j (Model 1):

$$m_j^{new} = \frac{\sum_{\text{read } i \in \text{bin } j} q_i(\text{new}) |\text{methylated } CpG \text{ sites of read } i|}{\sum_{\text{read } i \in \text{bin } j} q_i(\text{new}) |\text{all } CpG \text{ sites of read } i|} \quad (10)$$

for each $t=1, \ldots, T+1$. Therefore, Eqs. (7), (8), (9) or (10) are the solutions of the E-step and M-step, respectively. According the EM algorithm, starting with a random $\Phi^{(0)}$ and $\Omega^{new\,(0)}$ then iteratively performing Eqs. (7), (8), (9) or (10) can converge to a local maximum of the log-likelihood function. Therefore, we need to run the EM algorithm with different initial values for many times and choose the solution with the maximum log-likelihood. An illustration of this procedure is shown in FIG. 6.

In the E-step of the above EM algorithm of Eq. (7), a key calculation is $P(R_i \mid \Omega^t)$, which is the tissue-of-origin likelihood of a cfDNA read $R_i$ for tissue t. According to different models of methylation signatures $\Omega^t$ (as listed in FIG. 4), we have the following methods of calculating $P(R_i \mid \Omega^t)$.

Epiallele Model without Considering Inter-Individual Variances of $\Omega^t$:

We can simply use the relative frequency in the frequency histogram of methylation status as $P(R_i \mid \Omega^t)$. This is illustrated in Model 1 of FIG. 11.

CpG Site Model without Considering Inter-Individual Variances of $\Omega^t$:

Let $m^t = (m_1^t, m_2^t, \ldots, m_M^t)$ denote the average methylation rate ($m_j^t$) of each tissue-specific CpG site j ($1 \leq j \leq M$) for tissue t. If we model the methylation status (denoted as $r_{ij}=0$ or 1) of cfDNA read $R_i$ in the j-th CpG site follows the Bernoulli distribution $r_{ij} \sim \text{Bernoulli}(m_j^t)$, as shown in Model 2 of FIG. 11, $P(R_i \mid \Omega^t)$ can be calculated as $$P(R_i \mid \Omega^t) = \prod_{\substack{j=1 \\ j \text{ is covered by } R_i}}^{M} (m_j^t)^{r_{ij}} (1 - m_j^t)^{1-r_{ij}} \quad (11)$$

Where $r_{ij}$ is the j-th element of the row vector $R_i$.

CpG Site Model with Inter-Individual Variances of $\Omega^t$:

If we consider the inter-individual variances of the tissue-specific methylation rate of the j-th CpG site, we can model the Bernoulli random variable $r_{ij}$ with the Beta prior $m_j^t \propto \text{Beta}(\alpha_j^t, \beta_j^t)$, where the inter-individual variance of each $m_j^t$ is characterized by the Beta distribution with the parameters $\beta_j^t$ and $\beta_j^t$. Then $P(R_i \mid \Omega^t)$ can be calculated as (shown in Model 2 of FIG. 4)

$$P(R_i \mid \Omega^t) = \prod_{\substack{j=1 \\ j \text{ is covered by } R_i}}^{M} \frac{B(r_{ij} + \alpha_j^t, 1 - r_{ij} + \beta_j^t)}{B(\alpha_j^t, \beta_j^t)} \quad (11)$$

Bin Model without Considering Inter-Individual Variances of $\Omega^t$:

Let the methylation rate $m^t$ represent $\Omega^t$ in a bin. $P(R_i \mid \Omega^t)$ is a simplified version of Eq. (11) and can be calculated as (shown in Model 3 of FIG. 11)

$$P(R_i \mid \Omega^t) = \prod_{\substack{j=1 \\ \text{CpG site } j \text{ is covered by } R_i}}^{M} (m^t)^{r_{ij}} (1-m^t)^{1-r_{ij}} \quad (12)$$

Bin Model with Inter-Individual Variances of $\Omega^t$:

If we consider the inter-individual variances of the tissue-specific methylation rates $m^t$ of each bin, we can model the Bernoulli random variable $r_{ij}$ with the Beta prior $m^t \sim \text{Beta}(\alpha^t, \beta^t)$, where the inter-individual variance of each $m^t$ is characterized by the Beta distribution with the parameters $\alpha^t$ and $\beta^t$. Then $P(R_i \mid \Omega^t)$ can be calculated as (shown in Model 1 of FIG. 4)

$$P(R_i \mid \Omega^t) = \prod_{\substack{j=1 \\ \text{CpG site } j \text{ is covered by } R_i}}^{M} \frac{B(r_{ij} + \alpha^t, 1 - r_{ij} + \beta^t)}{B(\alpha^t, \beta^t)} \quad (13)$$

Example 3

Sample Collection and Analysis

Collecting DNA Methylation Data from Public Tumor Tissue Samples for Characterizing Methylation Signatures:

We collect all the publically available methylation data of both solid tumors and plasma cfDNA samples of normal people and cancer patients. Since the majority of tumor methylation profiles of the TCGA (The Cancer Genome Atlas) database are assayed by Infinium HumanMethylation450 microarray, we collect only methylation microarray data for solid tumors, covering 2 tissue types: liver (LIHC) and lung (cancer types include LUAD and LUSC). As of December 2013, we collected 169 LIHC tumors, and 450/359 LUAD/LUSC tumors. Note that we used only normal tissue samples from RoadMap project. In future, we will use the microarray methylation data of solid normal tissue samples from GEO and TCGA.

Here, LIHC stands for Liver Hepatocellular Carcinoma; LUAD stands for Lung Adenocarcinoma; and LUSC stands for Lung Squamous Cell Carcinoma.

Building CpG Clusters (Features):

Most public methylation data (TCGA and GEO) are Infinium HumanMethylation450 microarray data. In this study, we used as features the clusters of CpG sites (covered by probes), i.e., genomic regions of variable sizes. It is due to the low sequencing coverage of patients' plasma cfDNA data (~4× on average) which are from the only source: Chan et al. (2013). The CpG clusters can cover more sequencing reads and thus can generate more reliable methylation measurements than using individual CpG sites. In detail, each CpG cluster is a genomic bin by grouping all individual adjacent CpG probes (sites) within this bin, which must satisfy two criteria: (i) the genomic distance between two adjacent CpG probes in a cluster is less than 700 bp, and (ii) each cluster has at least 10 CpG probes. The two numbers are carefully chosen to make as many CpG probes (of microarray data) clustered as possible for sufficient coverage of WGBS reads, while keeping the cluster's genomic size as small as possible. It is observed that most clusters are associated with only one gene, according to the annotation of the probes. This yields 11,572 CpG clusters, which include about ⅓ of all the CpG probes on the Infinium HumanMethylation450 microarray. These CpG clusters are used for selecting signature features in Component 1 of the method shown in FIG. 12.

Collecting DNA Methylation Data of Public Plasma cfDNA Samples:

The only major public data source of methylation data of plasma cfDNA samples we can find are from a recent study of plasma cfDNA methylation analysis[3]. In this study, Chan et al. (2013) has deposited their whole-genome bisulfite sequencing (WGBS) data of a set of plasma samples, including 32 normal people, 8 patients infected by chronic hepatitis B virus (HBV), 26 liver cancer patients, and 4 lung cancer patients, which are in total 70 plasma samples. Note that these WGBS data have low sequencing coverage (~4× on average). Bismark is employed to align the reads to the reference genome HG19 and call the methylated cytosines[4]. After the removal of PCR duplications, the numbers of methylated and unmethylated cytosines are counted for each CpG site. Then a CpG cluster's methylation level is calculated as the ratio between the total numbers of methylated and all cytosines within the cluster.

Methylation Cancer-Specific and Tissue-Specific Signatures:

We used both 16 normal people's plasma cfDNA WGBS data (from Chan et al. (2013) data) and solid tumors (from TCGA data) to obtain 1,452 cancer-specific methylation signatures which are modeled by variable-size bins (CpG clusters defined above and Model 1 of FIG. 4). For tissue-specific methylation signatures, we used 5,820 biomarkers learned from RoadMap data by Sun et al. (2015), which include 14 tissues and are modeled by 500 bp bins. These biomarkers are learned from only one individual in RoadMap data, not from a population.

Please note that in this preliminary results, we did not include the new unknown tissue type into the cfDNA composition inference algorithm in Step 3. In future work, we will use them.

Example 4

Prediction Performance

Results of Simulated Methylation Data of cfDNA Cancer Patients

We simulated the WGBS data of a patient's plasma cfDNA sample, by mixing the aligned reads from a healthy plasma sample's WGBS data and a solid tumor sample's WGBS data, with predefined sequencing coverage ~2× and at 8 different tumor DNA burdens: 0.5%, 0.8%, 1%, 3%, 5%, 10%, 15% and 20%. We used 4 normal plasma samples (from Chan et al. (2013)), 1 solid lung tumor sample (from TCGA), and 1 solid liver tumor sample (from Chan et al. (2013)). In total, there are 4×(1+1)×8=64 simulated cancer patients' plasma samples.

Figure 8:
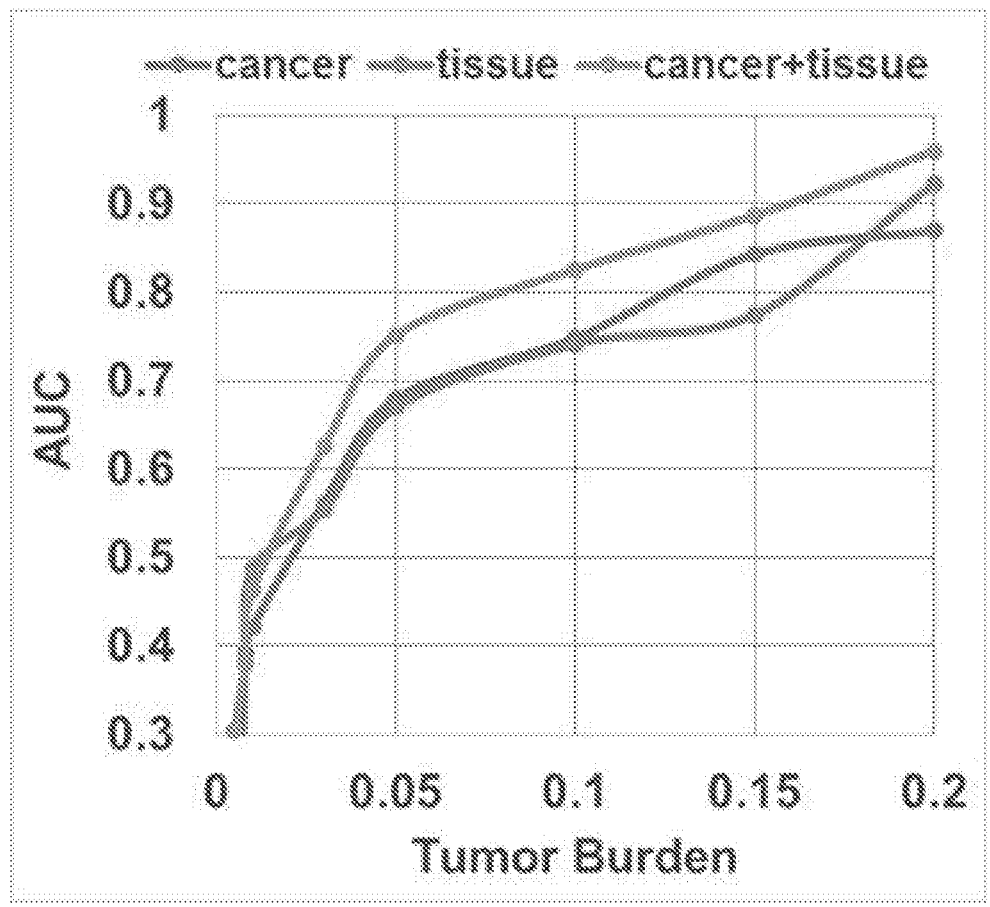
FIG. 8 depicts an exemplary embodiment, illustrating healthy-or-cancer prediction performance (area under the curve: AUC) of simulation data with different tumor burdens in plasma cfDNAs.

By including the rest of 12 normal plasma samples (i.e., out of 32 samples, 16 samples were used for learning signatures and 4 samples for generating simulation data), we perform our method that gives a prediction score to each simulated sample or each of 12 normal plasma sample. Then we evaluate the healthy-or-cancer prediction performance by the Area Under Curve (AUC) of Receiver Operating Characteristic (ROC). In FIG. 8, we plotted the AUCs for simulation data with different tumor DNA fractions. For representation simplicity, the cancer compositions are called "cancer dimension", while the normal tissue compositions are called "tissue dimension". It can be observed that using both dimensions (gray line) outperforms using either cancer-dimension (blue line) or tissue-dimension (orange line) at all tumor burdens. In addition, our method with two dimensions can achieve the AUC around 75% at the tumor burden 5% of plasma cfDNA.

Results of Real cfDNA Cancer Patients

As aforementioned, we used 16 normal plasma samples (out of all 32 normal samples in Chan et al. (2013) data) for deriving cancer-specific methylation signatures. Therefore, in this experiment, we randomly selected 8 out of the rest 16 normal plasma samples for building the empirical distribution of tissue and tumor compositions for normal plasma population that is used in Z-score based integration method. Then we used the last 8 normal samples in test set. The test set also includes 8 plasma samples which were infected by chronic hepatitis B virus (we regard them as noncancerous or normal samples), 26 liver cancer patients, and 4 lung cancer patients. Because of the random partition of normal plasma samples, the test set is different for every random partition. So we evaluate the method on different test sets and use the average performance score (AUC or confusion matrix) as the final result.

Figure 9:
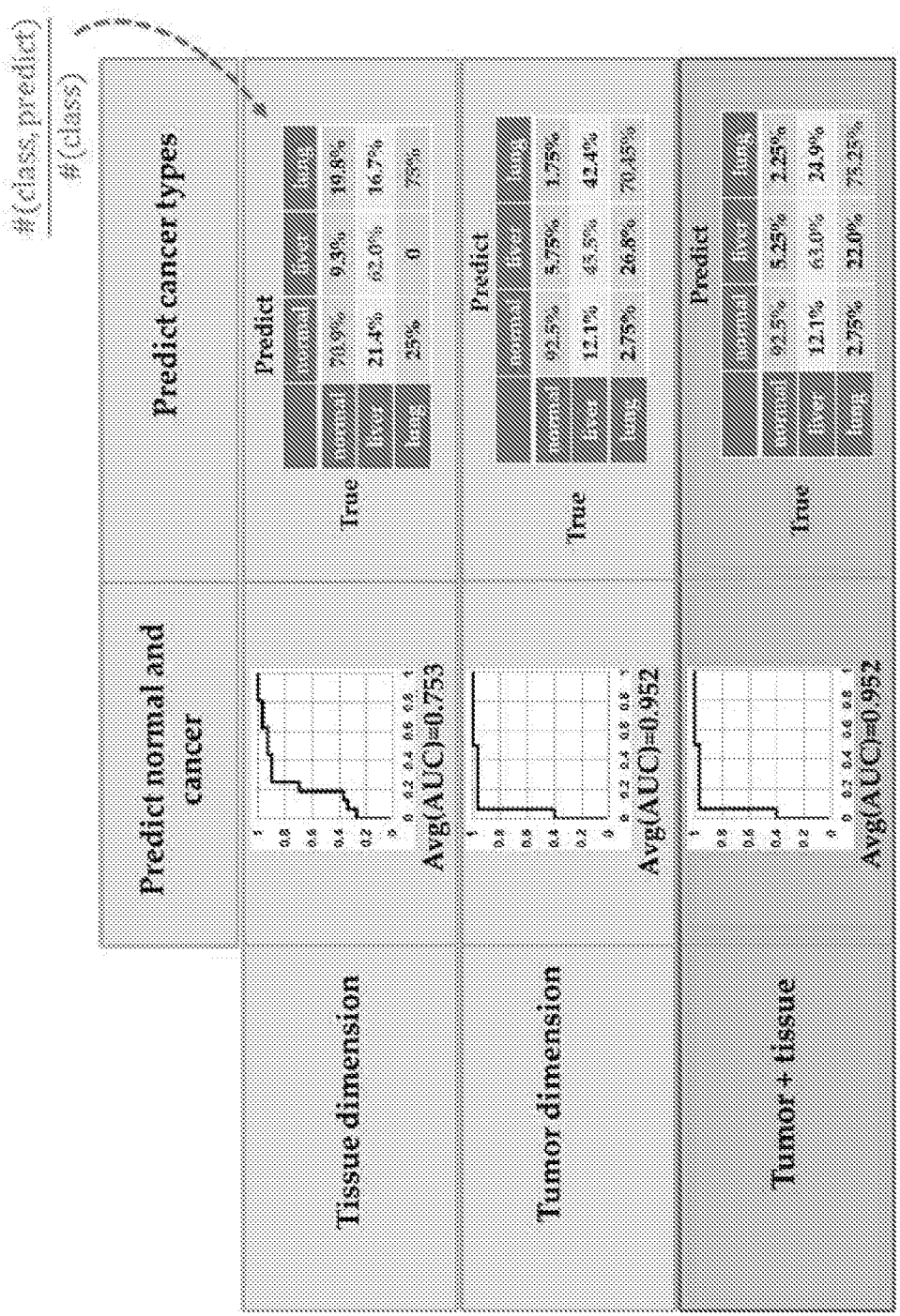
FIG. 9 depicts an exemplary embodiment, illustrating prediction performance of using only single dimension and both dimensions for two types of classification task: (i) binary classification—a new patient is healthy or gets cancer; and (ii) multi-class classification—a new patient is classified to normal, liver cancer or lung cancer. We report the prediction performance averaged over different random test set (i.e., AUC and confusion matrix). In the confusion matrix, each entry value in a true class (t) and predicted class p is calculated as a fraction.

We evaluate two prediction tasks: (i) binary classification—a new patient is healthy or gets cancer; and (ii) multi-class classification—a new patient is classified to normal, liver cancer or lung cancer. The results are shown in FIG. 9. We observe the following conclusions:

Tissue dimension works better than tumor dimension in multi-class classification task, but worse in binary classification task. This is not surprising, because (i) the carcinogenesis mechanisms are common to many cancer types, which make cancer methylation signatures are not so differential between cancer types; on the contrary, (ii) as evidenced by literatures, many methylation patterns are tissue-specific and can contribute to tissue-of-origin prediction.

Integrating both dimensions can further increase multi-classification classification task. This observation highlights the importance of integrating as many tumor-relevant clues as possible in plasma cfDNAs.

Example 5

Monitoring Cancer Patients

In addition to cancer diagnosis, our method is also effective in monitoring the cancer progression of patients by their prediction score. The prediction score intuitively describes how far the tumor and tissue composition of the patient's plasma cfDNAs is from normal people. Therefore, the larger the prediction score is, the later cancer stage (or the more serious) the patient is.

Two liver patients with their longitudinal plasma cfDNA WGBS data (from Chan et al. (2013) data) were used. Before tumor resection, Patient 1 (sample ID: TBR36) has the prediction score 34.2, much higher than average score (i.e., zero) of normal people. After 3 days, 3/6/12 months following surgery, the prediction score immediately return to the normal range (around zero). As shown in FIG. 10, this is also observable for the composition of 14 tissues in this patient's plasma cfDNA sample. However, Patient 2 (sample ID: TBR34) still keeps high prediction scores at 3 days and 2 months after operation, 10.8 and 12.9 respectively. This patient passed away later.

Example 6

Material and Methods for Examples 7-9

Overview

The goal of this approach is to classify each read (in the methylation marker regions) into either the tumor-derived cfDNA class (abbreviated as class T) or the normal-plasma-derived cfDNA class (abbreviated as class N). Here, one type of cancer, liver cancer, is the focus but the method can be generalized to any cancer type. This approach comprises three major steps: (i) Identifying the DNA methylation signatures of liver cancer. The methylation markers of liver cancer were derived based on DNA methylation data of liver tumors and their matched normal tissues as well as normal plasma cfDNA samples. The vast amount of methylation data was collected from the public database TCGA (The Cancer Genome Atlas (Weinstein et al. (2013)) and recent literatures Chan et al. (2013). (ii) Calculating the likelihood for a read to harbor a methylation signature. Methylation sequencing was performed on the plasma cfDNA sample of a new patient. Sequencing reads were obtained of those cfDNA fragments that fall into the genomic regions of selected markers. To account for data uncertainty and inter-individual methylation variances in markers, the likelihood of each read to come from each class was calculated. (iii) Inferring cfDNA composition. The likelihood of each read to come from each class can be used to derive the tumor burden in cfDNAs. FIG. 21 gives an overall picture of our approach, and we detail individual steps in the sections below.

Identify and Characterize Methylation Markers Specific to Liver Cancer

A methylation marker includes two kinds of information: its genomic region and methylation patterns in both solid tumor samples (class T) and normal plasma cfDNA samples (class N). To take advantage of the large amount of public methylation data from TCGA that were mainly generated by the microarray platform, the following two-step procedure was developed to obtain the liver-cancer-specific methylation markers.

Identify Genomic Markers for Liver Cancer

Only genomic regions that are covered by sufficient microarray probes qualified as potential markers. Therefore, the definition of CpG clusters in our recent work (Kang et al. (2017), which is hereby incorporated by reference) is used to identify all potential genomic regions. See the Examples below for details. Among all potential regions, those regions were selected whose methylation levels can differentiate most liver tumor samples from not only their matched normal liver tissues but also from normal plasma samples. This task inherently includes two steps: (i) Selecting those "frequently differential methylation regions (FDMR)", in which the methylations are differential (greater than a cutoff) between matched tumor and normal tissues in more than half of the matched pairs. This step can remove markers specific to liver tissues, but retain markers specific to liver cancer. (ii) Selecting those FDMRs that can distinguish tumor samples from normal plasma samples, i.e. the difference between the medians of its methylation levels in two classes is greater than a cutoff. This step ensures that the tumor methylation signal can be identified in blood. Given a fixed sequencing coverage of cfDNAs, the more markers used (that is, the larger the panel size), the lower quality these markers may have, but the more tumor-derived cfDNA reads that may be identified. Therefore, there is a tradeoff between the markers' quality and the amount of tumor cfDNA signals that can be used. In this work, because all public plasma cfDNA samples have low sequencing coverages (1x~3x), the cutoff of the methylation difference in both steps was chosen as 0.2 in order to keep relatively good marker quality and maintain a large enough size for the methylation marker panel to capture sufficient tumor cfDNAs at this low sequencing coverage.

Characterize Methylation Patterns

In each marker region identified in Step 1, the inter-individual variance of methylation levels in each class (T and N) are considered. Given a region, the methylation levels of all samples in a class were modelled to follow a Beta distribution Beta(η,ρ), which has been widely used in methylation data analyses. Specifically, a marker k is associated with two methylation patterns, i.e., Beta($\eta_k^T, \rho_k^T$) for the class T and Beta($\eta_k^N, \rho_k^N$) for the class N. Note that $\eta_k^c$ and $\rho_k^c$ are two shape parameters (usually denoted α and β) of a Beta distribution, but here we used the symbols η and ρ to avoid the confusion with α-value and β-values defined in Introduction section. The parameters of a Beta distribution can be easily learnt from the sample population of a class, using either the method of moments or maximum likelihood (Bowman et al. (2007). To simplify notation, the methylation pattern of marker k for class T as $m_k^T$≡Beta($\eta_k^T, \rho_k^T$), and for class N as $m_k^N$ ≡Beta($\eta_k^N, \rho_k^N$) was denoted.

Calculate the Class-Specific Likelihood of Each cfDNA Sequencing Read

The goal was to classify each cfDNA read as class T or N, based on the joint-methylation-status of multiple CpG sites on the read. The joint-methylation-status in a cfDNA read is denoted as r=($r_1, r_2, \ldots$), where the binary value r=1 or 0 represents methylated or unmethylated status of the CpG site j in read r. This binary vector r was modelled by the Beta-Bernoulli distribution (Shah et al. (2015)). Specifically, given a methylation pattern m-Beta(η,ρ) of the marker where read r falls into, the methylation status $r_j$ of each CpG site j in the read is distributed as $r_j$~Bernoulli(p), where p is the prior of average methylation rate of CpG sites within the marker and follows the Beta prior distribution p~Beta(η,ρ). Using this statistical model, the likelihood of the joint methylation status in read r=($r_1, r_2, \ldots$), given the methylation pattern m, can be calculated as below:

$$P(r|m) = \prod_j P(r_j | \text{Beta}(\eta, \rho))$$
$$= \prod_j \int_0^1 \text{Bounoulli}(r_j | p)\text{Beta}(p | \eta, \rho) dp$$
$$= \prod_j \int_0^1 p^{r_j}(1-p)^{1-r_j} \frac{p^{\eta-1}(1-p)^{\rho-1}}{B(\eta, \rho)} dp$$
$$= \prod_j \frac{B(r_j + \eta, 1 - r_j + \rho)}{B(\eta, \rho)}$$

where B(x,y) is the beta function. Therefore, for marker k with methylation pattern $m_k^T$ of class T and $m_k^N$ of class N, we can use the above formula to compute the class-specific likelihoods of read r, i.e., P(r|$m_k^T$) and P(r|$m_k^N$). Note that this likelihood calculation implements a probabilistic version of α-value for individual reads. An example is illustrated in FIG. 22.

Predict Tumor-Derived cfDNA Burden

As illustrated in FIG. 21, a probabilistic framework was developed to infer the tumor-derived cfDNA fraction (i.e. tumor burden), denoted as 0≤θ<1, by classifying cfDNA reads into two classes (class T for tumor-derived DNAs and class N for normal plasma cfDNAs), based on a set of markers associated with the methylation patterns of two classes. Denoted are the methylation patterns of all K markers as $\mathcal{M}$ ={($m_1^T, m_1^N$), . . . , ($m_k^T, m_k^N$), . . . , ($m_K^T, m_K^N$)}. We also denote the methylation sequencing data of a patient's cfDNAs as a set of N reads R=($r^{(1)}, \ldots, r^{(N)}$) that in total cover M CpG sites. For a read that is aligned to the region of marker k, we assume that it can come from one of two classes with the class-specific likelihood P(r|$m_k^c$), where $m_k^c$ is the methylation pattern of class c. Let θ be the tumor-derived cfDNA burden, so the fraction of normal cfDNA is 1–θ. It is desirable to estimate θ by maximizing the log-likelihood log P(R|θ, $\mathcal{M}$ ). This is a maximum likelihood estimation problem. The independence of each read was assumed (as widely adopted in literatures (Yuan et al. (2015), Landau et al. (2014)), P(R|θ, $\mathcal{M}$ )=$\Sigma_{i=1}^N$ P($r^{(i)}$|θ, $\mathcal{M}$ ). The likelihood P($r^{(i)}$|θ, $\mathcal{M}$ ) of read $r^{(i)}$ is expanded as follows:

$$P(r^{(i)}|\theta, \mathcal{M}) = \theta P(r^{(i)}|m_k^T) + (1-\theta)P(r^{(i)}|m_k^N)$$

Because P(R|θ, $\mathcal{M}$ ) has only one parameter θ to be estimated, a grid search can be applied to exhaustively enumerate all 1000 fraction values which are uniformly distributed between 0% and 100%, i.e., 0%, 0.1%, . . . , 0.99% and 100%. This method can get the global optimization at the precision of 0.1%, which we think is sufficient for capturing the tiny amount of tumor-derived cfDNAs. Because the grid search is computationally fast, the steps to determine θ at higher resolutions can be readily refined.

Removal of "Germline" Markers:

Above, a global tumor burden (θ) across all cancer-specific markers was estimated. The tumor burden (θ) can also be estimated only for a single marker. Ideally, for an early-stage cancer patient, the estimated θ should be a small number (e.g., <20%), either across all markers or in individual markers. However, in real cancer patient data, we observed a number of markers with individually estimated tumor burdens far larger than the global tumor burden. Therefore, cfDNA fragments harboring aberrant methylation in these "outlier" markers obviously do not come from cancerous cells, but likely from normal cells (e.g. white blood cells) due to inter-individual variance (e.g. age, environment exposure, or other diseases the person may have). Such methylation abnormalities are conceptually similar to "germline" mutations. Consequently, including these "germline" markers would impair the accuracy of tumor burden estimation. An iterative algorithm was designed to adjust the global tumor burden after identifying and removing "germline" markers. $\theta_k$ is denoted as the tumor burden at the marker k, to distinguish from the global burden θ obtained using all markers. The procedure of this algorithm is presented below:

Initialization—

Let $\mathcal{M}$ denote the set of markers used for θ estimation. Initially, all markers are pulled into $\mathcal{M}$ .

Remove "Germline" Markers—

Estimate $\theta_k$ of each marker k in $\mathcal{M}$ and calculate the standard deviation of all $\theta_k$, denoted as std($\theta_k$). Remove from $\mathcal{M}$ those markers whose $\theta_k$>θ+λstd($\theta_k$), where λ is an input fixed parameter.

Update θ—

Estimate the global burden θ using all markers of $\mathcal{M}$ updated in Step 1.

Iterate Steps 1 and 2, Until θ Converges.

The output θ is the adjusted global tumor burden after removing "germline" markers. The parameter λ of this algorithm controls how far the $θ_k$ of those "germline" markers deviates from the average θ. This parameter can be estimated using normal plasma cfDNA samples, because it is expected that the optimal λ should be able to adjust the global θ of the normal samples to be close to zero.

Methylation Data Collection, Generation and Processing

Data Collection:

We collected the methylation profiles of 49 solid liver tumor samples and their matched adjacent solid liver tissue samples from the TCGA database. All of these samples were assayed using the Infinium HumanMethylation450 microarray. For the plasma cfDNA samples, \the methylation sequencing data from Chan et al. (2013) and Sun et al. (2015) were used. They include the Whole Genome Bisulfite Sequencing (WGBS) data of plasma samples taken from 32 healthy people, 8 patients infected with chronic hepatitis B virus (HBV), and 29 liver cancer patients.

Data Generation:

Since the public WGBS data of plasma cfDNA samples have very low sequencing coverage (1×~3×), WGBS data of plasma cfDNA samples was generated, at higher coverage (~10× on average), from two healthy people; and generated WGBS data of solid tumor samples from two cancer patients, in order to simulate higher-coverage cfDNA WGBS data from cancer patients. Blood samples were centrifuged at 1600×g for 10 minutes and then the plasma was transferred into new microtubes and centrifuged at 16,000×g for another 10 minutes. The plasma was collected and stored at −80° C. cfDNA was extracted from 5 ml plasma using the Qiagen QIAamp Circulating Nucleic Acids Kit and quantified using a Qubit 3.0 Fluoromter (Thermo Fisher Scientific). Bisulfite conversion of cfDNA was performed using the EZ-DNA-Methylation-GOLD kit (Zymo Research). After that, an Accel-NGS Methy-Seq DNA library kit (Swift Bioscience) was used to prepare the sequencing libraries. The DNA libraries were then sequenced with 150-bp paired-end reads. For the solid tumor samples, bisulfite conversion was performed with the EZ-DNA-Methylation-GOLD kit (Zymo Research), and the sequencing libraries were prepared using the TruSeq DNA Methylation Kit. The DNA libraries were then sequenced with 150-bp paired-end reads using HiSeq X (Illumina).

Processing Methylation Microarray Data:

The microarray data (level 3 in TCGA database) provide the methylation levels of individual CpG sites. The methylation level of a CpG cluster is defined as the average methylation level of all CpG sites in the cluster. A cluster's methylation level is marked as "not available" (NA) if more than half of its CpG sites do not have methylation measurements.

Processing WGBS Data:

Bismark (Krueger et al. (2011)) was used to align the reads to the reference genome hg19 and call the methylated cytosines. After the removal of PCR duplicates, the numbers of methylated and unmethylated cytosines were counted for each CpG site. The methylation level of a CpG cluster is calculated as the ratio between the number of methylated cytosines and the total number of cytosines within the cluster. However, if the total number of cytosines in the reads aligned to the CpG cluster is less than 30, the methylation level of this cluster is treated as NA (Not Available). This WGBS data processing procedure is used for calculating the average methylation level of a CpG cluster in normal plasma samples that are used for identifying methylation markers. When a plasma cfDNA sample is used as test data, the joint-methylation-status of all CpG sites of individual sequencing reads that are aligned to the regions of the marker panel from Bismark's output was extracted, then fed this information into CancerDetector as its input data. Because the sequencing coverage of real data is low, in this work, we used all reads covering at least one CpG site. For the cfDNA methylation data with high coverage, we can filter out those reads covering <3 CpG sites to improve the input data quality.

Example 7

Identify Methylation Markers Specific to Liver Cancer

Defining all Genomic Regions Eligible to Serve as Methylation Markers:

Our training data are from the TCGA solid tissues, measured by the Infinium HumanMethylation450 microarray with ~450,000 CpGs. However, our testing data (Chan et al. (2013), Sun et al. (2015)) are WGBS data with very low sequencing coverage. Therefore, the CpG sites were grouped into CpG clusters in order to use more mappable reads from the testing data. For a CpG site covered by a probe on the microarray, the region 100 bp up- and downstream were defined as its flanking region and assume that all CpG sites located within this region have the same average methylation level as the CpG sites covered by probes. Two adjacent CpG sites are grouped into a CpG cluster if their flanking regions overlap. Finally, only those CpG clusters containing at least three CpGs covered by microarray probes are used, in order to achieve robust measurement of methylation levels. This procedure yielded 42,374 CpG clusters, which together include about one-half of all the CpG sites on the Infinium HumanMethylation450 microarray. Most of these clusters are each associated with only one gene. These CpG clusters are used for subsequent feature selection.

Selecting Liver-Cancer-Specific Markers and Characterizing their Patterns in Normal and Tumor Classes:

Given the 42,374 CpG clusters, the cancer-specific markers were selected by using the method described in Example 6 on the training data: (i) 49 pairs of solid liver tumors and their matched normal liver tissues and (ii) 75% of all the 32 healthy plasma samples. Note that the remaining 25% of healthy plasma samples are used as test data, and the healthy plasma samples were randomly partitioned in the ratio of 75/25 as the training/test data, respectively, 10 times. This indicates that there were 10 different sets of training/test data and each set can yield different selected markers and tumor burden estimation. Each set of training/test data and its result is called an experimental run. In each of the 10 runs, on average of 3,214 liver-cancer-specific markers (CpG clusters) were identified, and the majority of these markers were shared by all runs. The methylation patterns for each marker in the normal and tumor classes were classified as two Beta distributions, with learnt shape parameters that can capture the inter-individual variance of methylation levels within a class.

Example 8

Simulation Experiments Demonstrated the Ultrasensitivity of CancerDetector in Detecting Tumor cfDNAs The methylation data of a plasma cfDNA sample was simulated by sampling and mixing the methylation sequencing reads of two real samples, a normal plasma cfDNA sample and a solid tumor sample, at a variety of tumor burdens ($\theta$) and different sequencing coverages (c). This strategy can allow us to mimic real data and precisely control the tumor burden and sequencing coverage in the mixture samples, in order to test the power and requirement of the CancerDetector method, e.g. at what tumor burden and sequencing coverage can tumor-derived cfDNAs be detected. CancerDetector was compared with another probabilistic cfDNA deconvolution method, "CancerLocator" (Kang et al. (2017)) and USN 62/473,829, which is hereby incorporated by reference), that inventors recently developed and is so far the only method aimed at deconvoluting cancer signals from cfDNA methylation data. While CancerDetector is a read-based method, CancerLocator is based on traditional β-values by deconvolving β-values of markers in the cfDNAs as a linear combination of the β-values of two classes (tumor or normal cfDNAs).

To compare the sensitivity of the two methods in identifying a minor trace of tumor cfDNAs (i.e., $\theta \leq 5\%$), plasma cfDNA samples at 8 different tumor burdens ($\theta=0$, 0.1%, 0.3%, 0.5%, 0.8%, 1%, 3% and 5%), and 3 different sequencing coverages (c=2, 5, 10) were simulated. The real samples used in the simulation procedure are the WGBS data of two normal plasma samples (N1L and N2L) and of two solid liver tumor samples (HCC1 and HCC2). This experimental setting results in 8×3×2×2=96 mixed samples. FIG. 23 demonstrates the sensitivity of the two methods in detecting tumor cfDNAs, where scatter plots are shown for the predicted tumor burdens averaged over 10 experimental runs of the simulated samples with 8 given tumor burdens at three given sequencing coverages (2×, 5× and 10×). As clearly shown in FIG. 23, the blood tumor burdens predicted by CancerDetector 410 are highly consistent with the true values and have very low prediction variances: e.g., when using the highest sequencing coverage 10×, CancerDetector 410 achieved a Pearson's Correlation Coefficient (PCC) of 0.9974±0.0012 (P-value=7.2E-8±9.8E-8), averaged over 10 runs. The consistency increased with the sequencing coverage, i.e., average PCC=0.9811, 0.9959, 0.9974 and their associated P-values 2.5E-5, 6.0E-6, 9.8E-8 for the sequencing coverages of 2×, 5×, 10×, respectively. More importantly, it can be observed that CancerDetector 410 can (i) detect tumor cfDNAs with a low tumor burden ($\theta=1\%$) at low sequencing coverage (2×), and (ii) improve the detection limit from 1% to 0.3% when increasing the sequencing coverages (5× and 10×). On the other hand, the f-value-based method, CancerLocator 420, cannot detect any tumor DNAs when the tumor burden $\theta$ is <5% and 2× sequencing coverage, or $\theta<3\%$ with 5× coverage. Even with 10× sequencing coverage, its predictions are not stable (there is high prediction variance) and deviate strongly from the true tumor burdens. In summary, this result demonstrates that the read-based CancerDetector 410 method can sensitively detect a small amount of tumor cfDNAs, even at low sequencing coverage, and the prediction accuracy and stability increase with higher sequencing coverage.

Example 9

Testing on Real Data Confirmed the High Sensitivity of CancerDetector in Deconvoluting Tumor cfDNA A collection of public plasma samples (32 healthy people, 8 HBV carriers and 29 liver cancer patients) was collected from Chan et al. (2013) and Sun et al. (2015). These data have low sequencing coverages (1×~3×). The 32 healthy plasma samples were randomly split into training set (75%) and test set (25%) 10 times (runs). In each run, using the combined training set and TCGA microarray data of solid liver tumors and matched normal tissues, the liver-cancer-specific methylation markers were identified and then predicted tumor burdens in the test set: the plasma samples from 8 HBV carriers, 29 liver cancer patients, and the remaining 25% of healthy subjects. The performance of predicting tumor burdens can be measured by the Receiver Operating Characteristic (ROC) curve, where the sensitivity and specificity of separating cancer and non-cancer samples are calculated and plotted by using different tumor burden cutoffs. As shown in FIGS. 24A and 24B, the average ROC curve of CancerDetector 510 outperforms that of CancerLocator 520 in terms of both prediction performance and robustness (i.e., much lower standard deviations). For example, when we chose the point of the top-left corner in the ROC curve for determining the tumor burden threshold, at the specificity of 100% CancerDetector 510 can achieve an average sensitivity of 95.2% across 10 runs with standard deviation 3.2%; while the β-value based CancerLocator 520 method achieved on average a sensitivity of 74.1% with standard deviation 10.7% at the specificity of 100%. Note that there are at least 25 early-stage (Barcelona Clinic Liver Cancer stage A) patients among the 29 liver cancer patients. Testing only on the 25 early-stage cancer patients and healthy/HBV samples, at the specificity of 100% our method can also achieve an average sensitivity of 94.4% with a standard deviation of 3.7%; while CancerLocator 520 obtained a sensitivity of 74.4% with a standard deviation 10.0%. Summarizing the performance comparison using the Area Under Curve (AUC), our method can achieve an AUC of 0.988 averaged over 10 runs with standard deviation 0.004 for all real samples and an average AUC of 0.987 with standard deviation 0.005 for early-stage cancer patients; while CancerLocator 520 obtained a lower average AUC of 0.975 with standard deviation 0.014 for real samples and an average AUC of 0.975 with standard deviation 0.0143 for early-stage cancer patients. CancerDetector 510 correctly predicted the cfDNA tumor burdens of all eight chronic hepatitis B virus (HBV) samples to be the same range of the normal samples (i.e., close to zero) that are well distinguished from cancer samples. These results demonstrated that CancerDetector 510 can go beyond distinguishing healthy samples from cancer samples and handle more sophisticated scenarios, such as differentiating HBV carriers from cancer patients. Therefore, using real plasma samples we also demonstrated that the read-based CancerDetector method can more sensitively detect tumor cfDNAs.

In general, the predicted tumor burden correlates well with tumor size. As shown in FIG. 24C, among the 26 liver cancer patients with tumor size information, the PCC between the predicted tumor burden and tumor size is 0.87 (P-value=7.37e-09). Even after removing the three patients with the largest tumors (size>6 cm), we still get a relatively good PCC of 0.42 (P-value=4.61e-02).

CancerDetector can also be used for monitoring the cancer progression and treatment. We used two cancer liver patients from Chan et al. (2013) whose plasma samples were obtained before surgical tumor resection and at multiple time points after the surgery. The first patient survived beyond 12 months, while the second patient died of metastatic disease after the operation (Chan et al. (2013)). As shown in FIG. 25, the predicted blood tumor burdens are consistent with the treatment effects: the first patient's tumor burdens quickly fall into the normal range; while those of the second retain relatively high values after the surgery.

The success of early cancer detection largely relies on (i) the high-quality cancer-specific methylation markers, and (ii) the computational method for the ultra-sensitive detection of tiny amounts of tumor cfDNAs (usually <5%, or even <0.5% in early-stage cancer patients). In some embodiments, there is a method to deconvolute the tumor cfDNA out of total cfDNA at the resolution of individual reads. Compared with traditional cancer detection methods, our method has two advantages in identifying subtle tumor signals: (i) Exploit the pervasive nature of DNA methylation to significantly amplify aberrant cfDNA signals: As demonstrated in FIG. 1 and FIG. 20 and in our experimental results, the joint methylation status ($\alpha$-value) of multiple CpG sites in a read carries more sensitive tumor signals than the average methylation rate ($\beta$-value) of an individual CpG site. Our probabilistic method based on $\alpha$-value is particularly advantageous when tumor burdens and sequencing coverages are low. (ii) Jointly deconvolute tumor burden across all markers. Existing methods often focus on detecting tumor signals in single tumor markers, not aggregating signals from all markers (Sharma (2009), Sturgeon et al. (2009)). Alternatively, our method holds the belief that subtle tumor signals should occur at multiple places in the genome. Although our method can detect tumor cfDNA at the read level, all possible signals were combined to provide a robust and sensitive estimate of the tumor burden. The key considerations of (i) and (ii) promised, as demonstrated, that our method could do well for extremely low tumor burdens (<1%) at low or medium sequencing coverage (5× and 10×). Therefore, the approach holds the potential to largely reduce the cost of cancer detection.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

REFERENCES

Li, S. et al. Dynamic evolution of clonal epialleles revealed by methclone. *Genome Biol.* 15, 472 (2014)

Yuan, K. et al. BitPhylogeny: a probabilistic framework for reconstructing intra-tumor phylogenies. *Genome Biol.* 16, 36 (2015).

Zheng, X. et al. MethylPurify: tumor purity deconvolution and differential methylation detection from single tumor DNA methylomes. *Genome Biol.* 15, 419 (2014).

Sun, K. et al. Plasma DNA tissue mapping by genome-wide methylation sequencing for noninvasive prenatal, cancer, and transplantation assessments. *Proc. Natl. Acad. Sci. U.S.A* 112, E5503-12 (2015).

Houseman, E. A. et al. DNA methylation arrays as surrogate measures of cell mixture distribution. *BMC Bioinformatics* 13, 86 (2012).

Koestler, D. C. et al. Blood-based profiles of DNA methylation predict the underlying distribution of cell types: a validation analysis. *Epigenetics* 8, 816-26 (2013).

Koestler, D. C. et al. Peripheral blood immune cell methylation profiles are associated with nonhematopoietic cancers. *Cancer Epidemiol. Biomarkers Prev.* 21, 1293-302 (2012).

Chan, K. C. A. et al. Noninvasive detection of cancer-associated genome-wide hypomethylation and copy number aberrations by plasma DNA bisulfite sequencing. *Proc. Natl. Acad. Sci. U.S.A* 110, 18761-8 (2013).

Bettegowda, C. et al. (2014) Detection of circulating tumor DNA in early- and late-stage human malignancies. Sci. Transl. Med., 6, 224ra24.

Newman, A. M. et al. (2014) An ultrasensitive method for quantitating circulating tumor DNA with broad patient coverage. Nat. Med., 20, 548-54.

Newman, A. M. et al. (2016) Integrated digital error suppression for improved detection of circulating tumor DNA. Nat. Biotechnol., 34, 547-55.

Burrell, R. A. et al. (2013) The causes and consequences of genetic heterogeneity in cancer evolution. Nature, 501, 338-345.

Turner, N.C. et al. (2012) Genetic heterogeneity and cancer drug resistance. Lancet Oncol., 13, e178-e185.

Greenman, C. et al. (2007) Patterns of somatic mutation in human cancer genomes. Nature, 446, 153-158.

Schmitt, M. W. et al. (2012) Implications of genetic heterogeneity in cancer. Ann. N. Y. Acad. Sci., 1267, 110-116.

Baylin, S. B. et al. (2001) Aberrant patterns of DNA methylation, chromatin formation and gene expression in cancer. Hum. Mol. Genet., 10, 687-92.

Cheishvili, D. et al. (2015) DNA demethylation and invasive cancer: implications for therapeutics. Br. J. Pharmacol., 172, 2705-15.

Roy, D. M. et al. (2014) Driver mutations of cancer epigenomes. Protein Cell, 5, 265-96.

Plass, C. et al. (2013) Mutations in regulators of the epigenome and their connections to global chromatin patterns in cancer. Nat. Rev. Genet., 14, 765-80.

Smith, L. T. et al. (2007) Unraveling the epigenetic code of cancer for therapy. Trends Genet., 23, 449-56.

Sigalotti, L. et al. (2007) Epigenetic drugs as pleiotropic agents in cancer treatment: biomolecular aspects and clinical applications. J. Cell. Physiol., 212, 330-44.

Kang, S. et al. (2017) CancerLocator: non-invasive cancer diagnosis and tissue-of-origin prediction using methylation profiles of cell-free DNA. Genome Biol., 18, 53.

Cancer Genome Atlas Research Network, Weinstein, J. N. et al. (2013) The Cancer Genome Atlas Pan-Cancer analysis project. Nat. Genet., 45, 1113-20.

Bowman, K. O. et al. (2007) The beta distribution, moment method, Karl Pearson and RA Fisher. Far East J. Theor. Stat., 23, 133-164.

Shah, A. et al. (2015) An empirical study of stochastic variational algorithms for the Beta Bernoulli process. In International Conference on Machine Learning (ICML).

Landau, D. A. et al. (2014) Locally Disordered Methylation Forms the Basis of Intratumor Methylome Variation in Chronic Lymphocytic Leukemia. Cancer Cell, 26, 813-825.

Krueger, F. et al. (2011) Bismark: a flexible aligner and methylation caller for Bisulfite-Seq applications. Bioinformatics, 27, 1571-2.

Sharma, S. (2009) Tumor markers in clinical practice: General principles and guidelines. Indian J. Med. Paediatr. Oncol., 30, 1.

Sturgeon, C. M. et al. (2009) Use of tumor markers in clinical practice: quality requirements American Association for Clinical Chemistry.

Landan, G. et al. (2012) Epigenetic polymorphism and the stochastic formation of differentially methylated regions in normal and cancerous tissues. Nat. Genet., 44, 1207-14.

Li, S. et al. (2016) Distinct evolution and dynamics of epigenetic and genetic heterogeneity in acute myeloid leukemia. Nat. Med., 22, 792-9.

Swanton, C. et al. (2014) Epigenetic noise fuels cancer evolution. Cancer Cell, 26, 775-6.

Guo, S. et al. (2017) Identification of methylation haplotype blocks aids in deconvolution of heterogeneous tissue samples and tumor tissue-of-origin mapping from plasma DNA. Nat. Genet., 49, 635-642.

We claim:

1. A method for treating a subject with a cancer, comprising:

identifying a plurality of CpG cluster features of a cancer type t, wherein the plurality of CpG cluster features has a total number K of CpG cluster features, K being a positive integer;

obtaining a cell-free DNA (cfDNA) methylation profile of the subject;

estimating a methylation level $x_k$ for each of the plurality of CpG cluster features in the cfDNA methylation profile of the subject, wherein k=1, 2, . . . K;

determining a circulating tumor DNA (ctDNA) burden coefficient θ in the cfDNA methylation profile of the subject, wherein 0≤θ≤1;

calculating a prediction score λ using the ctDNA burden coefficient θ, the cancer type t, and the plurality of methylation levels $x_k$;

determining that the subject has the cancer type t, when the prediction score λ is greater than a pre-determined threshold; and administering a treatment to the subject based on the determining that the subject has the cancer type t, wherein the treatment comprises a member selected from the group consisting of a chemotherapy, a radiation therapy, an immunotherapy, and a tumor resection.

2. The method of claim 1, wherein identifying the plurality of CpG cluster features further comprises:

determining a first methylation level of a CpG cluster in a non-cancerous methylation profile;

determining a second methylation level of the CpG cluster in a cancerous methylation profile;

determining a methylation range coefficient MR based at least in part on a difference between the first methylation level and the second methylation level; and identifying the CpG cluster as a CpG cluster feature, if the methylation range coefficient MR is greater than a pre-determined MR threshold.

3. The method of claim 1, wherein estimating the methylation level $x_k$ for each of the plurality of CpG cluster features further comprises:

(i) estimating a methylation level $x_k$ of a specific CpG cluster using a number of methylated cytosines $m_k$ and a total number of cytosines $n_k$ within the specific CpG cluster, or (ii) deriving a probability density function describing the methylation level $x_k$ at least in part by convolving a first beta distribution function of a non-cancerous methylation profile and a second beta distribution function of a cancerous methylation profile.

4. The method of claim 1, wherein the ctDNA burden coefficient θ is determined using a global optimization estimation, wherein the global optimization estimation comprises minimizing an error value according to an error function evaluated at a plurality of different pre-defined θ values.

5. The method of claim 1, wherein the cancer type t is determined using a global optimization estimation, wherein the global optimization estimation comprises minimizing an error value according to an error function evaluated at a plurality of different pre-defined t values.

6. The method of claim 1, wherein the prediction score λ is determined using a maximum likelihood estimation, based at least in part on the ctDNA burden coefficient θ, the cancer type t, and the plurality of methylation levels $x_k$.

7. The method of claim 1, wherein the treatment comprises the chemotherapy.

8. The method of claim 7, wherein the chemotherapy is selected from the group consisting of an alkylating agent, an anthracycline, an epothilone, a histone deacetylase inhibitor, a Topoisomerase I inhibitor, a Topoisomerase II inhibitor, a kinase inhibitor, a nucleotide analog, nucleotide precursor analogs, a peptide antibiotic, a platinum-based anti-neoplastic, a retinoid, and a *vinca* alkaloid.

9. The method of claim 1, wherein the treatment comprises the immunotherapy.

10. The method of claim 9, wherein the immunotherapy is selected from the group consisting of a cellular therapy, an antibody therapy, and a cytokine therapy.

11. The method of claim 1, further comprising calculating the prediction score λ, according to:

$$\lambda = \frac{1}{K}[\log L(\hat{\theta}, \hat{t} \mid M, N) - L(\theta = 0 \mid M, N)]$$

wherein L is a maximum likelihood function, wherein $\hat{\theta}$ is an optimized value of the ctDNA burden coefficient θ, wherein $\hat{t}$ is an optimized value of the cancer type t, wherein M is a function of $X_k$, and wherein N is a function of $X_k$.

12. A method for treating a subject with a cancer, comprising:

determining a set of K DNA methylation marker regions of a cancer type t, K being a positive integer, wherein the set of K DNA methylation marker regions comprises CpG clusters that correspond to DNA methylation markers of the cancer type t;

obtaining a tumor class methylation pattern of each of the K DNA methylation marker regions, wherein the tumor class methylation pattern is expressed as $m_k^T$, wherein m denotes a marker region, wherein T denotes a tumor class, wherein k=1, 2, . . . K, and wherein the tumor class methylation pattern comprises a DNA methylation pattern derived from tumor cells of the cancer type t;

retrieving a normal class methylation pattern of each of the K DNA methylation marker regions, wherein the normal class methylation pattern is expressed as $m_k^N$, wherein m denotes a marker region, wherein N denotes a normal class, wherein k=1, 2, . . . K, and wherein the normal class methylation pattern comprises a cfDNA methylation pattern derived from cfDNA of non-cancerous cells;

obtaining a number of sequencing reads N of a cell-free DNA (cfDNA) methylation profile from a cfDNA sample of the subject, N being a positive integer;

calculating determining a circulating tumor DNA (ctDNA) burden θ based at least in part on the sequencing reads of the cfDNA methylation profile, the tumor class methylation pattern $m_k^T$, and the normal class methylation pattern $m_k^N$, wherein k=1, 2, . . . K;

determining that the subject has the cancer type t, when the ctDNA burden θ is greater than a pre-determined threshold; and administering a treatment to the subject based on the determining that the subject has the cancer type t, wherein the treatment comprises a member selected from the group consisting of a chemotherapy, a radiation therapy, an immunotherapy, and a tumor resection.

13. The method of claim 12, further comprising:

determining a methylation status in a sequencing read, the methylation status of the sequencing read being expressed as $r=(r_1, r_2, \ldots, r_j, \ldots, r_L)$, wherein j=1, 2, . . . L, wherein $r_j$ is binary, wherein $r_j=1$ represents a CpG at site j being methylated in the sequencing read, wherein $r_j=0$ represents a CpG at site j being unmethylated in the sequencing read, and wherein $r_j=NA$ represents a CpG at site j as not being covered by a sequencing read.

14. The method of claim 13, wherein the methylation status $r_j$ of a CpG at site j in a sequencing read of the cfDNA methylation profile comprises a Bernoulli distribution expressed as $r_j \sim$ Bernoulli(p), wherein p is a methylation rate of a CpG at site j, wherein p follows a Beta prior distribution.

15. The method of claim 14, further comprising:

calculating a likelihood P(r|m) of the methylation status of the sequencing read $r=(r_1, r_2, \ldots)$ given a methylation pattern m, wherein the likelihood is calculated as $P(r|m)=\Pi_j P(r_j|\text{Beta}(\eta,\rho))=\Pi_j \int_0^1$ Bernoulli($r_j$|p)Beta(p|η,ρ)dp, wherein Beta(η,η) is a beta function, and wherein p is an average methylation rate of a CpG at site j.

16. The method of claim 13, further comprising calculating a likelihood P(r|m) of the methylation status of the sequencing read $r=(r_1, r_2, \ldots)$ given a methylation pattern m, wherein the likelihood is calculated as $$P(r|m) = \prod_i \int_0^1 p^{r_j}(1-p)^{1-r_j} \frac{p^{\eta-1}(1-p)^{\rho-1}}{B(\eta,\rho)} dp$$

$$= \prod_j \frac{B(r_j+\eta, 1-r_j+\rho)}{B(\eta,\rho)},$$

wherein Beta(η,ρ) is a beta function, and wherein p is an average methylation rate of a CpG at site j.

17. The method of claim 13, wherein the methylation status $r_j$ in the number of sequencing reads N of the cfDNA methylation profile comprises a CpG site model that does not consider inter-individual variances.

18. The method of claim 13, wherein the methylation status $r_j$ in the number of sequencing reads N of the cfDNA methylation profile comprises a bin model that does not consider inter-individual variances.

19. The method of claim 13, wherein the methylation status $r_j$ in the number of sequencing reads N of the cfDNA methylation profile comprises a bin model that considers inter-individual variances.

20. The method of claim 12, wherein the ctDNA burden θ is calculated determined using a maximum likelihood estimation $P(R|\theta, \mathcal{M})$, wherein R denotes a set of N sequencing reads of the cfDNA methylation profile, expressed as $R=\{r^{(1)}, \ldots, r^{(N)}\}$, wherein $\mathcal{M}$ denotes methylation patterns of the set of K DNA methylation marker regions in the cfDNA methylation profile, expressed as $\mathcal{M} = \{(m_1^T, m_1^N), \ldots, (m_k^T, m_k^N), \ldots, (m_K^T, m_K^N)\}$, and wherein $P(R|\theta, \mathcal{M}) = \Pi_{i=1}^{N}(\theta P(r^{(i)}|m_k^T) + (1-\theta)P(r^{(i)}|m_k^N))$.

21. The method of claim 12, wherein the treatment comprises the chemotherapy.

22. The method of claim 21, wherein the chemotherapy is selected from the group consisting of an alkylating agent, an anthracycline, an epothilone, a histone deacetylase inhibitor, a Topoisomerase I inhibitor, a Topoisomerase II inhibitor, a kinase inhibitor, a nucleotide analog, nucleotide precursor analogs, a peptide antibiotic, a platinum-based anti-neoplastic, a retinoid, and a *vinca* alkaloid.

23. The method of claim 12, wherein the treatment comprises the immunotherapy.

24. The method of claim 23, wherein the immunotherapy is selected from the group consisting of a cellular therapy, an antibody therapy, and a cytokine therapy.

25. The method of claim 12, wherein the normal class comprises a plurality of different non-cancerous tissue types.

26. The method of claim 12, wherein the cfDNA of non-cancerous cells is obtained from a plurality of non-cancerous subjects.

27. The method of claim 12, further comprising determining a biological composition of the cfDNA sample based at least partially on the number of sequencing reads N of the cfDNA methylation profile.

28. The method of claim 27, wherein the biological composition of the cfDNA sample comprises a plurality of tissues.

29. The method of claim 28, wherein the plurality of tissues is modeled by J known classes with methylation signatures $\Omega^j (1 \leq j \leq J)$ and an unknown tissues type $\Omega^{J+1}$ that models cfDNA unlikely to belong to known classes of tissue types.

30. The method of claim 29, wherein determining the biological composition comprises solving a composition vector $\theta = (\theta_1, \theta_2, \ldots, \theta_J, \theta_{J+1})$ where, wherein $\theta_j$ ($1 \leq j \leq J$) is the cfDNA proportion of tissue j in the cfDNA sample and $\Sigma_{j=1}^{J+1} \theta j = 1$.

31. The method of claim 28, wherein the plurality of tissues comprises at least two of: liver tissue, lung tissue, kidney tissue, colon tissue, T-cells, B-cells, neutrophils, small intestines tissue, pancreas tissue, adrenal glands tissue, esophagus tissue, adipose tissue, heart tissue, brain tissue, and placenta tissue.

* * * * *

UNITED STATES PATENT AND TRADEMARK OFFICE
CERTIFICATE OF CORRECTION

| | |
|---|---|
| PATENT NO. | : 11,499,196 B2 |
| APPLICATION NO. | : 16/307821 |
| DATED | : November 15, 2022 |
| INVENTOR(S) | : Xianghong Jasmine Zhou et al. |

It is certified that error appears in the above-identified patent and that said Letters Patent is hereby corrected as shown below:

In the Claims

Column 56, Line 12 - delete "calculating"

Column 57, Line 10 - delete "calculated"

Column 58, Line 22 - delete "where,"

Signed and Sealed this
Nineteenth Day of September, 2023

Katherine Kelly Vidal
*Director of the United States Patent and Trademark Office*